US012066428B2

(12) United States Patent
Wang et al.

(10) Patent No.: US 12,066,428 B2
(45) Date of Patent: Aug. 20, 2024

(54) CELL-SUBSTRATE IMPEDANCE MONITORING OF CANCER CELLS

(71) Applicant: Agilent Technologies, Inc., Santa Clara, CA (US)

(72) Inventors: Xiaobo Wang, San Diego, CA (US); Yama A. Abassi, San Diego, CA (US); Nan Li, San Diego, CA (US); Lincoln Muir, San Diego, CA (US); Xiao Xu, San Diego, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 942 days.

(21) Appl. No.: 17/083,589

(22) Filed: Oct. 29, 2020

(65) Prior Publication Data

US 2021/0041418 A1 Feb. 11, 2021

Related U.S. Application Data

(63) Continuation-in-part of application No. 15/523,649, filed as application No. PCT/US2016/063066 on Nov. 21, 2016, now abandoned.

(51) Int. Cl.
*G01N 33/50* (2006.01)
*C12N 1/06* (2006.01)
(Continued)

(52) U.S. Cl.
CPC ........... *G01N 33/5011* (2013.01); *C12N 1/06* (2013.01); *C12N 5/0693* (2013.01); *C12N 7/00* (2013.01);
(Continued)

(58) Field of Classification Search
None
See application file for complete search history.

(56) References Cited

U.S. PATENT DOCUMENTS 2,656,508 A  10/1953  Coulter
3,259,842 A   7/1966  Coulter et al.
(Continued)

FOREIGN PATENT DOCUMENTS

CN     1902305 A    1/2007
CN   101400780 A    4/2009
(Continued)

OTHER PUBLICATIONS

Zhu et al. "Dynamic and label-free monitoring of natural killer cell cytotoxic activity using electronic cell sensor arrays," Journal of Immunological Methods, 2006, 309:25-33.
(Continued)

*Primary Examiner* — Lore R Jarrett

(57) ABSTRACT

Methods of assessing cytolysis of cancer cells are provided, which include: providing a cell-substrate impedance monitoring device operably connected to an impedance analyzer, adding target cells characterized as cancer cells to a well of the device adding effector cells to the well to form a test well, where the effector cells are immune cells obtained or derived from a same patient as the target cells; monitoring cell-substrate impedance of the test well before and after adding the effector cells and optionally deriving an impedance-based parameter from the impedance; and determining effectiveness of effector cell killing of the target cells by comparing the impedance or impedance-based curves over time.

20 Claims, 57 Drawing Sheets

(51) Int. Cl.
 *C12N 1/38* (2006.01)
 *C12N 5/09* (2010.01)
 *C12N 7/00* (2006.01)
 *G01N 27/02* (2006.01)

(52) U.S. Cl.
 CPC ....... *G01N 27/021* (2013.01); *G01N 33/5047* (2013.01); *C12N 1/38* (2013.01)

(56) References Cited

U.S. PATENT DOCUMENTS

| | | |
|---|---|---|
| 3,743,581 A | 7/1973 | Cady et al. |
| 3,890,201 A | 6/1975 | Cady |
| 4,072,578 A | 2/1978 | Cady et al. |
| 4,225,410 A | 9/1980 | Pace |
| 4,686,190 A | 8/1987 | Cramer et al. |
| 4,920,047 A | 4/1990 | Giaever et al. |
| 5,001,048 A | 3/1991 | Taylor et al. |
| 5,134,070 A | 7/1992 | Casnig |
| 5,187,096 A | 2/1993 | Giaever et al. |
| 5,218,312 A | 6/1993 | Moro |
| 5,247,827 A | 9/1993 | Shah |
| 5,278,048 A | 1/1994 | Parce et al. |
| 5,284,753 A | 2/1994 | Goodwin, Jr. |
| 5,514,555 A | 5/1996 | Springer et al. |
| 5,563,067 A | 10/1996 | Sugihara et al. |
| 5,601,997 A | 2/1997 | Tchao |
| 5,622,872 A | 4/1997 | Ribi |
| 5,626,734 A | 5/1997 | Docoslis et al. |
| 5,643,742 A | 7/1997 | Malin et al. |
| 5,725,563 A | 3/1998 | Klotz |
| 5,766,934 A | 6/1998 | Guisseppi-Ellie |
| 5,800,467 A | 9/1998 | Park et al. |
| 5,801,055 A | 9/1998 | Henderson |
| 5,810,725 A | 9/1998 | Sugihara et al. |
| 5,824,494 A | 10/1998 | Feldberg |
| 5,851,489 A | 12/1998 | Wolf et al. |
| 5,981,268 A | 11/1999 | Kovacs et al. |
| 6,033,628 A | 3/2000 | Kaltenbach et al. |
| 6,051,422 A | 4/2000 | Kovacs et al. |
| 6,132,683 A | 10/2000 | Sugihara et al. |
| 6,169,394 B1 | 1/2001 | Frazier et al. |
| 6,232,062 B1 | 5/2001 | Kayyem et al. |
| 6,235,520 B1 | 5/2001 | Malin et al. |
| 6,280,586 B1 | 8/2001 | Wolf et al. |
| 6,288,527 B1 | 9/2001 | Sugihara et al. |
| 6,368,795 B1 | 4/2002 | Hefti |
| 6,368,851 B1 | 4/2002 | Baumann et al. |
| 6,376,233 B1 | 4/2002 | Wolf et al. |
| 6,377,057 B1 | 4/2002 | Borkholder |
| 6,440,662 B1 | 8/2002 | Gerwen et al. |
| 6,448,030 B1 | 9/2002 | Rust et al. |
| 6,448,794 B1 | 9/2002 | Cheng et al. |
| 6,461,808 B1 | 10/2002 | Bodner et al. |
| 6,472,144 B2 | 10/2002 | Malin et al. |
| 6,485,905 B2 | 11/2002 | Hefti |
| 6,492,175 B1 | 12/2002 | Mueller et al. |
| RE37,977 E | 2/2003 | Sugihara et al. |
| 6,535,822 B2 | 3/2003 | Mansky et al. |
| 6,566,079 B2 | 5/2003 | Hefti |
| 6,573,063 B2 | 6/2003 | Hochman |
| 6,596,499 B2 | 7/2003 | Jalink |
| 6,626,902 B1 | 9/2003 | Kucharczyk et al. |
| 6,627,461 B2 | 9/2003 | Chapman et al. |
| 6,630,359 B1 | 10/2003 | Caillat et al. |
| 6,637,257 B2 | 10/2003 | Sparks |
| 6,638,743 B2 | 10/2003 | Baumann et al. |
| RE38,323 E | 11/2003 | Sugihara et al. |
| 6,649,402 B2 | 11/2003 | Van der Weide et al. |
| 6,686,193 B2 | 2/2004 | Maher et al. |
| 6,716,620 B2 | 4/2004 | Bashir et al. |
| 6,723,523 B2 | 4/2004 | Lynes et al. |
| 6,803,229 B2 | 10/2004 | Martin et al. |
| 6,835,552 B2 | 12/2004 | Miles et al. |
| 6,846,639 B2 | 1/2005 | Miles et al. |
| 6,852,525 B1 | 2/2005 | Cantor |
| 6,998,249 B1 | 2/2006 | McKim et al. |
| 7,010,347 B2 | 3/2006 | Schecter |
| 7,192,752 B2 | 3/2007 | Xu et al. |
| 7,208,279 B2 | 4/2007 | Gilchrist et al. |
| 7,294,334 B1 | 11/2007 | Michal et al. |
| 7,399,631 B2 | 7/2008 | Giaever et al. |
| 7,459,303 B2 | 12/2008 | Wang et al. |
| 7,468,255 B2 | 12/2008 | Xu et al. |
| 7,470,533 B2 | 12/2008 | Xu et al. |
| 7,470,583 B2 | 12/2008 | Weimer |
| 7,476,827 B1 | 1/2009 | Bhullar et al. |
| 7,510,699 B2 | 3/2009 | Black et al. |
| 7,553,448 B2 | 6/2009 | Kumar et al. |
| 7,560,269 B2 | 7/2009 | Wang et al. |
| 7,732,127 B2 | 6/2010 | Wang et al. |
| 7,842,246 B2 | 11/2010 | Wohlstadter et al. |
| 7,876,108 B2 | 1/2011 | Abassi et al. |
| 8,026,080 B2 | 9/2011 | Wang et al. |
| 8,041,515 B2 | 10/2011 | Wang et al. |
| 8,206,903 B2 | 6/2012 | Wang et al. |
| 8,263,375 B2 | 9/2012 | Abassi et al. |
| 8,344,742 B2 | 1/2013 | Abassi et al. |
| 8,420,363 B2 | 4/2013 | Wang et al. |
| 8,916,357 B2 | 12/2014 | Abassi et al. |
| 8,921,041 B2 | 12/2014 | Wang et al. |
| 9,399,787 B2 | 7/2016 | Abassi et al. |
| 9,612,234 B2 | 4/2017 | Li et al. |
| 9,625,472 B2 | 4/2017 | Xu et al. |
| 9,709,548 B2 | 7/2017 | Wang et al. |
| 10,067,121 B2 | 9/2018 | Abassi et al. |
| 10,168,318 B2 | 1/2019 | Abassi et al. |
| 10,215,748 B2 | 2/2019 | Abassi et al. |
| 2002/0032531 A1 | 3/2002 | Mansky et al. |
| 2002/0076690 A1 | 6/2002 | Miles et al. |
| 2002/0086280 A1 | 7/2002 | Lynes et al. |
| 2002/0090649 A1 | 7/2002 | Chan et al. |
| 2002/0110847 A1 | 8/2002 | Baumann et al. |
| 2002/0150886 A1 | 10/2002 | Miles et al. |
| 2003/0032000 A1 | 2/2003 | Liu et al. |
| 2003/0072549 A1 | 4/2003 | Facer et al. |
| 2003/0104512 A1 | 6/2003 | Freeman et al. |
| 2003/0116447 A1 | 6/2003 | Surridge |
| 2003/0143625 A1 | 7/2003 | Martin et al. |
| 2003/0157587 A1 | 8/2003 | Gomez et al. |
| 2003/0166015 A1 | 9/2003 | Zarowitz et al. |
| 2003/0211500 A1 | 11/2003 | Woosley |
| 2004/0083452 A1* | 4/2004 | Minor ............... G16B 50/20 717/109 |
| 2004/0091397 A1 | 5/2004 | Picard |
| 2004/0106095 A1 | 6/2004 | Thomson |
| 2004/0146849 A1 | 7/2004 | Huang et al. |
| 2005/0014130 A1 | 1/2005 | Liu et al. |
| 2005/0153425 A1 | 7/2005 | Xu et al. |
| 2005/0182447 A1 | 8/2005 | Schecter |
| 2005/0287065 A1 | 12/2005 | Suddarth et al. |
| 2006/0023559 A1 | 2/2006 | Xu et al. |
| 2006/0050596 A1 | 3/2006 | Abassi et al. |
| 2006/0057771 A1 | 3/2006 | Kovacs et al. |
| 2006/0121446 A1 | 6/2006 | Abassi et al. |
| 2006/0161073 A1 | 7/2006 | Singer et al. |
| 2006/0216203 A1 | 9/2006 | Fuller et al. |
| 2006/0240490 A1 | 10/2006 | Lee |
| 2006/0252054 A1 | 11/2006 | Lin et al. |
| 2007/0042347 A1 | 2/2007 | Rosen et al. |
| 2007/0087333 A1 | 4/2007 | Gruters et al. |
| 2007/0212423 A1 | 9/2007 | Epstein et al. |
| 2008/0190783 A1 | 8/2008 | Hyland |
| 2008/0286750 A1 | 11/2008 | Xu et al. |
| 2008/0300273 A1* | 12/2008 | Christensen ....... A61K 31/4545 514/318 |
| 2009/0017465 A1 | 1/2009 | Xu et al. |
| 2009/0142790 A1 | 6/2009 | Fang et al. |
| 2009/0155821 A1 | 6/2009 | Kunich et al. |
| 2009/0325213 A1 | 12/2009 | Gambari et al. |
| 2010/0029506 A1 | 2/2010 | Wang et al. |
| 2011/0231103 A1 | 9/2011 | Fang |
| 2011/0300569 A1 | 12/2011 | Li et al. |
| 2012/0142031 A1 | 6/2012 | Xu et al. |

(56) References Cited

U.S. PATENT DOCUMENTS

| | | | |
|---|---|---|---|
| 2012/0295253 | A1 | 11/2012 | Abassi et al. |
| 2012/0322050 | A1 | 12/2012 | Abassi et al. |
| 2013/0123136 | A1 | 5/2013 | Abassi et al. |
| 2014/0203818 | A1 | 7/2014 | Wang et al. |
| 2015/0118243 | A1* | 4/2015 | Maris ............. A61P 35/00 506/16 |
| 2015/0125894 | A1 | 5/2015 | Laing et al. |
| 2015/0150803 | A1* | 6/2015 | Boucher ........... A61K 45/06 128/200.23 |
| 2015/0185206 | A1 | 7/2015 | Abassi et al. |
| 2017/0205391 | A1 | 7/2017 | Li et al. |
| 2017/0269062 | A1 | 9/2017 | Abassi et al. |
| 2017/0315131 | A1 | 11/2017 | Xu et al. |
| 2017/0370907 | A1 | 12/2017 | Abassi et al. |
| 2018/0246079 | A1 | 8/2018 | Wang et al. |

FOREIGN PATENT DOCUMENTS

| | | | |
|---|---|---|---|
| EP | 1195432 | B1 | 6/2004 |
| EP | 1040345 | B1 | 3/2006 |
| EP | 1138758 | B1 | 1/2007 |
| EP | 2213721 | A1 | 8/2010 |
| EP | 2291645 | B1 | 9/2015 |
| WO | 1996/001836 | A1 | 1/1996 |
| WO | 1999/066329 | A1 | 12/1999 |
| WO | 2000/037628 | A1 | 6/2000 |
| WO | 2000/070343 | A2 | 11/2000 |
| WO | 2000/071669 | A1 | 11/2000 |
| WO | 2001/025769 | A3 | 4/2001 |
| WO | 2001/0038873 | A3 | 5/2001 |
| WO | 2001/079529 | A1 | 10/2001 |
| WO | 2002/0004943 | A3 | 1/2002 |
| WO | 2002/0042766 | A3 | 5/2002 |
| WO | 2003/016887 | A3 | 2/2003 |
| WO | 2004/010103 | A2 | 1/2004 |
| WO | 2005/005979 | A1 | 1/2005 |
| WO | 2005/047482 | A2 | 5/2005 |
| WO | 2005/077104 | A2 | 8/2005 |
| WO | 2006/015387 | A2 | 2/2006 |
| WO | 2006/015387 | A3 | 2/2006 |
| WO | 2006/017762 | A2 | 2/2006 |
| WO | 2007/082138 | A2 | 7/2007 |
| WO | 2007082138 | A3 | 7/2007 |
| WO | 2009/137440 | A1 | 11/2009 |
| WO | 2010/129725 | A1 | 11/2010 |
| WO | 2011/146531 | A1 | 11/2011 |
| WO | 2012/043820 | A1 | 4/2012 |
| WO | 2012/048320 | A1 | 4/2012 |
| WO | 2012/048320 | A2 | 4/2012 |
| WO | WO2013177214 | * | 11/2013 ............. G06F 19/18 |
| WO | 2014/085727 | A1 | 6/2014 |
| WO | 2015/058861 | A1 | 4/2015 |
| WO | 2017/087945 | A1 | 5/2017 |

OTHER PUBLICATIONS

Labuda et al. "Decoupling conservative and dissipative forces in frequency modulation atomic force microscopy," Physical Review, 2011, B 84(125433):125433-1-125433-11.

CN201680079414.5 Office Action and Search Report mailed Jun. 22, 2021.

Lei "Review on Impedance Detection of Cellular Responses in Micro/Nano Environment," Micromachines, 2014, 5, 1-12; doi: 10.3390/mi5010001.

Mishra et al. "On-Chip Micro-Biosensor for the Detection of Human CD4+ Cells Based on AC Impedance and Optical Analysis," Biosensors and Bioelectronics, 2005, 21:696-704.

Sun et al. "New Edition of Clinical Tumor Diagnosis and Treatment," Xi'an Jianlong University Press, 2015, p. 199.

Xu et al. "Nano-Biomedical Technology," Peking Union Medical College Press, 2009, p. 166.

CA2556219 Office Action mailed Aug. 9, 2010.

CA2575573 Office Action mailed Apr. 4, 2012.

EP10772804.0 Extended European Search Report mailed Oct. 27, 2017.

EP09743420 European Search Report mailed Nov. 26, 2013.

EP13171137 Extended European Search Report mailed Aug. 16, 2013.

EP05786773 Extended European Search Report mailed Mar. 21, 2013.

EP11193882 Extended European Search Report mailed Apr. 5, 2012.

EP05722991 Extended European Search Report mailed Apr. 3, 2009.

EP05852157 Extended European Search Report mailed Sep. 13, 2011.

EP058122680 Extended European Search Report mailed Sep. 7, 2011.

EP03748948 Extended European Search Report mailed Mar. 12, 2007.

PCT/US2013/072439 International Search Report mailed Feb. 19, 2014.

PCT/US2011/036877 International Search Report mailed Sep. 2, 2011.

PCT/US2009/033801 International Search Report and Written Opinion mailed Jul. 9, 2010.

PCT/US2009/042787 International Search Report and Written Opinion mailed Jun. 24, 2009.

PCT/US2005/027943 International Preliminary Report on Patentability mailed Apr. 11, 2007.

PCT/US2005/034561 International Preliminary Report on Patentability mailed Mar. 27, 2007.

PCT/US2005/027943 International Search Report and Written Opinion mailed Mar. 21, 2007.

PCT/US2005/034561 International Search Report mailed Sep. 27, 2006.

PCT/US2005/04481 International Search Report mailed Sep. 12, 2005.

PCT/US2004/037696 International Search Report mailed May 16, 2005.

"Label-Free Assay for NK Cell-Mediated Cytolysis," Jan. 1, 2013, pp. 1-8, retrieved from the internet May 23, 2019, URL discloses a method of assessing the effect of e.g. NK cell-mediated cytolysis on target cells using a cell substrate impedance monitoring devices indentical to the one used in the application as filed.

"xCELLigence System Application Table of Contents," Jan. 1, 2014, retrieved from the internet May 23, 2014, URL: https://www.ols-bio.de/media/pdf/Application_Book_09082014_OLS_xs.pdf.

Lamarche et al. Using Impedance-Based Approaches for Measuring Cell-Mediated Cytotoxicity and Antibody-Dependent Cell-Mediated Cytotoxicity (ADCC), Journal of Immuno Therapy of Cancer, Nov. 4, 2015, 3(Suppl 2): p. 214.

Acea Biosciences, "Cancer Immunotherapy Applications of xCELLigence Real-Time Cell Analysis(RTCA) Systems", ACEA Biosciences, Nov. 17, 2015, 1-16.

Chou, et al., "Epigenetic Modulation to Enable Antigen-specific T-cell Therapy of Colorectal Cancer", Journal of Immunotherapy, vol. 35, No. 2, Jan. 1, 2012, 131-141.

Davenport, et al., "CAR-T Cells Inflict Sequential Killing of Multiple Tumor Target Cells", Cancer Immunology Research, vol. 3, No. 5, Feb. 24, 2015, 483-494.

El-Andaloussi, et al., "Generation of an Adenovirus-Parvovirus Chimera with Enhanced Oncolytic Potential", Journal of Virology, the American Society for Microbiology, vol. 86, No. 19, Oct. 1, 2012, 10418-10431.

EPO, "Extended European Search Report mailed on Nov. 11, 2019", Application No. 16867327.5, 26 pages.

Junwei, et al., "Synergistic combination of valproic acid and oncolytic parvovirus H-1PV as a potential therapy against cervical and pancreatic carcinomas", EMBO Molecular Medicine, vol. 5, No. 10, Sep. 17, 2013, 1537-1555.

Oberg, et al., "Novel Bispecific Antibodies Increase gammadelta T-Cell Cytotoxicity against Pancreatic Cancer Cells", Cancer Research, vol. 74, No. 5 Proceedings: AACR 107th Annual Meeting—Apr. 16-20, 2016, Jan. 21, 2014, 1349-1360.

(56) References Cited

OTHER PUBLICATIONS

Prasad, et al., "Chemical Induction of Unfolded Protein Response Enhances Cancer Cell Killing through Lytic Virus Infection", Journal of Virology, vol. 88, No. 22, Nov. 15, 2014, 13086-13098.
Schanzer, et al., "A Novel Glycoengineered Bispecific Antibody Format for Targeted Inhibition of Epidermal Growth Factor Receptor (EGFR) and Insulin-like Growth Factor Receptor Type I (IGF-1R) Demonstrating Unique Molecular Properties", Journal of Biological Chemistry, vol. 289, No. 27, May 19, 2014, 18693-18706.
Schmittnaegel, et al., "Committing Cytomegalovirus-Specific CD8 T Cells to Eliminate Tumor Cells by Bifunctional Major Histocompatibility Class I Antibody Fusion Molecules", Cancer Immunology Research, vol. 3, No. 7, Feb. 17, 2015, 764-776.
Seidel, et al., "gammadeltaT Cell-Mediated Antibody-Dependent Cellular Cytotoxicity with CD19 Antibodies Assessed by an Impedance-Based Label-Free Real-Time Cytotoxicity Assay", Dec. 2, 2014, 3155-3162.
Cartellieri et al. "Chimeric Antigen Receptor-Engineered T Cells for Immunotherapy of Cancer," Journal of Biomedicine and Biotechnology, May 5, 2010, 2010(956304):1-13.
Maher et al. "Targeting cytotoxic T lymphocytes for cancer immunotherapy," British Journal of Cancer, 2004, 91(5):817-821.
Aravanis et al. "A Genetically Engineered Cell-Based Biosensor for Functional Classification of Agents." Biosensors & Bioelectronics, 2001, 16:571-577.
Banach et al. "Development of Electrical Activity in Cardiac Myocyte Aggregates Derived from Mouse Embryonic Stem Cells." Amerocam Journal of Physiology-Heart Circulatoy Physiology, 2003, 284: H2114-H2123.
Baumann et al., "Microelectronic Sensor System for Microphysical Application on Living Cells", Sensors and Actuators, 1999:77-89.
Becker et al. "Separation of Human Breast Cancer Cells from Blood by Differential Dielectric Affinity." Cell Biology, 1995, 92:960-964.
Berdondini et al. "High-Density Electrode Array for Imaging in Vitro Electrophysiological Activity." Biosensors and Bioelectronics, 2005, 21:167-174.
Berens et al. "The Role of Extracelluar Matrix in Human Astrocytoma Migration and Proliferation Studied in a Microliter Scale Assay." Clinical and Experimental Metastasis, 1994; 12(6):405-415.
Bergveld, P. "A Critical Evaluation of Direct Electrical Protein Detection Methods." Biosensors & Bioelectronics. 6:55-72 (1991).
Bieberich et al. "Neuronal Differentiation and Synapse Formation of PC12 and Embryonic Stem Cells on Interdigitated Microelectrode Arrays," Biosensors and Bioelectronics 2004; 19:923-931.
Blagbrough et al. "Polyamines and Novel Polyamine Conjugates Interact with DNA in Ways That Can Be Exploited in Non-Viral Gene Therapy." Biochemical Society Transactions, 2003, 31, Part 2, pp. 397-406.
Bonetta, Laura. "The Inside Scoop-Evaluating Gene Delivery Methods." Nature Methods, Nov. 2005, 2(11):875-883.
Burnett et al. "Fluorescent Imaginng of Electrically Stimulated Cells." Journal of Biomolecular Screening 2003; 8(6):660-667.
Burns et al. "Neutrophil Transendothelial Migration Is Independent of Tight Junctions and Occurs Preferentially at Tricellular Corners." Journal of Immunology, 1997, 2893-2903.
Cady et al. "Electrical Impedance Measurements: Rapid Method for Detecting and Monitoring Microorganisms," Journal of Clinical Mirobiology, 1978; 7(3):265-272.
Chang et al. "Impedimetric Monitoring of Cell Attachment on Interdigitated Microelectrodes." Sensors and Actuators, 2005, B 105:159-163.
Ciambrone et al. "Cellular Dielectric Spectroscopy: A Powerful New Approach to Label-Free Cellular Analysis." Journal of Biomolecular Screening, 2004, 9(6):467-480.
Connolly et al. "An Extracelluluar Microelectrode Array for Monitoring Electrogenic Cells in Culture," Biosensors and Bioelectronics, 1190, 5:223-234.
Duan et al. "Separation-Free Sandwich Enzyme Immunoassays Using Microporous Gold Electrodes and Self-Assembled Monolayer/Immobilized Capture Antibodies." Analytical Chemistry, 1994, 66:1369-1377.
Ehret et al. "Monitoring of Cellular Behaviour by Impedance Measurements on Interdigitated Electrode Structures." Biosensors and Bioelectronics 1997; 12(1):29-41.
Ehret et al. "On-Line Control of Cellular Adhesion with Impedance Measurements Using Interdigitated Electrode Structures", Medical & Biological Engineering & Computing, 1998; 36:365-370.
Falk et al. "A 48-well Micro Chemotaxis Assembly for Rapid and Accurate Measurement of Leukocyte Migration." Journal of Immunological Methods., 1980, 33:239-247.
Fuhr et al. "Positioning and Manipulation of Cells and Microparticles Using Miniaturized Electric Field Traps and Travelling Waves." Sensors and Materials 7(2):131-146 (1995).
Giaever et al. "Micromotion of Mammalian Cells Measured Electrically." Proceedings of the National Academy of Sciences, USA, 1991; 8(Sept.):7896-7900.
Giaever et al, "Monitoring Fibroblast Behavior in Tissue Culture with an Applied Electric Field." Proceedings of the National Academy of Sciences. USA; 1984; 81(June):3761-3764.
Gutmann et al. "Evidence for Different ABC-Transporters in Caco-2 Cells Modulating Drug Uptake." Pharmaceutical Research, 1999, 16(3):402-407.
Hadjout et al. "Automated Real-Time Measurement of Chemotactic Cell Motility." BioTechniques, 2001, 31:1130-1138.
Hapala, Ivan. "Breaking the Barrier: Methods for Reversible Permeabilization of Cellular Membranes." Critical Reviews in Biotechnology, 1997, 17(2):105-122.
Henning et al. "Approach to a Mutliparametric Sensor-Chip-Based Tumor Chemosensitivity Assay," Anti-Cancer Drugs 2001; 12:21-32.
Hescheler et al. "Determination of Electrical Properties of ES Cell-derived Cardiomyocytes Using MEAs." Journal of Electrocardiology, 2004, vol. 37, Suppl.
Hidalgo et al. "Characterization of the Human Colon Carcinoma Cell Line (Caco-2) as a Model System for Intestinal Epithelial Permeability," Gastroenterology, 1989; 96:736-749.
Horvath et al. "Monitoring of Living Cell Attachment and Spreading Using Reverse Symmetry Waveguide Sensing." Applied Physics Letters, 2005, 86:071101.
Huang et al. "Dielectrophoretic Cell Separation and Gene Expression Profiling on Microelectronic Chip Arrays." Analytical Chemistry, 2002, 74:3362-3371.
Hug, Thomas, "Biophysical Methods for Monitoring Cell-Substrate Interactions in Drug Discovery." Assay and Drug Development Technologies, 2003; 1(3):479-488.
Keese et al. "Real-time Impedance Assay to Follow the Invasive Activities of Metastatic Cells in Culture." BioTechniques, 2002, 33:842-850.
Klauke et al. "Extracellular Recordings of Field Potentials from Single Cardiomyocytes." Biophysical Journal, Oct. 2006, 91:2543-2551.
Kleinman et al. "Basement Membrane Complexes with Biological Activity." Biochemistry 1986; 25(2):312-318.
Kloss et al. "Microcavity Array (MCA)-Based Biosensor Chip for Functional Drug Screening of 3D Tissue Models." Biosensors and Bioelectronics, 2008, 23:1473-1480.
Kowolenko et al. "Measurement of Macrophage Adherence and Spreading with Weak Electric Fields." Journal of Immunological Methods, 1990; 127:71-77.
Larsen et al. "Somatic Cell Counting with Silicon Apertures." Micro Total Analysis Systems, 2000, 103-106.
Lin et al. "Electroporation Microchips for In Vitro Gene Transfection." Journal of Micromechanics and Microengineering, 2001, 11:542-547.
Lin et al. "Simulation and Experimental Demonstration of the Electric Field Assisted Electroporation Microchip for In Vitro Gene Delivery Enhancement." Miniaturisation for Chemistry, Biology & Bioengineerin., 2004, 4:104-108.

(56) References Cited

OTHER PUBLICATIONS

Lo et al. American Physical Society March Meeting 2010, Portland Oregon, vol. 55, No. 2, Poster Session Abstract, BAPS, Mar. 2010 C1 268.
Lo et al. "Impedance Analysis of MDCK Cells Measured by Electric Cell-Substrate Impedance Sensing." Biophysical Journal, 1995, 69:2800-2807.
Lo et al. "Monitoring Motion of Confluent Cells in Tissue Culture." Experimental Cell Research 1983; 204:102-109.
Lo et al. "pH Changes in pulsed CO2 incubators cause periodic changes in cell morphology." Experimental Cell Research, 1994, 213:391-397.
Loffert et al. "Multiplex PCR with QIAGEN: Taq DNA Plymerase and PCR Buffer." QIAGENews, 1994, 4:15-18.
Luan et al. "Clustering of Time-Course Gene Expression Data Using a Mixed-Effects Model with B-Splines." Bioinformatics, 2003, 19(4):474-482.
Luong et al. "Monitoring Motility, Spreading and Mortality of Adherent Insect Cells Using an Impedance Sensor.", Analytical Chemistry, 2001, 73(8):1844-1848.
Mitra et al. "Electric Measurements Can Be Used to Monitor the Attachment and Spreading of Cells in Tissue Culture." Biotechniques, 1991, 11(4):504-510.
Miyata et al. "New Wound-Healing Model Using Cultured Corneal Endothelial Cells." Japan Journal of Opthalmology, 1990, 34:257-266.
Mohr et al. "Performance of a Thin Film Microelectrode Array for Monitoring Electrogenic Cells in Vitro." Sensors and Actuators, B34:265-269 (1996).
Neher, Erwin, "Molecular Biology Meets Microelectronics." Nature Biotechnology, 2001; 19:114.
Nerurkar et al. "The Use of Surfactants to Enhance the Permeability of Peptides Through Caco-2 Cells by Inhibition of an Apically Polarized Efflux System." Pharmaceutical Research, 1996, 13(4):528-534.
Nicolazzi et al. "Cationic Lipids for Transfection." Current Medicinal Chemistry, 2003, 10:1263-1277.
Oka et al. "A New Planar Multielectrode Array for Extracellular Recording: Application to Hippocampal Acute Slice." Journal of Neuroscience Methods, 1999, 93:61-67, Elsevier Science, B.V.
Ong et al. "Remote Query Resonant-Circuit Sensors for Monitoring of Bacterial Growth: Application to Food Quality Control." Sensors 2002; 2:219-232.
Pancrazio et al. "Portable Cell-Based Biosensor System for Toxin Detection." Sensors and Actuators 1998; 53:179-185.
Patolsky et al. "Detection of Single-Base DNA Mutations by Enzyme-Amplified Electronic Transduction." Nature Biotechnology, 2001, 19:253-257.
Pethig et al. "Positive and Negative Dielectrophoretic Collection of Colloidal Particles Using Interdigitated Castellated Microelectrodes." Applied Physics, 1992, 24:881-888.
Qiu et al. "Real-Time Monitoring Primary Cardiomyocyte Adhesion Based on Electrochemical Impedance Spectroscopy and Electrical Cell-Substrate Impedance Sensing" Analytical Chemistry, 2008, 80:990-996.
Rabow et al. "Mining the National Cancer Institute's Tumor-Screening Database: Identification of Compounds with Similar Cellular Activities." Journal of Medicinal Chemistry, 2002, 45:818-840.
Richards et al. "A Modified Microchamber Method for Chemotaxis and Chemokinesis." Immunological Communications, 1984, 13 (1):49-62.
Rishpon et al. "An Amperometric Enzyme-channeling Immunosensor." Biosensors & Bioelectronics, 1997, 12 (3):195-204.
Simpson et al. "Whole-Cell Biocomputing." Trends in Biotechnology, 2001, 19(9):317-323.
Slaughter et al. "Artificial Neural Network for Temporal Impedance Recognition of Neurotoxins." 2006 International Joint Conference on Neural Networks Jul. 16-21, 2006: 2001-2008.
Sohn et al. "Capacitance Cytometry: Measuring Biological Cells One by One." Proceedings of the National Academy of Sciences, 2000, 97(20):10687-10690.
Steinem et al. "Impedance and Shear Wave Resonance Analysis of Ligand-Receptor Interactions at Functionalized Surfaces and of Cell Monolayers." Biosensors & Bioelectronics, 1997, 12(8):787-808.
Stenger et al. "Detection of Physiologically Active Compounds Using Cell-Based Biosensors." Trends in Biotechnology, 2001; 19(8):304-309.
Svetlicic et al. "Charge Displacement by Adhesion and Spreading of a Cell." Bioelectrochemistry, 2000, 53:79-86.
Tiruppathi et al. "Electrical Method for Detection of Endothelial Cell Shape Change in Time: Assessment of Endothelial Barrier Function." Proceedings of the National Academy of Sciences, USA , 1992, 89:7919-7923.
Wang et al. "A Theoretical Method of Electrical Field Analysis for Dielectrophoretic Electrode Arrays Using Green's Theorem." Journal of Phyics D: Applied Physics, 1996; 29:1649-1660.
Wang et al. "Cell Separation by Dielectrophoretic Field-Flow-Fractionation." Analyitcal Chemistry., 2000, 72:832-839.
Wang et al. "Dielectrophoretic Manipulation of Cells with Spiral Electrodes." Biophysical Journal, 1997, 72:1887-1899.
Wang et al. "Electronic Manipulation of Cells on Microchip-Based Devices." In Biochip Technology (eds), 2001, pp. 135-159, Harwood Academic Publishers, PA, USA.
Wang et al. "Separation of Polystyrene Microbeads Using Dielectrophoretic/Gravitational Field-Flow-Fractionation." Biophysical Journal, 1998, 74:2689-2701.
Wang et al. "Selective Dielectrophoretic Confinement of Bioparticles in Potential Energy Wells." Applied Physics, 1993, 26:1278-1285.
Warburg Ueber die Polarisationscapacitat des Platins. Annals of Physics, 6:125-135 (1901).
Wegener et al. "Electric Cell-Substrate Impedance Sensing (ECIS) as Noninvasive Means to Monitor the Kinetics of Cell Spreading to Artificial Surfaces." Experimental Cell Research 2000; 259:158-166.
Wegener et al., Use of Electrochemical Impedance Measurements to Monitor Beta-Adrenergic Stimulation of Bovine Aortic Endothelial Cells. European Journal of Physiology, 437:925-934 (1999).
Wolf et al. "Monitoring of Cellular Signalling and Metabolism with Modular Sensor-Technique: The PhysioControl-Microsystem (PCM)." Biosensors and Bioelectronics 1998; 13:501-509.
Xiao et al. "An In-Depth Analysis of Electric Cell-Substrate Impedance Sensing to Study the Attachment and Spreading of Mammalian Cells." Analytical Chemistry, 2002; 74(6):1333-1339.
Xiao et al. "Assessment of Cytotoxicity Using Electric Cell-Substrate Impedance Sensing: Concentration and Time Response Function Approach." Analytical Chemistry, 2002, 74:5748-5753.
Xiao et al. "On-Line Monitoring of Cell Growth and Cytotoxicity Using Electric Cell-Substrate Impedance Sensing (ECIS)." Biotechnology Progress, 2003; 19:1000-1005.
Xing et al. "Dynamic Monitoring of Cytotoxicity on Microelectronic Sensors" Chemical Research in Toxicology., 2005, 18 (2):154-161.
Yamauchi et al. "Spatially and Temporally Controlled Gene Transfer by Electroporation into Adherent Cells on Plasmid DNA-Loaded Electrodes." Nucleic Acids Research, 2004, 32(22):1-8.
Yang et al. "A Novel Microfluidic Impedance Assay for Monitoring Endothelin-Induced Cardiomyocyte Hypertrophy." Biosensors and Bioelectronics, 2007, 22:1688-1693.
Yang et al. "Cell Separation on Microfabricated Electrodes Using Dielectrophoretic/Gravitational field-flow Fractionation." Analytical Chemistry, 1999, 71:911-918.
Yu et al. "Real-Time Monitoring of Morphological Changes in Living Cells by Electronic Cell Sensor Arrays: An Approach to Study G Protein-Coupled Receptors." Analytical Chemistry, 2006, 78:35-43.
"Automated Cell Monitoring Instrument." Applied BioPhysics, 2002, [retrieved from the internet] http://www.biophysics.com/pages/front.html, 1 page.
"Cell Migration Studies with TECAN Systems." TECAN., Sep. 1999, [retrieved from the internet] http://www.tecan.com/migration_introl.pdf, 10 pgs.

(56) References Cited

OTHER PUBLICATIONS

"Detect Cell Migration and Invasion in a Homogeneous Fluorescent Assay System." BD Biosciences, http://www.bdbiosciences.com/discovery_labware/Products/inserts/BD_Falcon_HTS_fluoroblok_inserts/individual_fluoroblok_inserts/index.html, 2004.

HP 4284A Precision LCR Meter Operation Manual, Aug. 1998, Hewlett Packard, 6th Edition, p. 1-460.

"Molecular Viewer" New Products page. Science 298:2409 (2002).

"Neuro Probe AA96, AB96, AC96 Chemotaxis Chambers." Neuro Probe, [retrieved from the internet] http://www.neuroprobe.com/protocol/pt_96a.html, 5 pgs.

PCT/US2016/063066 International Search Report and Written Opinion mailed Jan. 30, 2017.

EP16867327.5 Supplementary Partial European Search Report mailed Jun. 6, 2019.

Carrega et al. "Susceptibility of Human Melanoma Cells to Autologous Natural Killer (NK) Cell Killing: HLA-Related Effector Mechanisms and Role of Unlicensed NK Cells." PLoS One, Dec. 4, 2009, 4(12):e8132.

Peper et al. "An Impedance-Based Cytotoxicity Assay for Real-Time and Label-Free Assessment of T-Cell-Mediated Killing of Adherent Cells," Journal of Immunological Methods, Jan. 29, 2014, 405:192-198.

Oberg et al. "Monitoring Circulating gamma-delta-T Cells in Cancer Patients to Optimize gamma-delta-T Cell-Based Immunnotherapy." Frontiers in Immunology, Dec. 17, 2014, 5(643):1-7.

Erskine et al. "Determining Optimal Cytotoxic Activity of Human Her2neu Specific CD8 T Cells by Comparing the CR51 Release Assay to the xCELLigence System," Journal of Visualized Experiments, Aug. 8, 2012, 66(e3683):1-6.

Alici et al. "Autologous Antitumor Activity by NK Cells Expanded from Myeloma Patients Using GMP-Compliant Components," Blood, Mar. 15, 2008, 111(6):3155-3162.

Tao et al. "Strategy of enhancing the effectiveness of adoptive cell immunotherapy and the progress in the study," Oncology Progress, Nov. 2014, 12(6):522-527.

Lei, Qiumo, Ed. "Practical Pathology of Breast Diseases," Sep. 2012, 183-184.

Yao, Wenbing, Ed. "Introduction to Biotechnological Pharmaceutics," Aug. 2015, 238-239.

Lu et al. "Enhanced Antitumor Effect of Cytotoxic T Lymphocytes Modiated by IL-2 Gene," Chinese Journal of Cancer, 2001, 20(8):844-847.

EP16867327.5 Communication pursuant to Article 94(3) EPC mailed Feb. 23, 2021.

Giordano Attianese et al. "In vitro and in vivo model of a novel immunotherapy approach for chronic lymphocytic leukemia by anti-CD23 chimeric antigen receptor," Blood, May 5, 2011, 117(18):4736-4745.

\* cited by examiner

Shade-coding Scheme

CCI >> 0.7/DT:

CCI ~ 0.7/DT:

0 < CCI < 0.7/DT:

CCI ~ 0:

CCI < 0:

CCI << 0:

CELL-SUBSTRATE IMPEDANCE MONITORING OF CANCER CELLS

CROSS REFERENCE TO RELATED APPLICATIONS

This is a continuation in part of U.S. patent application Ser. No. 15/523,649, filed May 1, 2017, which is a national phase entry under Section 371 of PCT/US2016/063066, filed Nov. 21, 2016, which itself claims benefit of priority to U.S. provisional patent application 62/258,121, filed Nov. 20, 2015, U.S. provisional patent application 62/302,779, filed Mar. 2, 2016, and U.S. provisional patent application 62/345,699, filed Jun. 3, 2016. Each application referenced in this application is herein incorporated by reference in its entirety.

TECHNICAL FIELD

The invention relates to cell-substrate impedance-monitoring of cancer cells and more specifically to methods for assessing the effectiveness of anticancer treatments on cancer cells using cell-substrate impedance-based devices.

BACKGROUND OF THE INVENTION

Cancer is a group of diseases involving abnormal cell growth with the potential to invade or spread to other parts of the body. When cancer begins it produces no symptoms. Symptoms appear as the mass grows or ulcerates. Cancer can spread from its original site by local spreading, lymphatic spreading to regional lymph nodes, or haematogenous spreading via the blood to distant sites, known as metastasis. When it spreads by a haematogenous route, it usually spreads all over the body. Cancer causes about 14% of human deaths.

There are a number of technical approaches underway to treat cancer. Among these include the development of new chemotherapeutic agents. Chemotherapy usually means the use of medicines or drugs to treat the cancer. A more recent experimental approach is adoptive cell transfer (ACT), which involves the transfer of cells into a patient. In different variations, the cells can be from the same patient or another individual.

As of yet, patients are not universally responsive to any particular cancer treatment and it can be difficult to predict which treatments will be effective. Therefore patients often try different treatments over the course of the cancer. Thus, there remains a need to develop methods to improve screening of potential treatments to different cancers and cancer patients.

SUMMARY OF THE INVENTION

The invention provides a cell-based assay that efficiently tests proposed cancer treatments against cancer cells collected from patients to provide an individualized approach to anticancer therapy.

In one aspect, a method of assessing cytolysis of cancer cells is provided, the method including: providing a cell-substrate impedance monitoring device operably connected to an impedance analyzer, wherein the device includes a well for receiving cells and an electrode array at a base of the well; adding target cells designated as cancer cells to the well; adding a proposed therapeutic to the well to form a test well; adding effector cells to the test well, wherein the effector cells are immune cells obtained or derived from a same patient as the target cells; monitoring cell-substrate impedance of the test well before and after adding the effector cells and optionally deriving impedance-based parameters from the impedances; and determining effectiveness of effector cell killing of the target cells by comparing the impedances or impedance based parameters over time.

High resolution configuration assays have been developed to reproducibly detect changes in cell-substrate impedance from cancer cell populations having as few as 1 to 100 cells. Among these include a single measuring electrode coupled with a large reference electrode and interdigitated electrode arrays. To this end, the cell-substrate impedance based assays can be conducted having target cell populations ranging from 1 cancer cell and up to 10,000 cancer cells or more within the well.

The method applies to target cells embodied as cancer cells obtained from a variety of biological samples. Among these include a solid tumor, a hematopoietic tumor, blood, and pleural effusion. In some embodiments, the target cells are circulating tumor cells (CTCs) collected from blood. In other embodiments, the target cells are tumor cells collected from a tissue biopsy.

The effector cells can be any suitable cells of the innate immune system. Non-limiting examples of effector cells that may be used in the methods include natural killer cells (NK cells), macrophages, neutrophils, eosinophils, T-cells, and B-cells. When the effector cells are T-cells, they can be T helper cells (Th cells), cytotoxic T cells, and/or memory T cells. In some embodiments the effector cells are tumor infiltrating lymphocytes (TILs), which in still further embodiments can be isolated from a same patient's cancer tissue from which the cancer cells are collected.

Among the uses of the technology herein is to test engineered immune cells for their selectivity to bind cancer cells from individuals for use in personalized medicine, in particular anticancer applications. In some embodiments, the effector cells are engineered to express a soluble bispecific engager, which is defined as at least two polypeptides linked together, where at least one polypeptide binds an effector cell and at least another polypeptide binds a target cell thereby joining effector cells to target cells.

In other embodiments the effector cells are engineered to display one or more chimeric antigen receptors (CARs) against one or more antigen present on the target cells. In further embodiments, the effector cells are CAR-T cells. In still further embodiments, each CAR displays one or more single-chain fragment variable (scFv) region against cancer cells.

In accordance with the above, in some embodiments the method includes a step of engineering effector cells collected from the subject to express an exogenous protein to form at least part of the CAR. In some embodiments, effector cells are further engineered to increase expression of an exogenous compound, such as but not limited to Interleukin 2, to promote growth, proliferation or persistence of the engineered effector cells.

The methods can compare impedance or impedance based parameters from a single well to determine effectiveness; however, in other embodiments the impedance or impedance based parameter of the test well is compared to that of a control well. As an example, the method can include adding the target wells to a second well of the device designated a control well; adding non-engineered effector cells from the same subject to the control well; monitoring impedance of the control well and optionally deriving an impedance-based parameter from the impedance of the control well; and comparing the impedances or impedance based parameters over time between the control well and test well to determine a difference in effectiveness of effector cell killing of the target cells in the test well.

In some embodiments, the method includes comparing cell-substrate impedance measurements, but in preferred embodiments the method includes comparing an impedance-based parameter, which is derived from impedance. Typically, a decreasing impedance or impedance based parameter over time is indicative of increased effectiveness of cytolysis of cancer cells.

In some embodiments the impedance based parameter is a single parameter, such as a cell index, a cell change index, or a normalized cell index that is normalized to a time point before adding the effector cells. In some embodiments the impedance based parameter is an impedance-based curve and in further embodiments the effectiveness of effector cell killing of target cells is determined by comparing impedance-based curves over time. However, in other embodiments the effectiveness of effector cell killing of target cells is determined by calculating and comparing a percent cytolysis of the target cells.

In some embodiments, the effectiveness of cell killing of target cells by effector cells is determined by calculating the time it takes to achieve 50% cytolysis or Killing time 50 (KT50). The KT50 value is compared for different doses of the same effector being added to separate wells containing the same number of target cells or for different effectors added at the same dose or concentration added to separate wells containing same number of target cells.

In some embodiments a linear regression of KT50 values is plotted against the corresponding effector cell concentration to assess the linearity of effector cell concentration to cytolytic activity.

In other embodiments the slope of the linear regression line of the KT50 values plotted against the effector cell concentration is determined as an independent measure of effector cell activity that is unique to the particular effector cell and wherein the slope for different effectors are compared to each other.

In some embodiments, the slope of the Cell Index curve within a given timeframe after the addition of the effector cells is calculated and plotted against the number of effector cells being added to the well containing the target cells. The linearity of the graph, particularly at low effector to target (E:T) ratios is related to the sensitivity of the assay and the direct relation of the number of effector cells being added to its cytolytic activity.

In accordance with the above, in some embodiments, the slope of the linear regression graph itself is characteristic of the activity of the effector cells being added to the target cells and can be compared to a different effector or the same effector treated with a compound, antibody or otherwise genetically engineered by different methods.

In some embodiments, the area under the curve (AUC) of the impedance trace generated after the addition of certain number of effector cells to the target cells can be calculated as a measure of the cytolytic activity of the effectors at a given cell number. Plotting the AUC value against the corresponding number of effector cells being added can generate a dose-response curve which can be quantified in terms of half-maximal activity or EC50 value as a measure of the efficacy of the effector cells.

In some embodiments, the effect of one or more compounds on cytolysis of cancer cells is assessed. Accordingly, in some embodiments the method includes a step of adding an additional compound suspected of increasing or decreasing effectiveness of effector cell killing of target cells and determining a difference in the effectiveness in response to adding the compound. A variety of compounds can be tested, including an antibody or antibody fragment, a modified antibody or antibody fragment, or a peptide. In some embodiments, the additional compound is a check point inhibitor. Check point inhibitors seek to overcome one of cancer's main defenses against an immune system attack by blocking normal proteins on cancer cells. Examples of check point inhibitors include antibodies or antibody fragments targeting PD1, CTLA-4, CD137, OX40, CD27, CD40L, TIM3 on the surface of effector cells or their respective cognate ligand on the surface of target cells.

In other embodiments, the additional compound is a bispecific engager defined as at least two polypeptides linked together, where at least one polypeptide binds an effector cell and another at least one polypeptide binds a target cell, thereby joining effector cells to target cells. In a further embodiment the bispecific engager binds a T-cell surface moiety, such as CD3.

The above aspect can be further adapted to provide a method of determining a treatment for killing of cancer cells in a patient. Such a method can include collecting a sample of cancer cells from a patient; and assessing the cytolytic activity of one or more effector cells against the cancer cells according to the above methods; and designating the effector cells (or subsequently added compound) determined effective at killing cancer cells to be a treatment for the killing of cancer cells in the patient. To this end, in some embodiments the effector cells are engineered to display a chimeric antigen receptor (CAR) against an antigen present on the target cells and in further embodiments the effector cells are CAR-T cells.

In furtherance of the above a method of killing cancer cells in vivo is also provided, which includes determining a treatment for killing of cancer cells in a patient substantially as set forth above; expanding a population of the effector cells; and administering to the patient a therapeutically effective amount of the effector cells.

In a related aspect, a method of assessing cytolysis of cancer cells is provided, which includes providing a cell-substrate impedance monitoring device operably connected to an impedance analyzer, wherein the device includes a well for receiving cells and an electrode array at a base of the well; adding one or more target cells characterized or designated as cancer cells to the well; adding effector cells to the well to form a test well, wherein the effector cells are immune cells, further wherein the effector cells are engineered to display a binding moiety suspected of binding the target cells; monitoring cell-substrate impedance of the test well before and after adding the effector cells and optionally deriving impedance-based parameters from the impedances; and determining effectiveness of effector cell killing of target cells by comparing the impedances or impedance based parameters over time.

In some embodiments the target cells are circulating tumor cells (CTCs) collected from blood. In other embodiments, the target cells are tumor cells collected from a tissue biopsy. In some embodiments the cancer cells are obtained from a biological sample selected from the group consisting of a solid tumor, a haematopoietic tumor, blood, and pleural effusion.

In some embodiments, the target cells are of a tumor cell line having a same genetic characteristic as a patient from whom the effector cells are derived.

In some embodiments the effector cells are cells of the innate immune system. Non-limiting examples of suitable effector cells include natural killer cells (NK cells), macrophages, neutrophils, eosinophils, T-cells, and/or B-cells. In some embodiments, the T cells are selected from one or more of the group consisting of T helper cells (Th cells), cytotoxic T cells, and memory T cells.

In some the binding moiety is a chimeric antigen receptor (CAR) against an antigen present on the target cells. In further embodiments, the CAR displays a single-chain fragment variable (scFv) region. In some embodiments the effector cells are CAR-T cells. In other embodiments, the binding moiety is a soluble bispecific engager having at least two polypeptides linked together, wherein at least one polypeptide binds either an effector cell and the other binds a target cell, thereby joining effector cells to target cells. In some embodiments, two or more different binding moieties are provided, each independently selected from the above binding moieties.

As with the prior aspect, the effector cells can be further engineered to increase expression of an exogenous compound, optionally Interleukin 2, to promote growth, proliferation or persistence of the effector cells.

In another related aspect, a method of assessing cytolysis of cancer cells is provided, which includes providing a cell-substrate impedance monitoring device operably connected to an impedance analyzer, wherein the device comprises a well for receiving cells and an electrode array at a base of the well; adding target cells characterized as cancer cells to the well; adding effector cells to the well, wherein the effector cells are immune cells, optionally from a same patient as the target cells; adding a bispecific engager to the well to form a test well, wherein the bispecific engager is a molecule configured to bridge the effector cells to the target cells, such as by binding surface antigens; monitoring cell-substrate impedance of the test well over time, including before and after the step of adding the bispecific engager, and optionally deriving impedance-based parameters from the impendences; and determining the effectiveness of effector cell killing in response to the bispecific engager by comparing the impedances or impedance based parameters over time. The bispecific engager preferably includes two polypeptides linked together, wherein each polypeptide binds either effector cells or the target cells, thereby bridging the effector cells and the target cells.

In some embodiments the target cells are circulating tumor cells (CTCs) collected from blood or tumor cells, optionally collected from a tissue biopsy. In some embodiments the cancer cells are obtained from a biological sample selected from the group consisting of a solid tumor, a haematopoietic tumor, blood, and pleural effusion.

In some embodiments, the effector cells are selected from one or more of natural killer cells (NK cells), macrophages, neutrophils, eosinophils, T-cells, and B-cells. Furthermore, the T cells can be selected from one or more of the group consisting of T helper cells (Th cells), cytotoxic T cells, and memory T cells.

The bispecific engager preferably includes two polypeptides linked together, wherein each polypeptide binds either the effector cells or the target cells thereby bridging the effector cells and the target cells. In some embodiments the bispecific engager binds a T-cell surface moiety, optionally cluster of differentiation 3 (CD3).

As with the other aspects, the impedance based parameter can be a cell index or a normalized cell index that is normalized to a time point before adding the bispecific engager. The impedance based parameter can be a cell change index. The impedance based parameter can be an impedance-based curve. Effectiveness of effector cell killing of target cells can be determined by comparing impedance-based curves over time. Typically, a decreasing impedance or impedance based parameter is indicative of increased effectiveness. The effectiveness of effector cell killing of target cells can also be determined by calculating and comparing percent cytolysis of the target cells. Percent cytolysis can be derived from cell index and thus impedance. Further, cell-substrate impedance can be used to determine the IC50 of bispecific engagers for comparison to one another.

The assay can be performed in a single well; however, in other embodiments the method includes adding the target cells to a second well of the device designated a control well, adding a negative control compound or isotype control to the control well that does not join effector cells to target cells, monitoring impedance of the control well and optionally deriving an impedance-based parameter from the impedance of the control well; and comparing the impedances or impedance based parameters over time between the control well and test well to determine whether adding the bispecific engager increases effector cell killing of target cells.

Accordingly a method of determining a treatment for killing of tumor cells in a patient is also provided, which includes collecting a sample of cancer cells and a sample of effector cells from a same patient; assessing the cytolytic activity of effector cells in response to a one or more different bispecific engagers substantially as set forth herein; and designating the bispecific engager determined to be effective at improving effector cell killing of cancer cells to be a treatment for the killing of cancer cells in the patient.

In another related aspect of the invention, a method of assessing cytolysis of cancer cells is provided, which includes providing a cell-substrate impedance monitoring device operably connected to an impedance analyzer, wherein the device comprises a well for receiving cells and an electrode array at a base of the well; adding one or more target cells characterized or designated as cancer cells to the well; adding an oncolytic virus to the well to form a test well, wherein the virus is suspected of recognizing and lysing cancer cells; monitoring cell-substrate impedance of the test well before and after adding the oncolytic virus and optionally deriving impedance-based parameters from the impedances; and determining effectiveness of target cell lysis by comparing the impedances or impedance based parameters derived from the impedances over time.

As with the above related aspects, the high-resolution of the device resolves differences in impedance resulting from death of fewer than all of the target cells received in the well. For example, lysis of fewer than 50% of the target cells received in the well can be easily resolved and in other embodiments lysis of fewer than 10% of the target cells received in the well can be resolved.

Target cells embodied as cancer cells can be obtained from a variety of biological samples. Among these include a solid tumor, a haematopoietic tumor, blood, and pleural effusion. In some embodiments, the target cells are circulating tumor cells (CTCs) collected from blood. In other embodiments, the target cells are tumor cells collected from a tissue biopsy. In some embodiments, the target cells are of a tumor cell line.

When determining and measuring impedance-based parameters, preferably only a single parameter is needed. In some instances the impedance based parameter is a cell index or a normalized cell index that is normalized to a time point before adding the virus. Typically, impedances or impedance based parameters decreasing over time is indicative of increased effectiveness. In some embodiments, the impedance based parameter is an impedance based curve such as a cell index curve or a normalized cell index curve over time. In some embodiments, the effectiveness of target cell lysis is determined by calculating a percent cytolysis of the target cells.

Accordingly, a method of determining a treatment for killing of cancer cells in a patient is provided, which includes collecting a sample of cancer cells from a patient; assessing the cytolytic activity of one or more oncolytic virus strains on the cancer cells substantially as set for the above; and designating the oncolytic virus determined to be effective at the killing of cancer cells in the patient to be a treatment for the killing of tumor cells in the patient.

BRIEF DESCRIPTION OF THE DRAWINGS

FIG. 1A depicts a substrate 101 having 16 electrode arrays (or 16 electrode structure units) 102 that are arranged in a 2-row by 8-column configuration on a substrate. FIG. 1B is a higher resolution image depicting a single electrode array of a device having two electrode structures 106, each comprised of a plurality of interdigitated electrode elements 105. FIG. 1C shows a schematic drawing of an interdigitated electrode array, illustrating the requirement of approximately uniform distribution of electrode resistance across the array by having a same surface area.

In FIG. 19A, increasing numbers of NIH3T3 ranging from 100 cells all the way up to 10,000 cells were seeded in a cell-substrate impedance monitoring device and the cells were monitored for 10 hours at which point the Cell Index was obtained. The Cell Index value was plotted against the corresponding number of cells. In FIG. 19B, the cells described in FIG. 19A were assayed by MTT assay at the end of the experiment and the optical density at 590 nm was plotted against the number of cells seeded.

In FIG. 20A, human alveolar basal epithelial cells (A549 cells) were seeded in a cell-substrate monitoring device at a density of 10,000 cells per well and the cells were continuously monitored up to 24 hours at which point paclitaxel was added at the indicated final concentrations. In FIG. 20B, Annexin V staining of A549 cells treated with DMSO or 12.5 nM paclitaxel for 20 hours. The cells were observed with fluorescence microscope and images were captured with an attached digital camera.

In FIG. 21B, A549 cells growing on tissue culture dishes for 20 hours were treated with DMSO or 100 µM Olomoucine. Cell cycle analysis was performed by flow cytometry.

In FIG. 25A, dynamic monitoring of NK-cell mediated cytolysis of NIH 3T3 cells (target cells) is shown. The NIH 3T3 cells were seeded in the wells of the 96-well e-plate at 5000 cells/well, and cell attachment, spreading and proliferation were monitored in real time. 34 hours after seeding of the cells, Cell Index (CI) values reached 3, which is equivalent to approximately 10,000 cells/well. 150,000 mNK cells (effector cells) or YAC cells (control effector cells) which function as the negative control were added to each well in triplicates. The mNK cell-mediated cytolysis was then dynamically monitored. In FIG. 25B, Time-dependent cytolytic activity of mNK cells for different ratios of E/T (effector cell number: target cell number) is shown. The cytolytic activity at a given time point was calculated and presented as the percentage of cytolysis, or percent cytolysis {% of cytolysis= $(CI_{no\ effector} - CI_{effector})/CI_{no\ effector} \times 100$}, where $CI_{effector}$ and $CI_{no\ effector}$ were cell indexes for wells with and without added effector cells, respectively at the time point of interest. For calculation of percent cytolysis shown here, normalized cell index values were used for CI. In general, cell index values or normalized cell index values may be used in the calculation of percentage of cytolysis, or percent cytolysis.

In FIG. 26A, quantitative measurement of cytolytic activity of mNK cells is shown. The NIH 3T3 cells were seeded to the 96-well e-plate. Cell growth was monitored in real time on the RT-CES system until the CI values reached 3, equivalent to 10,000 cells/well. The mNK cells (effector cells) were added to target cells at different cell concentrations, making a series of E/T ratios (effector cell number to target cell number) as indicated. The cytolysis of the target cells at different E/T ratios was dynamically monitored on the RT-CES system. The normalized Cell Index was used, in which the Cell Index values obtained from post addition of mNK cells were normalized against the Cell Index value from the same well shortly-before the addition of mNK cells. In FIG. 26B, time-dependent cytolytic activity of mNK cells at different E/T ratios is shown. The percentage of cytolysis, or percent cytolysis, of the NIH 3T3 cells by mNK cells was calculated according to the equation, {percentage of cytolysis= $(NCI_{no\ effector} - NCI_{effector})/NCI_{no\ effector} \times 100$}, where $NCI_{effector}$ and $NCI_{no\ effector}$ were normalized cell indexes for wells with and without added effector cells, respectively at the time point of interest. The time dependent cytolytic activities are indicated. In FIG. 25C, quantitative measurement of cytolytic activity of NK92 cells is shown. The target cells, MCF7 were seeded as described and the cell growth was monitored on the RT-CES system as described above. The NK92 cells were then added to each well at different concentration making the series of E/T ratios as indicated. The cytolytic activities of NK92 cells on MCF7 cells at different E/T ratios were dynamically monitored on the RT-CES system. In FIG. 26D, time-dependent cytolytic activity of NK92 cells at different E/T ratios is shown. The percentage of cytolysis of the MCF7 cells by NK 92 cells was calculated as described in FIG. 26B, and was indicated.

In FIG. 27A, the NK92-mediated cytolysis of 7 different cancer lines is provided. The percentage of cytolysis indicated for each line is calculated based on the Cell Index value of individual wells after 8 hours of addition of NK92 cells, which showed the maximum cytolysis. FIG. 27B shows mNK-mediated cytolysis of 9 different cell lines. The percentage of cytolysis indicated for each line is calculated based on the Cell Index values of individual wells after 12 hours of addition of mNK cells, which showed the maximum cytolysis.

In FIG. 28A, the interaction of adherent target cells with the sensor microelectrodes in the bottom of the well leads to the generation of impedance signal which is displayed as an arbitrary unit called cell index (CI). In FIG. 28B, the addition of suspended effector cells are not detected by the sensor, since these cells do not adhere to the bottom of the well. In FIG. 27C, effector-mediated cytolysis of target cells is detected by the sensor due to morphological changes of target cells and the loss of interaction of target cells with the microelectrodes in the bottom of the well upon cytolysis.

In FIG. 29A, 10,000 human alveolar basal epithelial cells (A549 cells) target cells were seeded in the wells of E-plates. At the indicated time point (arrow), NK-92 cells were added at different E/T ratios and the viability of A549 cells were dynamically monitored every 15 minutes using the RT-CES system. FIG. 29B depicts a comparison of RT-CES readout with MTT at 25 hours after addition of NK-92 cells. The A549 cells described in FIG. 29A were washed and cell viability was assessed using MTT. For each E/T ratio the normalized CI value obtained by RT-CES is plotted together with the absorbance value obtained using MTT assay. In FIG. 29C both the RT-CES readout and MTT assay the percent cytolytic activity of NK-92 cells at different E/T ratios was calculated using the formula as described in materials and methods section.

In FIG. 31A, A549 cells were seeded in the wells of E-plates. Twenty four hours after seeding NK-cells at a density of 16:1 (E/T ratio) were pre-incubated with the different concentrations of the MEK inhibitor PD 98059 for thirty minutes and then added to A549 cells at the indicated time point (arrow). The viability of A549 cells were continually monitored using the RT-CES system. In FIG. 31B, the extent of NK-92 mediated cytolytic activity in the presence of MEK inhibitor was calculated at the indicated times post-NK addition as described in materials and methods section. In FIG. 31C, the effect of PI3 Kinase inhibitor Wortmannin on NK-92 mediated cytolysis of A549 cells is shown. The cells were treated with the inhibitor as described for FIG. 31A. In FIG. 31D, percent cytolytic activity of NK-92 cells was calculated at the end of the experiment described for FIG. 31C.

FIG. 33A depicts flow cytometer analysis of EpCAM surface expression in PC3, MCF7 and HeLa cancer cell lines. EpCAM surface expression is evaluated in three different cancer cell lines using a PE-conjugated anti human CD326(EpCAM) antibody (dark gray area). The medium gray shadowed area identifies the signal of the negative isotype control antibody, while the light gray area denotes the autofluorescence of unstained cells. In FIG. 33B, three cancer cell lines with different level of EpCAM surface expression were seeded at the same density and treated with the same amount of EpCAM/CD3 BiTE antibody and PBMCs. The decline in cell index due to immune cell-mediated cell killing is proportional to the amount of EpCAM expression across the three cell lines. In FIG. 33C, baseline plotting normalizes CI variations across multiple cell lines and reveal cell killing efficiency in relation to antigen expression and effector cells amount. CI was normalized for each group replicate (1 µg/ml EpCAM BiTE) using a baseline subtraction of the correspondent control groups (No PBMCs). Different amounts of PBMCs:Cancer cells ratio are indicated by gradations of the same color. The thick gray horizontal line corresponds to No PBMCs controls that were used as baselines In FIG. 33D, effective Time for 50% cell killing (ET50) as function of effector:target ratio for the three different cancer cell lines treated with 1 µg/ml EpCAM/CD3 BiTE antibody. Effective Time for 50% cell killing (ET50) as function of effector:target ratio for the three different cancer cell lines treated with 1 µg/ml EpCAM/CD3 BiTE antibody.

DETAILED DESCRIPTION

Figure 1A:
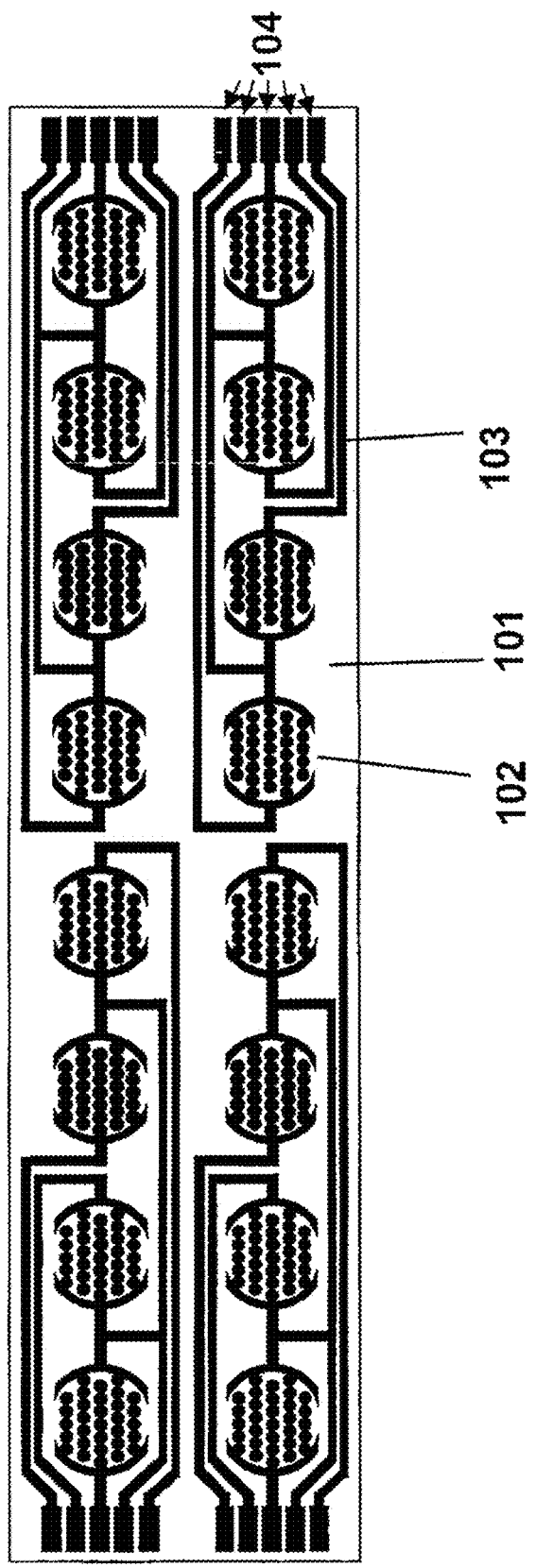
FIGS. 1A-C depict configurations of cell-substrate impedance measurement devices having an interdigitated electrode array.

As an introduction, the invention provides methods of determining the effectiveness of proposed anticancer therapeutics by adding the proposed therapeutics to a population of cancer cells collected from a patient and monitoring the effect on the cancer cell population over time using cell-substrate impedance monitoring. The methods are adapted for therapeutics embodied in various forms such as anticancer compounds that operate independently on cancer cells or together with effector cells, engineered immune cells, oncolytic viruses and combinations thereof. By determining the effectiveness of cancer cell killing, the methods further identify treatments for use in cancer patients.

A. Definitions

For clarity of disclosure, and not by way of limitation, the detailed description of the invention is divided into the subsections that follow. Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "membrane" is a sheet of material.

When a suspension of viable, unimpaired, cancer cells is added to a well, a surface of the well "is suitable for cell attachment" when a significant percentage of the cells are adhering to the surface of the well within twelve hours. Preferably, at least 50% of the cells are adhering to the surface of the well within twelve hours. More preferably, a surface that is suitable for cell attachment has surface properties so that at least 70% of the cells are adhering to the surface within twelve hours of plating (i.e., adding cells to the well). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating. To have desired surface properties for cell attachment, the surface may need to chemically-treated (e.g. treatment with an acid and/or with a base), and/or physically treated (e.g. treatment with plasma), and/or biochemically treated (e.g. coated with one or more molecules or biomolecules that promotes cell attachment). In the present invention, a biocompatible surface (such as a membrane) preferably is suitable for the attachment of cells of the type that are to be used in an assay that uses the biocompatible surface (e.g., membrane), and most preferably, allows the attachment of at least 90% of the cells that contact the biocompatible surface during the assay.

An "electrode" is a structure having a high electrical conductivity, that is, an electrical conductivity much higher than the electrical conductivity of the surrounding materials.

As used herein, an "electrode structure" refers to a single electrode, particularly one with a complex structure (as, for example, a spiral electrode structure), or a collection of at least two electrode elements that are electrically connected together. All the electrode elements within an "electrode structure" are electrically connected.

As used herein, "electrode element" refers to a single structural feature of an electrode structure, such as, for example, a fingerlike projection of an interdigitated electrode structure.

As used herein, an "electrode array" or "electrode structure unit" is two or more electrode structures that are constructed to have dimensions and spacing such that they can, when connected to a signal source, operate as a unit to generate an electrical field in the region of spaces around the electrode structures. Preferred electrode structure units of the present invention can measure impedance changes due to cell attachment to an electrode surface. Non-limiting examples of electrode structure units are interdigitated electrode structure units and concentric electrode structure units. In some embodiments the "electrode array" includes a small measuring electrode and a large reference electrode, which directs the impedance measurement to the small measuring electrode.

An "electrode bus" is a portion of an electrode that connects individual electrode elements or substructures. An electrode bus provides a common conduction path from individual electrode elements or individual electrode substructures to another electrical connection. In the devices of the present invention, an electrode bus can contact each electrode element of an electrode structure and provide an electrical connection path to electrical traces that lead to a connection pad.

"Electrode traces" or "electrically conductive traces" or "electrical traces", are electrically conductive paths that extend from electrodes or electrode elements or electrode structures toward one end or boundary of a device or apparatus for connecting the electrodes or electrode elements or electrode structures to an impedance analyzer. The end or boundary of a device may correspond to the connection pads on the device or apparatus.

A "connection pad" is an area on an apparatus or a device of the present invention which is electrically connected to at least one electrode or all electrode elements within at least one electrode structure on an apparatus or a device and which can be operatively connected to external electrical circuits (e.g., an impedance measurement circuit or a signal source). The electrical connection between a connection pad and an impedance measurement circuit or a signal source can be direct or indirect, through any appropriate electrical conduction means such as leads or wires. Such electrical conduction means may also go through electrode or electrical conduction paths located on other regions of the apparatus or device.

"Interdigitated" means having projections coming one direction that interlace with projections coming from a different direction in the manner of the fingers of folded hands (with the caveat that interdigitated electrode elements preferably do not contact one another).

As used herein, a "high probability of contacting an electrode element" means that, if a cell is randomly positioned within the sensor area of a device or apparatus of the present invention, the probability of a cell (or particle) contacting on an electrode element, calculated from the average diameter of a cell used on or in a device or apparatus of the present invention, the sizes of the electrode elements, and the size of the gaps between electrode elements, is greater than about 50%, more preferably greater than about 60%, yet more preferably greater than about 70%, and even more preferably greater than about 80%, greater than about 90%, or greater than about 95%.

As used herein, "electrodes (or electrode structures) have substantially the same surface area" means that the surface areas of the electrodes referred to are not substantially different from each other, so that the impedance change due to cell attachment or growth on any one of the electrodes (or electrode structures) referred to will contribute to the overall detectable change in impedance to a same or similar degree as the impedance change due to cell attachment or growth on any other of the electrodes (or electrode structures) referred to. In other words, where electrodes (or electrode structures) have substantially the same surface area, any one of the electrodes can contribute to overall change in impedance upon cell attachment or growth on the electrode. In most cases, the ratio of surface area between the largest electrode and the smallest electrode that have "substantially the same surface area" is less than 10. Preferably, the ratio of surface area between the largest electrode and the smallest electrode of an electrode array is less than 5, 4, 3, 2, 1.5, 1.2 or 1.1. More preferably, the at least two electrodes of an electrode structure have nearly identical or identical surface area.

As used herein, "the device has a surface suitable for cell attachment or growth" means that the electrode and/or non-electrode area of the apparatus has appropriate physical, chemical or biological properties such that cells of interest can viably attach on the surface and new cells can continue to attach, while the cell culture grows, on the surface of the apparatus. However, it is not necessary that the device, or the surface thereof, contain substances necessary for cell viability or growth. These necessary substances, e.g., nutrients or growth factors, can be supplied in a medium. Preferably, when a suspension of viable, unimpaired, epithelial or endothelial cells is added to the "surface suitable for cell attachment" when at least 50% of the cells are adhering to the surface within twelve hours. More preferably, a surface that is suitable for cell attachment has surface properties so that at least 70% of the cells are adhering to the surface within twelve hours of plating (i.e., adding cells to the chamber or well that comprises the said device). Even more preferably, the surface properties of a surface that is suitable for cell attachment results in at least 90% of the cells adhering to the surface within twelve hours of plating. Most preferably, the surface properties of a surface that is suitable for cell attachment results in at least 90% of the cells adhering to the surface within eight, six, four, two hours of plating.

As used herein, "detectable change in impedance between or among electrodes" (or "detectable change in impedance between or among electrode structures") means that the impedance between or among said electrodes (or electrode structures) would have a significant change that can be detected by an impedance analyzer or impedance measurement circuit when molecule binding reaction occurs on the electrode surfaces. The impedance change refers to the difference in impedance values when molecule binding reaction occurs on the electrode surface of the apparatus and when no molecular reaction occurs on the electrode surface. Alternatively, the impedance change refers to the difference in impedance values when cells are attached to the electrode surface and when cells are not attached to the electrode surface, or when the number, type, activity, adhesiveness, or morphology of cells attached to the electrode-comprising surface of the apparatus changes. In most cases, the change in impedance is larger than 0.1% to be detectable. Preferably, the detectable change in impedance is larger than 1%, 2%, 5%, or 8%. More preferably, the detectable change in impedance is larger than 10%. Impedance between or among electrodes is typically a function of the frequency of the applied electric field for measurement. "Detectable change in impedance between or among said electrodes" does not require the impedance change at all frequencies being detectable. "Detectable change in impedance between or among said electrodes" only requires a detectable change in impedance at any single frequency (or multiple frequencies). In addition, impedance has two components, resistance and reactance (reactance can be divided into two categories, capacitive reactance and inductive reactance). "Detectable change in impedance between or among said electrodes" requires only that either one of resistance and reactance has a detectable change at any single frequency or multiple frequencies. In the present application, impedance is the electrical or electronic impedance. The method for the measurement of such impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. Measurement of such electric impedance is an electronic or electrical process that does not involve the use of any reagents.

As used herein, "said at least two electrodes have substantially different surface area" means that the surface areas of any electrodes are not similar to each other so that the impedance change due to cell attachment or growth on the larger electrode will not contribute to the overall detectable impedance to a same or similar degree as the impedance change due to cell attachment or growth on the smaller electrodes. Preferably, any impedance change due to cell attachment or growth on the larger electrode is significantly smaller than the impedance change due to cell attachment or growth on the smaller electrode. Ordinarily, the ratio of surface area between the largest electrode and the smallest electrode is more than 10. Preferably, the ratio of surface area between the largest electrode and the smallest electrode is more than 20, 30, 40, 50 or 100.

As used herein, "multiple pairs of electrodes or electrode structures spatially arranged according to wells of a multi-well microplate" means that the multiple pairs of electrodes or electrode structures of a device or apparatus are spatially arranged to match the spatial configuration of wells of a multi-well microplate so that, when desirable, the device can be inserted into, joined with, or attached to a multiwell plate (for example, a bottomless multiwell plate) such that multiple wells of the multi-well microplate will comprise electrodes or electrode structures.

As used herein, "arranged in a row-column configuration" means that, in terms of electric connection, the position of an electrode, an electrode array or a switching circuit is identified by both a row position number and a column position number.

As used herein, "each well contains substantially same number . . . of cells" means that the lowest number of cells in a well is at least 50% of the highest number of cells in a well. Preferably, the lowest number of cells in a well is at least 60%, 70%, 80%, 90%, 95% or 99% of the highest number of cells in a well. More preferably, each well contains an identical number of cells.

As used herein, "dose-response curve" means the dependent relationship of response of cells on the dose concentration of a proposed therapeutic compound. The response of cells can be measured by many different parameters. For example, a compound is suspected to have cytotoxicity and cause cell death. Then the response of cells can be measured by percentage of non-viable (or viable) cells after the cells are treated by the test compound. Plotting this percentage of non-viable (or viable) cells as a function of the dose concentration of the test compound constructs a dose response curve. In the present application, the percentage of non-viable (or viable) cells can be expressed in terms of measured impedance values, or in terms of cell index derived from impedance measurement, or in terms of cell change indexes. For example, for a give cell type and under specific cellular physiological condition (e.g., a particular cell culture medium), cell index can be shown to have a linear correlation or positive correlation with the number of viable cells in a well from which cell index was derived from the impedance measurement. Thus, in the present application, one can plot cell index as a function of the dose concentration of the test compound to construct a "dose-response curve". Note that, generally, cell index not only correlate with the number of viable cells in the wells but also relate to the cell morphology and cell attachment. Thus plotting cell index versus doss concentration provides information not only about number of cells but also about their physiological status (e.g. cell morphology and cell adhesion). Furthermore, an important advantage offered by the system and devices of the present application is that in a single experiment, one can obtain "dose-response curves" at multiple time points since the system allows for the continuous monitoring of cells and provides impedance measurement at many time points over a time range as short as a few minutes to as long as days or weeks.

A "compound" or "proposed therapeutic compound" is any compound whose activity or direct or indirect effect or effects on cells is investigated in the assay. A test compound can be any compound, including, but not limited to, a small molecule, a large molecule, a molecular complex, an organic molecule, an inorganic molecule, a biomolecule such as but not limited to a lipid, a steroid, a carbohydrate, a fatty acid, an amino acid, a peptide, a protein, a nucleic acid, or any combination of these. A test compound can be a synthetic compound, a naturally occurring compound, a derivative of a naturally-occurring compound, etc. The structure of a test compound can be known or unknown. In one application of the present invention, a compound is capable of, or is suspected of, inducing cytolysis. In another application of present invention, a compound is capable of, or is suspected of, stimulating effector cells. A "compound" can include two polypeptides linked together to form a bispecific engager, where one polypeptide binds an effector cell (e.g. CD3 on a T-cell) and the other a target cell thereby joining effector cells to target cells. In still another application, a compound is capable of, or is suspected of, interacting with cells (for example, binding to cell surface receptor, or inhibiting certain intracellular signal transduction pathway, or activating cells).

A "known compound" is a compound for which at least one activity is known. In the present invention, a known compound preferably is a compound for which one or more direct or indirect effects on cells is known. Preferably, the structure of a known compound is known, but this need not be the case. Preferably, the mechanism of action of a known compound on cells is known, for example, the effect or effects of a known compound on cells can be, as nonlimiting examples, effects on cell viability, cell adhesion, apoptosis, cell differentiation, cell proliferation, cell morphology, cell cycle, IgE-mediated cell activation or stimulation, receptor-ligand binding, cell number, cell quality, cell cycling, etc.

An "impedance value" is the impedance measured for electrodes in a well with or without cancer cells present. Impedance is generally a function of the frequency, i.e., impedance values depend on frequencies at which the measurement was conducted. For the present application, impedance value refers to impedance measured at either single frequency or multiple frequencies. Furthermore, impedance has two components, one resistance component and one reactance component. Impedance value in the present application refers to resistance component, or reactance component, or both resistance and reactance component. Thus, when "impedance value" was measured or monitored, we are referring to that, resistance, or reactance, or both resistance and reactance were measured or monitored. In many embodiments of the methods of the present application, impedance values also refer to parameter values that are derived from raw, measured impedance data. For example, cell index, or normalized cell index, or delta cell index could be used to represent impedance values.

A "Cell Index" or "CI" is a parameter that can derived from measured impedance values and that can be used to reflect the change in impedance values. There are a number of methods to derive or calculate Cell Index.

A "Normalized Cell Index" at a given time point is calculated by dividing the Cell Index at the time point by the Cell Index at a reference time point. Thus, the Normalized Cell Index is 1 at the reference time point.

A "delta cell index" at a given time point is calculated by subtracting the cell index at a standard time point from the cell index at the given time point. Thus, the delta cell index is the absolute change in the cell index from an initial time (the standard time point) to the measurement time.

A "Cell Change Index" or "CCI" is a parameter derived from Cell Index and "CCI" at a time point is equal to the $1^{st}$ order derive of the Cell Index with respect to time, divided by the Cell Index at the time point.

As used herein, "cytolytic activity" refers to the ability of effector cells to lyse or kill target cells. For a given ratio of effector cell number to target cell number and for a specific time period after addition of effector cells to target cells, if effector cells of a first type kills more target cells than effector cells of a second type, then the effector cells of the first type have higher cytolytic activity. There are various parameters that can be determined and be used to indicate or quantify cytolytic activity of effector cells. For example, viability of target cells at a time point after effector cells are added to target cells in a well can be used to indicate the cytolytic activity of the effector cells. A low viability of target cells indicates that many target cells have been killed by the effector cells and shows that the effector cells have high cytolytic activity. In another example, percent cytolysis (or percentage of cytolysis) of target cells at a time point after effector cells are added to target cells can also be used to indicate the cytolytic activity. A low percent cytolysis indicates that few target cells have been killed by the effector cells and show that the effector cells have low cytolytic activity.

As used herein, "target cell" or "target cells" refers to any cell that can be lysed or killed by the effector cells. Non-limiting examples of target cells include cancer cells, cancer cell lines, and cells isolated from cancerous tissues. In the assay for measuring cytolytic activity of effector cells, one is interested in how many target cells or what percentage of target cells have been killed by the effector cells. Thus, the quantity of target cells, or the viability of the target cells may be determined at any time point during an assay.

As used herein, "effector cell" or "effector cells" refer to any cells that are capable of killing or lysing target cells, such as Natural Killer (NK) cells, Cytotoxic T-Lymphocytes (CTLs), neutrophils, easonophils, macrophages, Natural Killer T (NKT) cells, B-cells, T-cells, a cell type having cytolytic activity, a CAR-T cell and others.

As used herein, "viability" refers to quantity of, or percentage of viable cells that are alive and have not undergone cytolysis. In the assay for measuring cytolytic activity of effector cells, one may need to determine viability of target cells at some time point(s) after effector cells have been added to target cells in order to determine how many target cells or what percentage of target cells are killed or lysed by the effector cells. In one embodiment of a method of the present invention, target cells are introduced in wells comprising electrode arrays, which are used to measure cell-substrate impedance for quantifying the number of target cells. Impedance of a well containing target cells is measured prior to and after addition of effector cells to the wells. In one approach, viability of target cells at a time point after addition of effector cells may be determined by comparing the impedance of the well prior to and after addition of effectors. Viability of target cells may be calculated as the ratio of the impedance of the well at the time point of interest to the impedance of the well immediately prior to addition of effector cells. Such a calculation has an implicit assumption that the impedance of the well may be approximately proportional to the number of the viable cells in the well. Here for the time period from the time point of addition of effector cells to the time point of interest, it is assumed that there is little or no proliferation of target cells. Thus, the ratio of impedance of the well at the time point of interest to the impedance of the well immediately prior to addition of effector cells reflects the percentage of the initial cells (the viable cells immediately prior to addition of effector cells) which are still viable at the time point of interest. In another approach, viability of target cells at a time point after addition of effector cells may be determined by comparing the cell index of the well prior to and after addition of effector cells. Viability of target cells may be calculated as the ratio of the cell index of the well at the time point of interest to the cell index of the well immediately prior to addition of effector cells. Such a calculation has an implicit assumption that the cell index of the well may be approximately proportional to the number of the viable cells in the well. For such a calculation of viability of target cells, cell index may be normalized cell index. In still another approach, viability of target cells in a test well at a time point after addition of effector cells may be determined by comparing the impedance (or cell index) of the well at the time point of interest to the impedance (or cell index) of a control well to which same number of target cells and no effector cells are added. Viability of target cells at a time point after adding effector cells may be calculated as the ratio of the impedance (or cell index) of the test well at the time point of interest to the impedance (or cell index) of the control well at the same time point. Such a calculation of viability of target cells in a test well has an implicit assumption that if there is no killing or lysis of target cells by effector cells, the impedance or cell index of the test well would be the same as that of the control well. For such calculation of viability of target cells, cell index may be normalized cell index.

As used herein, "primary cell" or "primary cells" refers to any non-immortalized cell that has been derived from various tissues and organs of a patient or an animal.

As used herein, "cell or cells having cytolytic activity" refers to any cell that is capable of killing or lysing target cells. Cell or cells having cytolytic activity are effector cells.

As used herein, "antibody-dependent cellular cytotoxicity (ADCC)" refers to the killing of target cells (or cytotoxicity of target cells) by effector cells, where target cells have been marked by an antibody.

The term "therapeutically effective amount" is defined as the amount of a compound or pharmaceutical composition that will elicit the biological or medical response of a tissue, system, animal or human, that is being sought by the researcher, medical doctor or other clinician.

The term "potency" is defined in accordance with the U.S. Pharmacopeia (USP) and refers to the quantity of an active pharmaceutical component in the composition. In accordance with the requirements of the USP, the potency that is required of the corticotropin compositions described below is not less than 80.0 percent and not more than 125.0 percent of the potency stated on the label in USP corticotropin units.

The term "USP unit" refers to a unit used to measure the mass of a vitamin or drug based on its expected biological effects. For each substance to which this unit applies, the U.S. Pharmacopeia has determined the biological effect associated with a dose of 1 USP unit. As such, quantities of the substance can be expressed in terms of this standard unit, which, in most cases, is equal to the international unit (IU). For example, 1 USP unit of synthetic porcine corticotropin equals approximately 10 micrograms, which equals 0.01 mg.

The term "pharmaceutically acceptable" when used to describe a carrier, whether diluent or excipient, is defined as being compatible with the other ingredients of the formulation and not deleterious to the recipient thereof.

The terms "administration of a composition" or "administering a composition" are defined to include the act of providing a compound or pharmaceutical composition of the invention to the subject in need of treatment.

B. Cell-Substrate Impedance Monitoring Devices and Systems

Cell-substrate impedance monitoring is performed using a cell-substrate impedance-monitoring device operably connected to an impedance analyzer. The device has one or more wells. Each well for impedance monitoring has an electrode array at its base and is configured for receiving cells. When cancer cells are added to the wells they attach to the electrodes and act as insulators, which increases the impedance within the well. As the cells grow and continue to cover the electrodes, the current is impeded in manner related to the number of cells covering the electrode, the morphology of the cells and the nature of the attachment. When cancer cells are disrupted, such as by the presence of a toxic compound or immune cells that act against the cell, accompanying changes in cell morphology and/or attachment alter the impedance. The impedance or an impedance-based parameter (e.g. cell index, normalized cell index or cell change index) calculated from the impedance can be plotted overtime and used to predict the effectiveness of the compound or immune cell against the cancer cell phenotype. As such, potential therapeutics, whether compounds or engineered immune cells can be assessed using cell-substrate impedance technology.

Figure 1B:
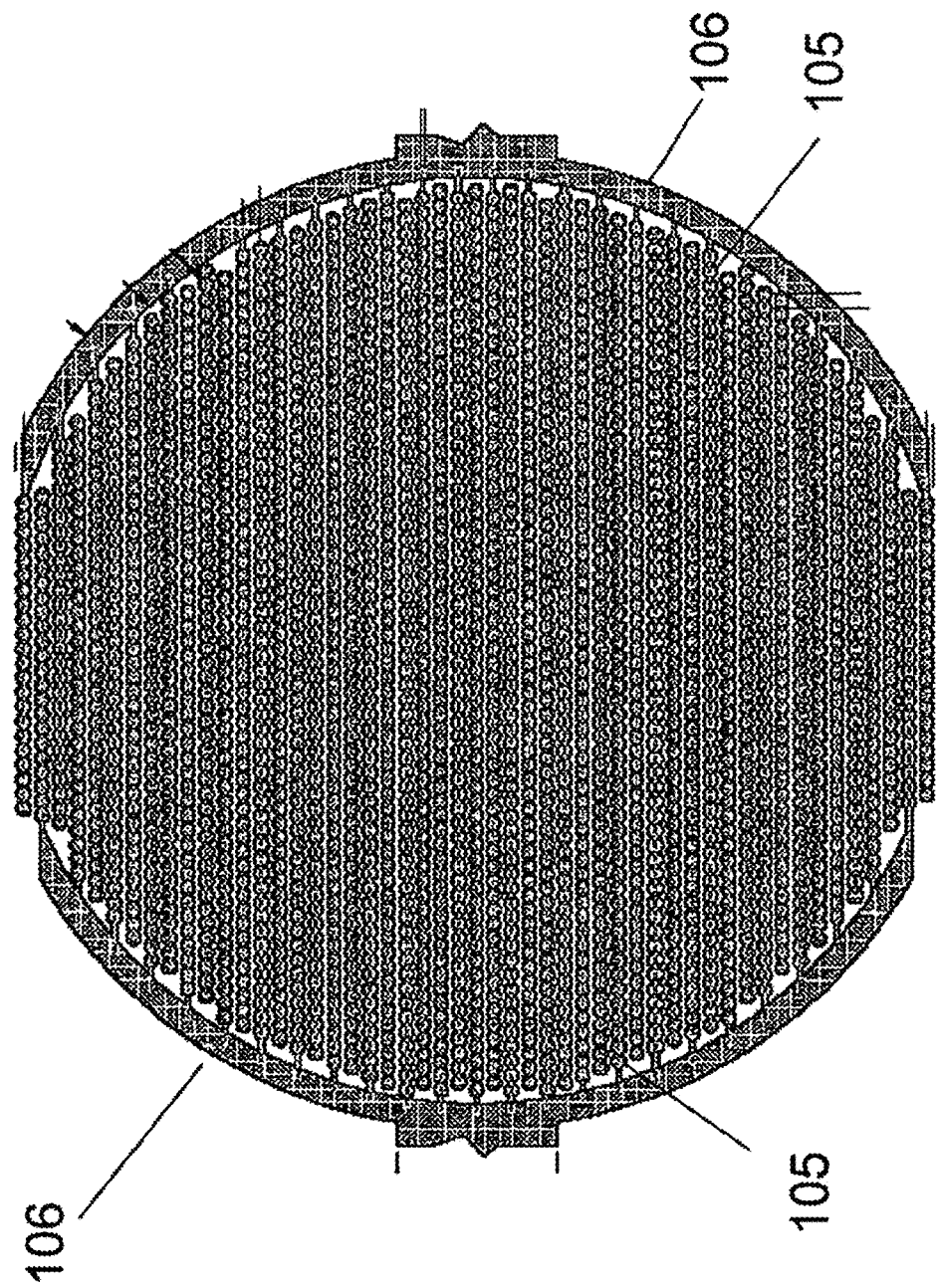
Figure 1C:
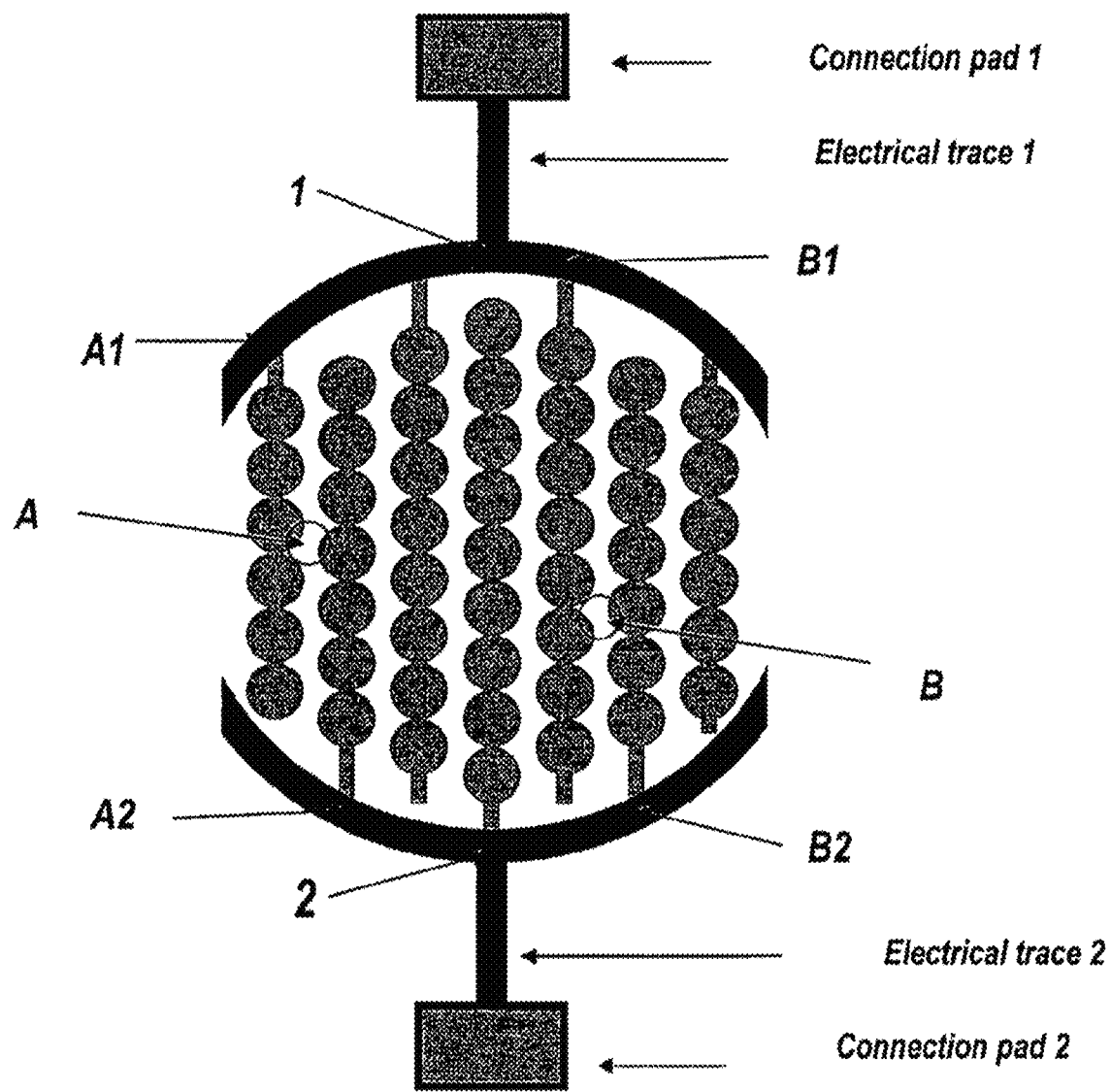

Electrode arrays can be provided in different structural configurations. In some embodiments, the electrode arrays can follow those developed by Gaiver and Keese, where a plurality of small measuring electrodes share a large reference electrode, and where the impedance measurement is directed to the small measuring electrodes. These configurations may be acceptable when large numbers of cancer cells are added to the wells or after cells are grown to confluence. In configurations where higher resolution is needed, such as when fewer than 100 cells are added to wells, the electrode arrays can be configured as interdigitated electrode arrays substantially as shown in FIGS. 1A-C and described herein.

Figure 2:
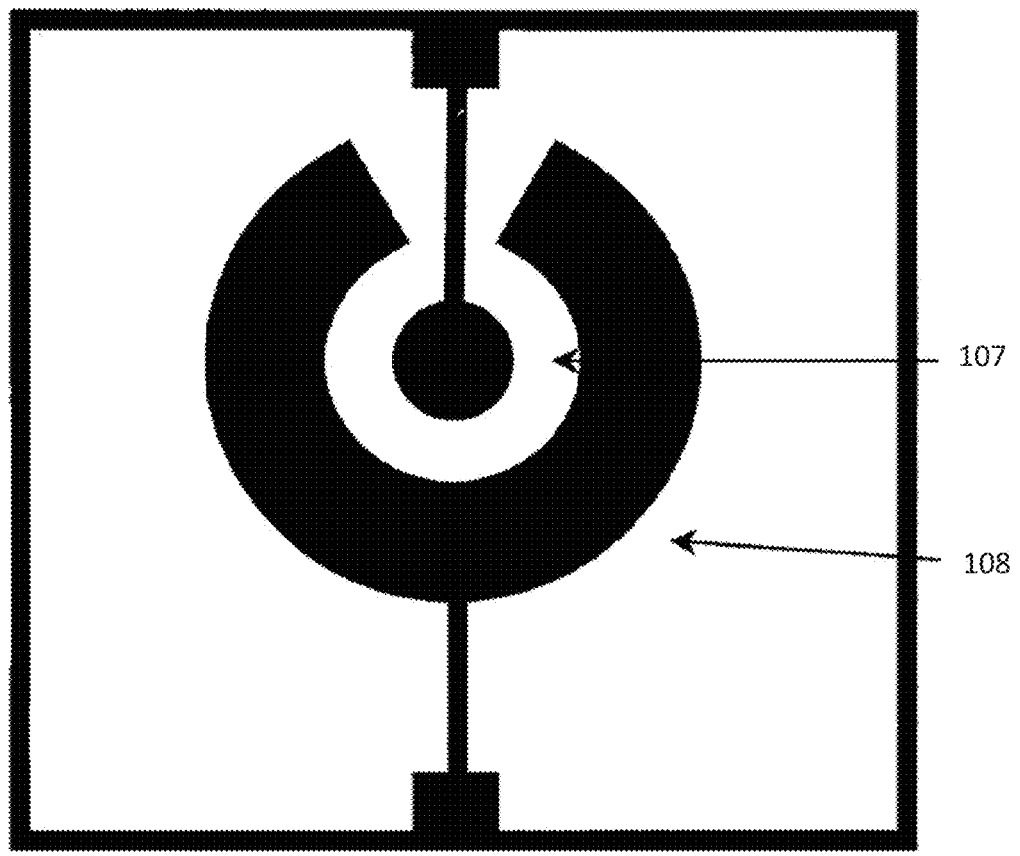
FIG. 2 depicts a configuration of a cell-substrate impedance measurement device having a single measuring electrode 107 and a single reference electrode 108.

Another high-resolution embodiment is shown in FIG. 2, which includes a single small measurement electrode and a much larger reference electrode. By providing a comparatively small measuring electrode, the impedance measurement across of the entire array is directed almost entirely to the single measuring electrode. This configuration has been found to have extremely high sensitivity, which is useful when working with very few target cells, such as ten cells or fewer, nine cells or fewer, eight cells or fewer, seven cells or fewer, six cells or fewer, five cells or fewer, four cells or fewer, three cells or fewer, two cells or fewer, or a single target cell. This configuration may be preferred when the target cell population is circulating tumor cells (CTCs), which circulate in very few numbers and therefore tend to be collected and purified in low numbers from biological samples.

In other embodiments electrode arrays can have any suitable shape, e.g., a rectangular, circular, a circle on a rectangular line ("circle-on-line"), a square on a rectangular line or a sinusoidal line. They can also take the form of curved lines such as, but not limited to spirals or arcs.

In each configuration, the substrate of the device has a surface suitable for cancer cell attachment and spreading; where either cell attachment or spreading on the substrate can result in a detectable change in impedance between or among the electrode structures within each electrode array. Cell attachment and spreading of cell populations on the device broadly has been shown to raise impedance whereas detachment and rolling of cell populations on the device has been shown generally to lower impedance. It was found that the device not only reproducibly detected cancer cell death but was able to identify differences in cell-substrate impedance over time using different chemotoxic compounds, different effector cells and different cancer cells, including circulating tumor cells (CTCs) which confirms the device and system can also be applied to methods for identifying or validating compounds or effector cells having desirable antitumor activities against particular tumor or cancer cells, and thus permits the cell-substrate impedance monitoring device to be used in a personalized medicine approach.

Structurally, an interdigitated electrode array of two or more electrode structures is constructed to have dimensions and spacing such that they can, when connected to a signal source, operate as a unit to generate an electrical field in the region of spaces around the electrode structures. As used herein, an "electrode structure" refers to a single electrode, particularly one with a complex structure. For example, an electrode structure can have two or more electrode elements that are electrically connected together. In further embodiments the electrode array has two electrode structures, each of which has multiple electrode elements, or substructures. In preferred embodiments, the electrode structures of each interdigitated electrode array of the device has substantially the same surface area. In further preferred embodiments, each interdigitated electrode array includes two electrode structures, and each electrode structure has multiple electrode elements. Each of the two electrode structures of an electrode array is connected to a separate connection pad that is located at the edge of the substrate.

Thus, in some embodiments, for each electrode array, the first of the two electrode structures is connected to one of the two or more connection pads, and the second of the two electrode structures is connected to another of the two or more connection pads. Preferably, each array is individually addressed, meaning that the electrical traces and connection pads of the arrays are configured such that an array can be connected to an impedance analyzer in such a way that a measuring voltage can be applied across a single array at a given time by using switches (such as electronic switches).

Each interdigitated electrode array has an approximately uniform electrode resistance distribution across the entire array. By "uniform resistance distribution across the array" is meant that when a measurement voltage is applied across the electrode structures of the array, the electrode resistance at any given location of the array is approximately equal to the electrode resistance at any other location on the array. Preferably, the electrode resistance at a first location on an array of the device and the electrode resistance at a second location on the same array does not differ by more than 30%. More preferably, the electrode resistance at a first location on an array of the device and the electrode resistance at a second location on the same array does not differ by more than 15%. Even more preferably, the electrode resistance at a first location on an array of the device and a second location on the same array does not differ by more than 5%. More preferably yet, the electrode resistance at a first location on an array of the device and a second location on the same array does not differ by more than 2%.

In preferred arrangements of the interdigitated array, the electrode elements, gaps between the electrodes and electrode buses in a given electrode array are used to allow all cells, no matter where they land and attach to the electrode surfaces, to contribute similarly to the total impedance change measured for the electrode array. Thus, it is desirable to have similar electric field strengths at any two locations within any given array of the device when a measurement voltage is applied to the electrode array. At any given location of the interdigitated array, the field strength is related to the potential difference between the nearest point on a first electrode structure of the array and the nearest point on a second electrode structure of the array. It is therefore desirable to have similar electric potential drops across the electrode elements and across the electrode buses of a given interdigitated array. Based on this requirement, it is preferred to have an approximately uniform electrode resistance distribution across the whole interdigitated array where the electrode resistance at a location of interest is equal to the sum of the electrode resistance between the nearest point on a first electrode structure (that is the point on the first electrode structure nearest the location of interest) and a first connection pad connected to the first electrode structure and the electrode resistance between the nearest point on a second electrode structure (that is the point on the first electrode structure nearest the location of interest) and a second connection pad connected to the second electrode structure.

Approximately uniform distribution across the whole interdigitated array can be achieved, for example, by having electrode structures and electrode buses of particular spacing and dimensions (lengths, widths, thicknesses and geometrical shapes) such that the resistance at any single location on the interdigitated array is approximately equal to the resistance at any single other location on the interdigitated array. In most embodiments, the electrode elements (or electrode structures) of a given interdigitated array will have even spacing and be of similar thicknesses and widths, the electrode buses of a given interdigitated array will be of similar thicknesses and widths, and the electrode traces leading from a given array to a connection pad will be of closely similar thicknesses and widths. Thus, in these preferred embodiments, an interdigitated array is designed such that the lengths and geometrical shapes of electrode elements or structures, the lengths and geometrical shapes of electrode traces, and the lengths and geometrical shapes of buses allow for approximately uniform electrode resistance distribution across the array.

In some preferred embodiments of cell-substrate impedance measurement devices, electrode structures comprise multiple electrode elements, and each electrode element connects directly to an electrode bus. Electrode elements of a first electrode structure connect to a first electrode bus, and electrode elements of a second electrode structure connect to a second electrode bus. In these embodiments, each of the two electrode buses connects to a separate connection pad via an electrical trace. Although the resistances of the traces contribute to the resistance at a location on the interdigitated array, for any two locations on the array the trace connections from the first bus to a first connection pad and from the second bus to a second connection pad are identical. Thus, in these preferred embodiments trace resistances do not need to be taken into account in designing the geometry of the array to provide for uniform resistances across the array.

In some embodiments of each array configuration, the device for monitoring cell-substrate impedance has two or more electrode arrays that share a connection pad. Preferably one of the electrode structures of at least one of the electrode arrays of the device is connected to a connection pad that also connects to an electrode structure of at least one other of the electrode arrays of the device. Preferably for at least two arrays of the device, each of the two or more arrays has a first electrode structure connected to a connection pad that connects with an electrode structure of at least one other electrode array, and each of the two or more arrays has a second electrode structure that connects to a connection pad that does not connect with any other electrode structures or arrays of the device. Thus, in preferred designs of a device there are at least two electrode arrays each of which has a first electrode structure that is connected to a common connection pad and a second electrode structure that is connected to an independent connection pad.

In some preferred embodiments, each of the electrode structures of an array is connected to an electrode bus that is connected to one of the two or more connection pads of the device via an electrically conductive trace. In preferred embodiments, each of the two electrode structures is connected to a single bus, such that each array connects to two buses, one for each electrode structures. In this arrangement, each of the two buses connects to a separate connection pad of the substrate.

The electrically conductive traces that connect a bus with a connection can be fabricated of any electrically conductive material. The traces can be localized to the surface of the substrate, and can be optionally covered with an insulating layer. Alternatively the traces can be disposed in a second plane of the substrate. Description of arrangements and design of electrically conductive traces on impedance measurement devices can be found in U.S. Pat. No. 7,470,533, herein incorporated by reference for all disclosure on fabrication and design of electrically conductive trace on substrates.

Appropriate electronic means for connection, such as metal clips, engaged onto the connection pads on the substrate and connected printed-circuit-boards can be used for leading the electronic connections from the connection pads on the devices to external electronic circuitry (e.g. an impedance analyzer). Description of the design of cell-substrate impedance devices and their manufacture can be found in U.S. Pat. No. 7,470,533, herein incorporated by reference for all description and disclosure of the design, features, and manufacture of impedance device comprising electrode arrays.

Preferably the nonconducting substrate is planar, and is flat or approximately flat. Exemplary substrates can comprise many materials, including, but not limited to, silicon dioxide on silicon, silicon-on-insulator (SOI) wafer, glass (e.g., quartz glass, lead glass or borosilicate glass), sapphire, ceramics, polymer, fiber glass, plastics, e.g., polyimide (e.g. Kapton, polyimide film supplied by DuPont), polystyrene, polycarbonate, polyvinyl chloride, polyester, polypropylene and urea resin. Preferably, the substrate and the surface of the substrate are not going to interfere with molecular binding reactions that will occur at the substrate surface. For cell-substrate impedance monitoring, any surface of the nonconducting substrate that can be exposed to cancer cells during the use of a device of the present invention is preferably biocompatible. Substrate materials that are not biocompatible can be made biocompatible by coating with another material, such as polymer or biomolecular coating.

All or a portion of the surface of a substrate can be chemically treated, including but not limited to, modifying the surface such as by addition of functional groups, or addition of charged or hydrophobic groups.

Descriptions of electrode arrays used for impedance measurement that apply to the devices of the present invention are described in parent U.S. Pat. No. 7,470,533, herein incorporated by reference for all disclosure relating to electrode arrays (or structural units), electrode structures, electrode materials, electrode dimensions, and methods of manufacturing electrodes on substrates.

In some preferred devices, electrode arrays are fabricated on a substrate, in which the arrays comprises two electrode structures, each of which comprises multiple circle-on-line electrode elements, in which the electrode elements of one structure alternate with the electrode elements of the opposite electrode structure. Interdigitated electrode elements (or electrode structures) of an array of the present device of the present invention are of approximately equal widths. Preferably the electrode elements (or electrode structures) of an array of the present device of the present invention are greater than 30 microns in width, more preferably from about 50 to about 300 microns in width, and more preferably yet about 90 microns in width.

Preferably, the electrode elements (or electrode structures) of an interdigitated array are approximately evenly spaced. Preferably, the gap between electrode elements (or electrode structures) of an array of the present device of the present invention is less than 50 microns in width, more preferably from about 5 to about 30 microns in width, and more preferably yet about 20 microns in width.

The device can include one or more fluid-impermeable receptacles, preferably embodied as wells, which serve as fluid containers. Such receptacles may be reversibly or irreversibly attached to or formed within the substrate or portions thereof (such as, for example, wells formed as in a microtiter plate). In another example, the device includes microelectrode strips reversibly or irreversibly attached to plastic housings that have openings that correspond to electrode structure units located on the microelectrode strips. Suitable fluid container materials comprise plastics, glass, or plastic coated materials such as ceramics, glass, metal, etc. Descriptions and disclosure of devices that comprise fluid containers can be found in parent U.S. Pat. No. 7,470,533, herein incorporated by reference for all disclosure of fluid containers and fluid container structures that can engage a substrate comprising electrodes for impedance measurements, including their dimensions, design, composition, and methods of manufacture.

In preferred embodiments, each electrode array on the substrate of a device is associated with a fluid-impermeable container or receptacle, such as, for example, a well. Preferably, the device is assembled to a bottomless, multiwell plastic plate or strip with a fluid tight seal. The device is assembled such that a single array of the substrate is at the bottom of a receptacle or well. Preferably, each array of a device is associated with a well of a multiwell plate. In some embodiments, a multiwell device for cell-substrate impedance measurement has "non-array" wells that are attached to the substrate but not associated with arrays. Such wells can optionally be used for performing non-impedance based assays, or for viewing cells microscopically.

The design and assembly of multiwell impedance measurement devices is described in parent U.S. Pat. No. 7,470,533, and also in U.S. Pat. No. 7,192,752, both herein incorporated by reference for disclosure of multiwell impedance measurement devices, including their design, composition, and manufacture. The device preferably has between 2 and 1,536 wells, more preferably between 4 and 384 wells, and even more preferably, between 16 and 96 wells, all or less than all or which are associated with electrode arrays.

In some preferred embodiments, commercial tissue culture plates can be adapted to fit the device. Bottomless plates may also be custom-made to preferred dimensions. Preferably, well diameters are from about 1 millimeter to about 20 millimeters, more preferably from about 2 millimeters to about 8 millimeters at the bottom of the well (the end disposed on the substrate). The wells can have a uniform diameter or can taper toward the bottom so that the diameter of the container at the end in contact with the substrate is smaller than the diameter of the opposing end.

The device itself preferably forms part of a cell-substrate impedance measurement system, which includes a) at least one multiple-well cell-substrate impedance measuring device, in which at least two of the multiple wells include an electrode array at the bottom of the well; b) an impedance analyzer electronically connected to the multiple-well cell-substrate impedance measuring device; c) a device station capable of engaging the one or more multiple-well devices and having electronic circuitry capable of selecting and connecting electrode arrays within any of the multiple wells to the impedance analyzer; and d) a software program connected to the device station and impedance analyzer to control the device station and perform data acquisition and data analysis from the impedance analyzer.

In the cell-substrate impedance measurement systems, the impedance analyzer engages connection pads of one or more multi-well devices to measure impedance. In one embodiment of the above system, the impedance analyzer is capable of measuring impedance between 0.1 ohm and $10^5$ ohm in frequency range of 1 Hz to 1 MHz. The impedance analyzer is preferably capable of measuring both resistance and reactance (capacitive reactance and inductive reactance) components of the impedance. In a preferred embodiment of the above system, the impedance analyzer is capable of measuring impedance between 0.1 ohm and $10^3$ ohm in frequency range of 100 Hz to 100 kHz.

A cell-substrate measurement system can be used to efficiently and simultaneously perform multiple assays by using circuitry of the device station to digitally switch from recording from measuring impedance over an array in one well to measuring impedance over an array in another well. In one embodiment of the above system, the system under software control is capable of completing an impedance measurement for an individual well at a single frequency within less than ten seconds. In another embodiment, the averaged time used by the system to complete an impedance measurement for an individual well at a single frequency is less than one second.

The device when connected to an impedance analyzer, can measure differences in impedance values that relate to cell behavior. For example, the cell-substrate impedance measuring device can be used to measure differences in impedance values when cells are attached to the electrode array and when cells are not attached to the electrode array, or can detect differences in impedance values when the number, type, activity, adhesiveness, or morphology of cells attached to the electrode-comprising surface of the apparatus changes.

The cell-substrate impedance monitoring devices are preferably held by a device station having one or more platforms or one or more slots for positioning one or more multiwell devices. The one or more platforms or one or more slots can comprise sockets, pins or other devices for electrically connecting the device to the device station. The device station preferably can be positioned in a tissue culture incubator during cell impedance measurement assays. It can be electrically connected to an impedance analyzer and computer that are preferably located outside the tissue culture incubator.

The device station has electronic circuitry that can connect to an impedance monitoring device and an impedance analyzer and electronic switches that can switch on and off connections to each of the two or more electrode arrays of the multiwell devices used in the system. The switches of the device station are controlled by a software program. The software program directs the device station to connect arrays of the device to an impedance analyzer and monitor impedance from one or more of the electrode arrays. During impedance monitoring, the impedance analyzer can monitor impedance at one frequency or at more than one frequency. Preferably, impedance monitoring is performed at more than one time point for a given assay, and preferably, impedance is monitored at at least three time points, including before and after adding effector cells. The device station can connect individual arrays of a device to an impedance analyzer to monitor one, some, or all of the arrays of a device for a measurement time point. The switches of the device station allow the selected individual arrays to be monitored in rapid succession for each desired monitoring time point. Each monitoring time point is in fact a narrow time frame (for example from less than one second to minutes) of measurement in the assay during which impedance monitoring is performed. In some preferred embodiments of the present invention, the device station software is programmable to direct impedance monitoring of any of the wells of the device that comprise arrays at chosen time intervals.

The software of the impedance monitoring system can also store and display data. Data can be displayed on a screen, as printed data, or both. Preferably the software can allow entry and display of experimental parameters, such as descriptive information including cells types, compound concentrations, time intervals monitored, etc.

Preferably, the software can also analyze impedance data. In preferred embodiments, the software can calculate a cell index (CI) for one or more time points for one or more wells of the multiwell device. In some preferred embodiments, the software can calculate a cell change index (CCI) from impedance measurements of one or more wells of the multiwell device. The software can preferably generate plots of impedance data and impedance values, such as but not limited to CI or CCI, with respect to time. The software may perform other analysis as well, such as calculate cell number from CI, generate dose-response curves based on impedance data, calculate IC values based on impedance values, and calculate kinetic parameters of cell growth or behavior based on impedance values and impedance value curves. The software of the impedance monitoring system can also store and display analyses of the data, such as calculated impedance values and kinetic parameters derived therefrom, Data can be displayed on a screen, as printed data, or both.

C. Cell Index and Cell Change Index as a Parameter for Comparison

In some embodiments, cell-substrate impedance values can be plotted and compared to one another to identify change in the target cell population. However, based on the dependent relationship between the measured impedance, cell number (more accurately, the viable cell number, or attached cell number) and cell attachment status, it is possible to derive a so-called "cell number index" or "cell index" from the measured impedance frequency spectra that provides a useful index for quantitating and comparing target cell behavior in the impedance-based assays of the present invention. In preferred embodiments, the impedance based parameter derived from impedance is used for comparison to determine effectiveness of modulating the target cell population.

Cell index has been discussed previously. The term "cell index" in the present application is also meant to include "cell number index" as in U.S. Pat. Nos. 7,470,583, 7,192,752, and 7,470,533, which are each herein incorporated by reference for the discussions and disclosures of cell index and cell number index they contain.

The invention includes several methods of calculating cell index for cells attached to two or more essentially identical arrays of a cell-substrate impedance device, where the cells are monitored for impedance changes. By "essentially identical electrode arrays" or "essentially identical arrays" is meant that the dimensions and arrangement of electrodes, electrode structures, and electrode elements is the same for the referenced arrays. Thus, two essentially identical electrode arrays will have electrode structures of the same dimensions (length, width, thickness), where the electrode structures have the same number of electrode elements, and the arrangement of electrode structures and electrode elements in each array are the same. By arrangement is meant the distance between structures or elements (gap width), their physical position with respect to one another, and their geometry (angles, degree of curvature, circle-on-line or castellated geometries, etc.), including the same features of any electrode buses that may be connected to electrode structures or electrode elements. Electrodes of essentially identical arrays also comprise the same materials. For the purposes of calculating trace resistances and cell index number, a substrate can have any number of essentially identical arrays.

Impedance (Z) has two components, namely the resistance Rs and reactance Xs. Mathematically, the impedance Z is expressed as follows, $$Z = Rs + jXs, \quad (1)$$

where $j = \sqrt{-1}$, depicting that for the (serial) reactance component Xs, the voltage applied over it is 90 degree phased-out from the current going through it. For the (serial) resistance, the voltage applied over it is in phase with the current going through it. As it is well-known in electronic and electrical engineering, the impedance can also be expressed in terms of parallel resistance Rp and parallel reactance Xp, as follows, $$Z = Rp*(jXp)/(Rp+jXp), \quad (2)$$

where $j = \sqrt{-1}$. Nevertheless, these expressions (serial resistance and serial reactance, or parallel resistance and parallel reactance) are equivalent. Those who are skilled in electrical and electronic engineering can readily derive one form of expression from the parameter values in the other expression. For the sake of clarity and consistency, the description and discussion in the present invention utilizes the expression of serial resistance and serial reactance. For simplicity, serial resistance and serial reactance are simply called resistance and reactance.

As described in U.S. Pat. No. 7,470,533, which is herein incorporated by reference for disclosures relating to cell-substrate impedance monitoring, monitoring cell-substrate impedance for detection or measurement of change in impedance can be done by measuring impedance in any suitable range of frequencies. For example, the impedance can be measured in a frequency range from about 1 Hz to about 100 MHz. In another example, the impedance can be measured in a frequency range from about 100 Hz to about 2 MHz. The impedance is typically a function of the frequency, i.e., the impedance values change as frequency changes. Monitoring cell-substrate impedance can be done either in a single frequency or multiple frequencies. If the impedance measurement is performed at multiple frequencies, then a frequency-dependent impedance spectrum is obtained—i.e., there is an impedance value at each measured frequency. As mentioned above, the impedance has two components—a resistance component and a reactance component. A change in either resistance component or reactance component or both components can constitute a change in impedance.

As described in the U.S. Pat. No. 7,470,533, herein incorporated by reference for disclosure of methods of measuring electrical impedance, the method for the measurement of electrical (or electronic) impedance is achieved by, (1) applying a voltage between or among said electrodes at a given frequency (or multiple frequencies, or having specific voltage waveform) and monitoring the electrical current through said electrodes at the frequency (or multiple frequencies, or having specific waveform), dividing the voltage amplitude value by the current amplitude value to derive the impedance value; (2) applying an electric current of a single frequency component (or multiple frequencies or having specific current wave form) through said electrodes and monitoring the voltage resulted between or among said electrodes at the frequency (or multiple frequencies, or having specific waveform), dividing the voltage amplitude value by the current amplitude value to derive the impedance value; (3) other methods that can measure or determine electric impedance. Note that in the description above of "dividing the voltage amplitude value by the current amplitude value to derive the impedance value", the "division" is done for the values of current amplitude and voltage amplitude at same frequencies. As it is well-known in electrical and electronic engineering, in such calculations (e.g. divisions mentioned above), the current amplitude and voltage amplitude are expressed in the form of complex numbers, which take into account of how big the current and the voltage are and what the phase difference between the sinusoidal waves of the current and the voltage is. Similarly, the impedance value is also expressed in a complex form, having both resistance and reactance component, as shown in equations above.

As described in the U.S. Pat. No. 7,470,533, incorporated herein by reference for disclosure relating to Cell Index or Cell Number Index, the measured cell-substrate impedance can be used to calculate a parameter termed Cell Index or Cell Number Index. Various methods for calculating such a cell number index can be used based on the changes in resistance or reactance when cells are attached to the electrode structures with respect to the cases no cells are attached to the electrode structures. The impedance (resistance and reactance) of the electrode structures with no cell attached but with same cell culture medium over the electrode structures is sometimes referred as baseline impedance. The baseline impedance may be obtained by one or more of the following ways: (1) the impedance measured for the electrode structures with a cell-free culture medium introduced into the well containing the electrode structures, wherein the culture medium is the same as that used for the impedance measurements for the condition where the cell attachment is monitored; (2) the impedance measured shortly (e.g. 10 minutes) after the cell-containing medium was applied to the wells comprising the electrode structures on the well bottom (during the short period after cell-containing medium addition, cells do not have enough time to attach to the electrode surfaces. The length of this short-period may depend on cell type and/or surface treatment or modification on the electrode surfaces); (3) the impedance measured for the electrode structures when all the cells in the well were killed by certain treatment (e.g. high-temperature treatment) and/or reagents (e.g. detergent) (for this method to be used, the treatment and/or reagents should not affect the dielectric property of the medium which is over the electrodes).

In one example, the cell index or cell number index can be calculated by: at each measured frequency, calculating the resistance ratio by dividing the resistance of the electrode arrays when cells are present and/or attached to the electrodes by the baseline resistance, finding or determining the maximum value in the resistance ratio over the frequency spectrum, and subtracting one from the maximum value in the resistance ratio.

Using a mathematically formula, Cell Index is derived as, $$\text{Cell Index} = \max_{i=1,2,\ldots N}\left(\frac{R_{cell}(f_i)}{R_b(f_i)} - 1\right) \quad (3)$$

Where N is the number of the frequency points at which the impedance is measured. For example, if the frequencies used for the measurements are at 10 kHz, 25 kHz and 50 kHz, then N=3, $f_1$=10 kHz, $f_2$=25 kHz, $f_3$=50 kHz. $R_{cell}(f_i)$ is the resistance (cell-substrate resistance) of the electrode arrays or electrode structures when the cells are present on the electrodes at the frequency $f_i$ and $R_b(f_i)$ is the baseline resistance of the electrode array or structures at the frequency $f_i$.

The cell index obtained for a given well reflects: 1) how many cells are attached to the electrode surfaces in this well, 2) how well cells are attached to the electrode surfaces in the well. In this case, a zero or near-zero "cell index or cell number index" indicates that no cells or very small number of cells are present on or attached to the electrode surfaces. In other words, if no cells are present on the electrodes, or if the cells are not well-attached onto the electrodes, $R_{cell}(f_i)$ is about the same as $R_b(f_i)$, leading to Cell Index=0. A higher value of "cell number index" indicates that, for same type of the cells and cells under similar physiological conditions, more cells are attached to the electrode surfaces. In other words, under same physiological conditions, more cells attached on the electrodes, the larger the values $R_{cell}(f_i)$ is, leading to a large value for Cell Index. Thus Cell Index is a quantitative measure of cell number present in a well. A higher value of "cell index" may also indicate that, for same type of the cells and same number of the cells, cells are attached better (for example, cells spread out more, or cell adhesion to the electrode surfaces is stronger) on the electrode surfaces.

Thus, for same number of the cells present in the well, change in a cell status will lead to a change in cell index. For example, an increase in cell adhesion or a cell spread leading to large cell/electrode contact area will result in an increase in $R_{cell}(f)$ and a larger Cell Index. On the other hand, a cell death or toxicity induced cell detachment, cell rounding up, will lead to smaller $R_{cell}(f)$ and thus smaller Cell Index.

In another example, the cell number index can be calculated by: at each measured frequency, calculating the reactance ratio by dividing the reactance of the electrode arrays when cells are present on and/or attached to the electrodes by the baseline reactance, finding or determining the maximum value in the reactance ratio over the frequency spectrum, and subtracting one from the maximum value in the resistance ratio.

In this case, a zero or near-zero "cell number index" indicates that no cells or very small number of cells are present on or attached to the electrode surfaces. A higher value of "cell number index" indicates that, for same type of the cells and cells under similar physiological conditions, more cells are attached to the electrode surfaces.

In yet another example, the cell index can be calculated by: at each measured frequency, subtracting the baseline resistance from the resistance of the electrode arrays when cells are present or attached to the electrodes to determine the change in the resistance with the cells present relative to the baseline resistance; then finding or determining the maximum value in the change of the resistance.

In this case, "cell-number index" is derived based on the maximum change in the resistance across the measured frequency range with the cells present relative to the baseline resistance. This cell index would have a dimension of ohm.

In yet another example, the cell index can be calculated by: at each measured frequency, calculating the magnitude of the impedance (equaling to $\sqrt{R_s^2 + X_s^2}$, where $R_s$ and $X_s$ are the serial resistance and reactance, respectively); subtracting the magnitude of the baseline impedance from the magnitude of the impedance of the electrode arrays when cells are present or attached to the electrodes to determine the change in the magnitude of the impedance with the cells present relative to the baseline impedance; then finding or determining the maximum value in the change of the magnitude of the impedance.

In this case, "cell-number index" is derived based on the maximum change in the magnitude of the impedance across the measured frequency range with the cells present relative to the baseline impedance. This cell index would have a dimension of ohm.

In yet another example, the index can be calculated by: at each measured frequency, calculating the resistance ratio by dividing the resistance of electrode arrays when cells are present or attached to the electrodes by the baseline resistance; then calculating the relative change in resistance in each measured frequency by subtracting one from the resistance ratio; then integrating all the relative-change value (i.e., summing together all the relative-change values at different frequencies).

In this case, "cell-number index" is derived based on multiple-frequency points, instead of single peak-frequency like above examples. Again, a zero or near-zero "cell number index" indicates that on cells are present on the electrodes. A higher value of "cell number index" indicates that, for same type of the cells and cells under similar physiological conditions, more cells are attached to the electrodes.

In yet another example, the cell index can be calculated by: at each measured frequency, subtracting the baseline resistance from the resistance of the electrode arrays when cells are attached to the electrodes to determine the change in the resistance with the cells present relative to the baseline impedance; (here the change in the resistance is given by $\Delta R(f_i) = R_{s\text{-}cell}(f_i) - R_{s\text{-}baseline}(f_i)$ for the frequency $f_i$, $R_{s\text{-}cell}$ and $R_{s\text{-}baseline}$ are the serial resistances with the cells present on the electrode array and the baseline serial resistances, respectively); analyzing the frequency dependency of the change of the resistance to derive certain parameters that can quantify such dependency. In one example, such parameters can be calculated as $$\sqrt{\sum_i [\Delta R(f_i)]^2}.$$

In another example, such parameter can be calculated as $$\sum_i |\Delta R(f_i)|.$$

The parameter(s) are used as cell index or cell number index.

In this case, "cell-number index" is derived based on the analysis of the frequency spectrum of the change in the resistance. Depending how the parameters are calculated, the cell index may have a dimension of ohm.

In yet another example, the cell index can be calculated by: at each measured frequency, calculating the magnitude of the impedance (equaling to $\sqrt{R_s^2+X_s^2}$, where $R_s$ and $X_s$ are the serial resistance and reactance, respectively); subtracting the magnitude of the baseline impedance from the magnitude of the impedance of the electrode arrays when cells are attached to the electrodes to determine the change in the magnitude of the impedance with the cells present relative to the baseline impedance; (here, the change in the magnitude of the impedance is given by $\Delta Z(f_i)=|Z_{cell}(f_i)|-|Z_{baseline}(f_i)|$ for the frequency $f_i$, $|Z_{cell}(f_i)|=\sqrt{R_{s-cell}(f_i)^2+X_{s-cell}(f_i)^2}$, $R_{s-cell}$ and $X_{s-cell}$ being the serial resistance and reactance with the cells present on the electrode arrays, respectively, $|Z_{cell}(f_i)|$ is the magnitude of the impedance of the electrode array with cells present on the electrode arrays, $|Z_{baseline}(f_i)|$ is the magnitude of the baseline impedance of the electrode array); and analyzing the frequency dependency of the change of the magnitude of the impedance to derive certain parameters that can quantify such dependency. In one example, such parameters can be calculated as $$\sqrt{\sum_i [\Delta Z(f_i)]^2}.$$

In another example, such parameter can be calculated as $$\sum_i |\Delta Z(f_i)|.$$

The parameter(s) are used as cell index or cell number index.

In this case, "cell-number index" is derived based on the analysis of the frequency spectrum of the change in the magnitude of the impedance. Depending how the parameters are calculated, the cell index may have a dimension of ohm.

As described in the U.S. Pat. No. 7,470,533, and PCT application number PCT/US03/22557, and U.S. Pat. No. 7,192,752, all herein incorporated by reference for disclosure of Cell Index or Cell Number Index and its calculation, there are different methods for calculating the parameter termed Cell Index or Cell Number Index from the measured cell-substrate impedance (resistance or reactance). Cell Index or Cell Number Index is a quantitative measure of cells in the wells under cell-substrate impedance measurement.

It is worthwhile to point out that it is not necessary to derive such a "cell number index" for utilizing the impedance information for monitoring cell conditions over the electrodes. Actually, one may choose to directly use measured impedance (e.g., at a single fixed frequency; or at a maximum relative-change frequency, or at multiple frequencies) as an indicator of cell conditions. If measured impedance values are directly used for monitoring cell conditions, then resistance, or reactance or both resistance and reactance can be used.

Still, deriving "cell index" or "cell number index" and using such index to monitor cell conditions may have advantages. There are several advantages of using "cell number index" to monitor cell growth and/or attachment and/or viability conditions.

First, one can compare the performance of different electrode geometries by utilizing such cell number index.

Secondly, for a given electrode geometry, it is possible to construct "calibration curve" for depicting the relationship between the cell number and the cell number index by performing impedance measurements for different number of cells added to the electrodes (in such an experiment, it is important to make sure that the seeded cells have well-attached to the electrode surfaces). With such a calibration curve, when a new impedance measurement is performed, it is then possible to estimate cell number from the newly-measured cell number index.

Thirdly, cell number index can also be used to compare different surface conditions. For the same electrode geometry and same number of cells, a surface treatment given a larger cell number index indicates a better attachment for the cells to the electrode surface and/or better surface for cell attachment.

As shown above, for some methods of calculating cell index or cell number index, it is important to know the impedance (resistance and/or reactance) of the electrode structures with and without cells present on them. Based on the equation (1), the impedance of the electrode array (with or without cells present on the electrodes) is given by $$Z_{electrode-array}=Z_{total}-Z_{trace}-Z_{switch} \qquad (4)$$

Where $Z_{switch}$ is the impedance of electronic switch at its on stage, $Z_{trace}$ is the impedance of the electrical connection traces (or electrical conductive traces) on the substrate between the connection pads and the electrode buses, $Z_{total}$ is the total impedance measured at the impedance analyzer. By choosing electronic switches with good quality, it is possible to have all the electronic switches have a consistent on-impedance (mainly resistance). For example, the on-resistance of electronic switches can be about 3 ohm (+/− 10%) with the on reactance being negligible (for example, less than 0.2 ohm in the frequency range of interest). Thus, if the trace impedance is determined or calculated, then formula (4) can be used to calculate the impedance of the electrode arrays with or without cells present.

In some embodiments, the parameter for comparison is a Normalized Cell Index. A "Normalized Cell Index" at a given time point is calculated by dividing the Cell Index at the time point by the Cell Index at a reference time point. Thus, the Normalized Cell Index is 1 at the reference time point. Normalized cell index is cell index normalized against cell index at a particular time point. In most cases in the present applications, normalized cell index is derived as normalized relative to the time point immediately before a compound addition or treatment. Thus, normalized cell index at such time point (immediately before compound addition) is always unit one for all wells. One possible benefit for using such normalized cell index is to remove the effect from difference in cell number in different wells. A well having more cells may produce a larger impedance response following compound treatment. Using normalized cell index, it helps to remove such variations caused by different cell numbers.

A "delta cell index" at a given time point is calculated by subtracting the cell index at a standard time point from the cell index at the given time point. Thus, the delta cell index is the absolute change in the cell index from an initial time (the standard time point) to the measurement time.

In some embodiments a "cell change index" is used as the parameter for comparison. The time-dependent cellular response (including cytolytic response) may be analyzed by deriving parameters that directly reflect the changes in cell status. For example, time dependent cellular response may be analyzed by calculating the slope of change in the measured impedance responses (that is equivalent to the first order derivative of the impedance response with respect to time, impedance response here can be measured impedance data or derived values such as cell index, normalized cell index or delta cell index). In another example, the time-dependent cellular responses (including cytolytic responses) may be analyzed for their higher order derivatives with respect to time. Such high order derivatives may provide additional information as for how cells responding to different compounds and as for the mechanisms of compound action.

As an example, we describe how one can to derive a parameter, called Cell Change Index, based on the real time, quantitative information (i.e., cell index, CI) about biological status of cells in the wells provided from RT-CES system. This new parameter, Cell Change Index (CCI), can effectively link time dependent cell index I with cell status, is calculated as, $$CCI(t) = \frac{dCI(t)}{CI(t) \cdot dt}. \quad (5)$$

Thus CCI is the normalized rate of change in cell index. CCI values can be used to quantify the cell status change. For cells in an exponential growth under regular cell culture condition, the cell index determined by a cell-substrate impedance monitoring system described herein is expected to be a proportionate measure of the cell number in the well since the cell morphology and average extent of cell adhesion to the electrode surfaces among the whole cell population do not exhibit significant changes over time. Thus, the cell index (CI) increase with time following an exponential function, such that $$CI(t) = CI(0) * 2^{\frac{t}{DT}} \quad (6)$$

where DT is the cell doubling time. For such exponential growth culture, CCI(t) is a constant, giving $$CCI(t) = \frac{0.693}{DT} \approx \frac{0.7}{DT}. \quad (7)$$

Thus, several types of CCI(t) can be classified as:

If CCI is about 0.7/DT, cell index increases in the same rate as that expected for an exponential growth of the cells.

If CCI>>0.7/DT, cell index increases faster than that expected for an exponential growth (or log growth) of the cells. This indicates that cells may grow faster than regular exponential growth, or cells may exhibit some morphology change (e.g. cell spreading out or adhering better to the electrode surfaces), leading to large impedance signal, or both of above effects, or there may be other cell behaviors occurring particular to the assay or culture conditions.

If CCI is more than zero but somewhat smaller than 0.7/DT, then cell index increases in the rate slowed than that expected for an exponential growth. This indicates that cell growth rate may be slowed down relative to exponential growth, or cell growth may be somewhat inhibited by chemical compounds added to the culture media or by other cell culture parameters, or that certain populations of cells are dying off and detaching from the electrode surfaces, or there may be other cell behaviors occurring particular to the assay or culture conditions.

If CCI is about zero, then cell index shows a near constant value. This may indicate that the cell growth is nearly-completely inhibited. For example, all the cells are arrested at certain points of cell cycle and are not progressing further. Or, this may indicate that the number of cells dying off in the culture is nearly as the number of newly-divided cells. Alternatively this may indicate that cells reach stationary phase of cell culture. Alternatively this may indicate that number of cells are above the detection upper limit of the cell-substrate impedance monitoring system. There is also the possibility of other cell behaviors occurring particular to the assay or culture conditions.

If CCI is negative, then the cell index is decreasing with time, showing the cells losing attachment to the electrode surface or changing their morphology.

If CCI is very negative, then the cell index decreases rapidly with time, showing that either cells lose attachment to the electrode surfaces quickly or cells change their morphology very quickly.

D. Cell-Substrate Impedance Monitoring of Cancer Cells

The cell-substrate impedance monitoring devices and systems are applied to methods for assessing the effect of proposed anticancer therapeutics on cancer cells. In preferred embodiments a subject in need of cancer treatment donates cancer cells for use as target cells in the assay. One or more proposed therapeutics are added to the target cells, and cell-substrate impedance of the target cell population is monitored over time. In embodiments where the proposed therapeutics require effector cells, preferably the effector cells are also donated from the same subject. Proposed therapeutics that are more effective at killing cancer cells are considered more likely to be an effective cancer treatment for the subject or a subject suspected of suffering from a same cancer. Variations of the technical approach are introduced below.

In one exemplary approach a method of assessing cytolysis of cancer cells is provided, which includes providing a cell-substrate impedance monitoring device operably connected to an impedance analyzer, wherein the device has a well for receiving cells and an electrode array at a base of the well; adding target cells characterized as cancer cells to the well; adding effector cells to the well to form a test well, wherein the effector cells are immune cells derived from a same patient as the target cells; monitoring cell-substrate impedance of the test well before and after adding the effector cells and optionally deriving impedance-based parameters from the impedances; and determining effectiveness of effector cell killing of the target cells by comparing the impedance or impedance based parameter over time.

In another exemplary approach, the invention also provides method of assessing cytolysis of cancer cells, which includes providing a cell-substrate impedance monitoring device operably connected to an impedance analyzer, where the device has a well for receiving cells and an electrode array at a base of the well; adding one or more target cells characterized as cancer cells to the well; adding effector cells to the well to form a test well, wherein the effector cells are immune cells, further wherein the effector cells are engineered to display a binding moiety suspected of binding the target cells; monitoring cell-substrate impedance of the test well before and after adding the effector cells and optionally deriving impedance-based parameters from the impedances; and determining effectiveness of effector cell killing of target cells by comparing the impedance or impedance based parameter over time.

In another exemplary approach, the invention also provides a method of assessing cytolysis of cancer cells, which includes providing a cell-substrate impedance monitoring device operably connected to an impedance analyzer, wherein the device comprises a well for receiving cells and an electrode array at a base of the well; adding target cells characterized as cancer cells to the well; adding effector cells to the well, wherein the effector cells are immune cells, preferably from a same patient as the target cells; adding a bispecific engager to the well to form a test well, wherein the bispecific engager is a molecule configured to bridge the effector cells to the target cells; monitoring cell substrate impedance of the test well over time, including before and after the step of adding the bispecific engager, and optionally deriving impedance-based parameters from the impendences; and determining the effectiveness of effector cell killing in response to the bispecific engager by comparing the impedance or impedance based parameter over time.

In another exemplary approach, a method of assessing cytolysis of cancer cells is provided, which includes providing a cell-substrate impedance monitoring device operably connected to an impedance analyzer, wherein the device comprises a well for receiving cells and an electrode array at a base of the well; adding one or more target cells characterized as cancer cells to the well; adding an oncolytic virus to the well to form a test well, wherein the virus is suspected of recognizing and lysing cancer cells; monitoring cell-substrate impedance of the test well before and after adding the oncolytic virus and optionally deriving impedance-based parameters from the impedances; and determining effectiveness of target cell lysis by comparing the impedance or impedance based parameter over time.

The methods of the invention share an approach of using cell-substrate impedance monitoring to assess the attachment, proliferation, and change in morphology of target cells embodied as cancer cells in response to the addition of one or more proposed therapeutics, whether in compound (e.g. bispecific engager (BiTe)), cell (e.g. engineered CAR-T), or viral (oncolytic virus) form. The cancer cells can be cancer cell lines but are preferably cancer cells collected from subjects in need of or undergoing a cancer treatment so that the treatment can be individually tailored to the subject or the stage or type of cancer. Alternatively, the cancer cells can be donated from third party subjects suffering from a same cancer as the subject in need of or undergoing a cancer treatment.

Most preferably, the cancer cells added to the device as target cells are collected from a patient diagnosed with one or more forms or stages of cancer. Depending on type of cancer or tumor present, cancer cells may be collected from a variety of different biological samples. Non limiting examples include a solid tumor, a hematopoietic tumor, blood, and pleural effusion. The artisan will appreciate that cancer cell collection can be performed consistent with the characteristics of the cell or tumor. For instance, cancer cells can be collected from solid tumors or masses by tissue biopsy. Cancer cells in circulation can be collected by blood draw, followed by red blood cell lysis and optionally further separation techniques such as affinity chromotography, density centrifugation, flow cytometric sorting and others known in the art to which the invention belongs. Cancer cells collected from bodily fluids, such as pleural effusion, can be collected by needle aspiration and other approaches known in the art consistent with the particular form of cancer or tumor.

In some embodiments, cancer cells are cultured before adding to one or more wells of the cell-substrate impedance monitoring device; and in other embodiments, cancer cells are cultured in the wells of the impedance monitoring device. In still further embodiments, cancer cells are added to the device then assayed without substantial culturing.

Hemotopoietic malignancies, often referred to as blood cancers, are tumors that effect the blood, bone marrow, lymph, and lymphatic system. Among these include lymphomas, leukemias, myeloproliferative neoplasms, plasma cell dyscrasias, and histiocytic tumors. Each is applicable with the methods of the invention. Thus, the invention provides an improved method of screening for potential therapeutics to determine an effective treatment against hematopoietic malignancies by collecting cancer cells from a hematopoietic tumor from a subject in need of treatment, and monitoring cell-substrate impedance of the cancer cells before and after the addition of proposed anticancer therapeutics to determine the effectiveness of the proposed treatment.

Among the benefits of the invention is the high-resolution cell-substrate impedance monitoring of circulating tumor cells (CTCs). Circulating tumor cells (CTCs) can be found in the blood of patients suffering from various cancers. In fact, the detection of CTCs in early and/or metastatic disease has been shown to correlate with unfavorable clinical outcome. However, CTCs possess antigenic and/or genetic characteristics of specific tumor types and therefore provide a basis for which promising therapeutics may be tested. Among these include anticancer compounds (e.g. trastuzumab), cellular therapies (e.g. CAR-T), and use of a bispecific engager (e.g. BiTe) technologies.

Different approaches are available to collect CTCs from blood, which include microfluidic chips, immunomagnetic separation, filtration, density gradient separation, and flow cytometric sorting. However, a significant challenge of working with CTCs is that they are usually found at very low frequencies among normal peripheral mononuclear cells (PBMCs) and thus can be difficult to collect in sufficient numbers to assay. The methods herein are able to resolve changes to CTC populations collected from a single subject using high resolution impedance monitoring. The interdigitated impedance-based device substantially as shown in FIGS. 1A-C is able resolve and monitor morphological changes of CTCs, CTC proliferation and lysis of CTCs when fewer than 100 CTCs are added to wells of the device. Although the interdigitated electrode array can detect changes in the cancer cell population having as few as one cancer cells, still higher resolution of morphological changes of CTCs, CTC proliferation and CTC lysis can be achieved, such as when adding from 1-10 CTCs using the electrode configuration having a single measuring electrode 107 substantially as shown in FIG. 2.

Pleural effusion is a buildup of extra fluid in the space between the lungs and the chest wall. This area is called the pleural space. About half of people with cancer develop a pleural effusion. When cancer grows in the pleural space, it causes a malignant pleural effusion. This condition is a sign that the cancer has spread, or metastasized, to other areas of the body. Common causes of malignant pleural effusion are lymphoma and cancers of the breast, ovary, but most often the lung. Since pleural effusion can be caused by different types of underlying cancer, the effectiveness of treatments across different subjects can vary. Accordingly, by collecting cancer cells from the pleural effusion or pleura, the invention permits testing of different potential therapeutics against the cancer cells specific to the patient from which the cancer cells are collected. Accordingly, the testing can not only be used to treat the pleural effusion but also to treat the underlying cancer type causing the pleural effusion.

After target cells are added to the wells, they are permitted to settle on the electrode surface. Cell-substrate impedance monitoring of the population may begin upon contact with the electrode surface. Impedance is monitored over at least two time points but is frequently monitored over many time points to establish a baseline impedance, an impedance curve, and/or an impedance based curve. In some embodiments the baseline impedance corresponds to the proliferation of the cancer cells and therefore generally increases over time. In such embodiments, a proposed therapeutic may be added to a growing or exponentially growing cancer cell population and the cell-substrate impedance monitored over time to assess the effect on cancer cell proliferation.

In some embodiments, the impedance over time is directly compared to assess changes in the target cell population. In other embodiments an impedance based parameter, such as cell index, cell change index, normalized cell index or cell number is calculated from the impedance and compared over time. Methods of determining impedance based parameters are described in detail above. Furthermore, impedance or impedance based parameter can be compared over varying therapeutic doses to determine IC50 for comparison between therapeutics.

In some embodiments the impedance based parameter is a cell number (number of viable cells), which can be derived from cell index. Determining the number of viable cells can be useful when determining the effectiveness of a proposed anticancer treatment against the cancer cells. When assaying for cancer cell killing, one is often interested in how many target cells or what percentage of target cells have been killed in response to a therapeutic to gauge its effectiveness. Thus, the quantity or viability of target cells may be determined at any point during an assay using the cell-substrate impedance monitoring system. Accordingly, in some embodiments the methods include maintaining a count of target cells using cell-substrate impedance monitoring prior to adding a proposed therapeutic and after adding the proposed therapeutic to determine a percent viability or percent target cell killing. Methods for calculating cell number from cell index are provided in this document.

Figure 4:
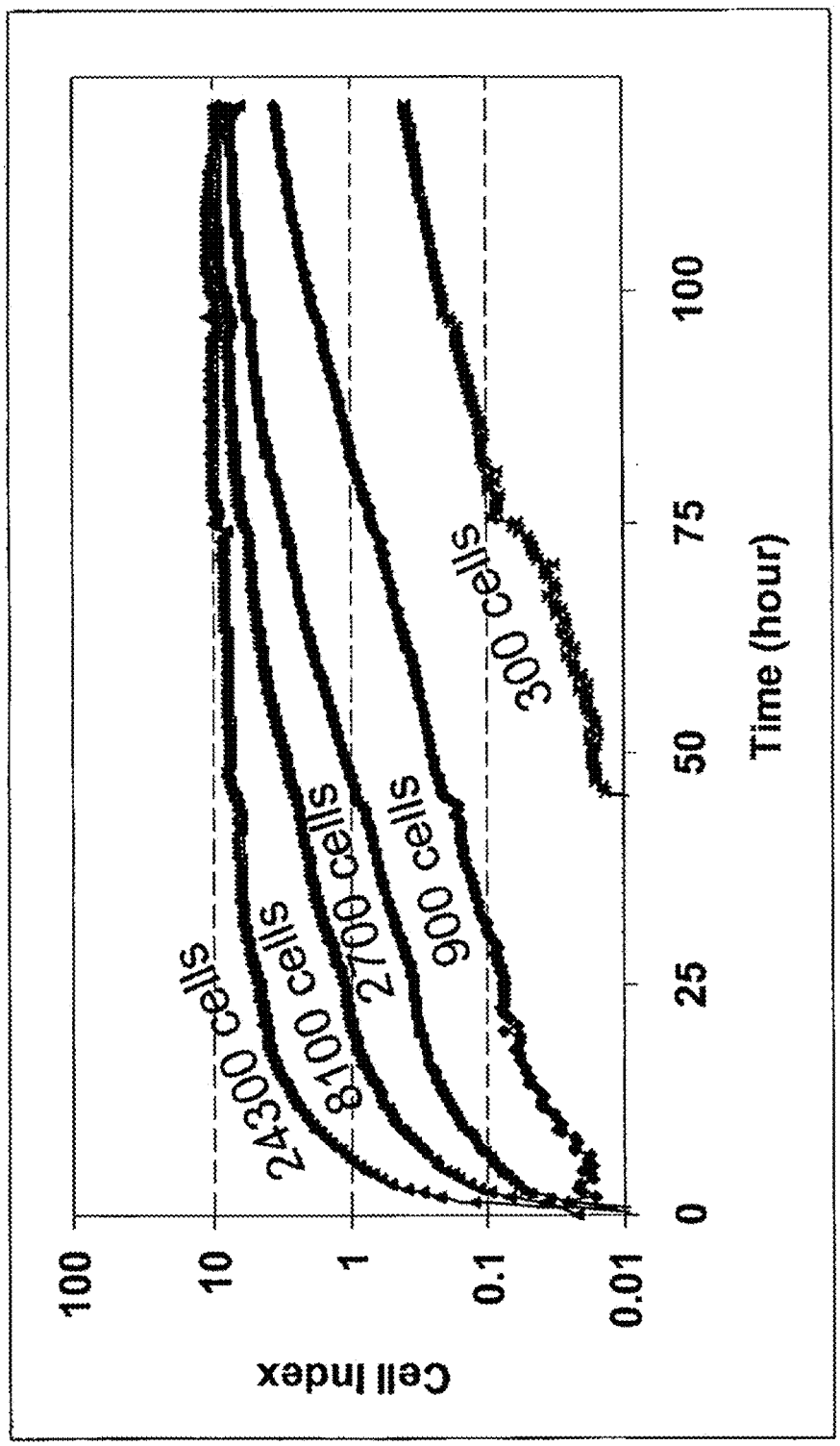
FIG. 4 shows real-time monitoring of proliferation of human non-small cell lung cancer cells (H460 cells) seeded at different initial cell seeding numbers on a cell substrate impedance monitoring system. The cell proliferation was continuously recorded every 15 minutes for over 125 hours. The cell growth curves in the log scale show exponential cell growth or cells in the stationary phase.

To demonstrate the applicability of the system for use with target cells embodied as cancer cells, FIG. 4 demonstrates the ability of the cell-substrate impedance system to monitor cancer cell proliferation. In this experiment, H460 cells were introduced into wells of a 16 well device (16× E-Plate) of a cell-substrate impedance monitoring system, with different wells receiving different initial cell seeding numbers. The device was engaged with a device station of the system that was in a tissue culture incubator that kept a temperature of 37° C. and an atmosphere of 5% $CO_2$. Cell-substrate impedance was monitored at 15 minute intervals for 125 hours. The cell index was calculated by the system for each time point and displayed as a function of time to give cell growth (proliferation) curves for each cell seeding number. The cell growth curves were plotted on a log scale showing exponential growth phases and stationary phases.

Figure 5:
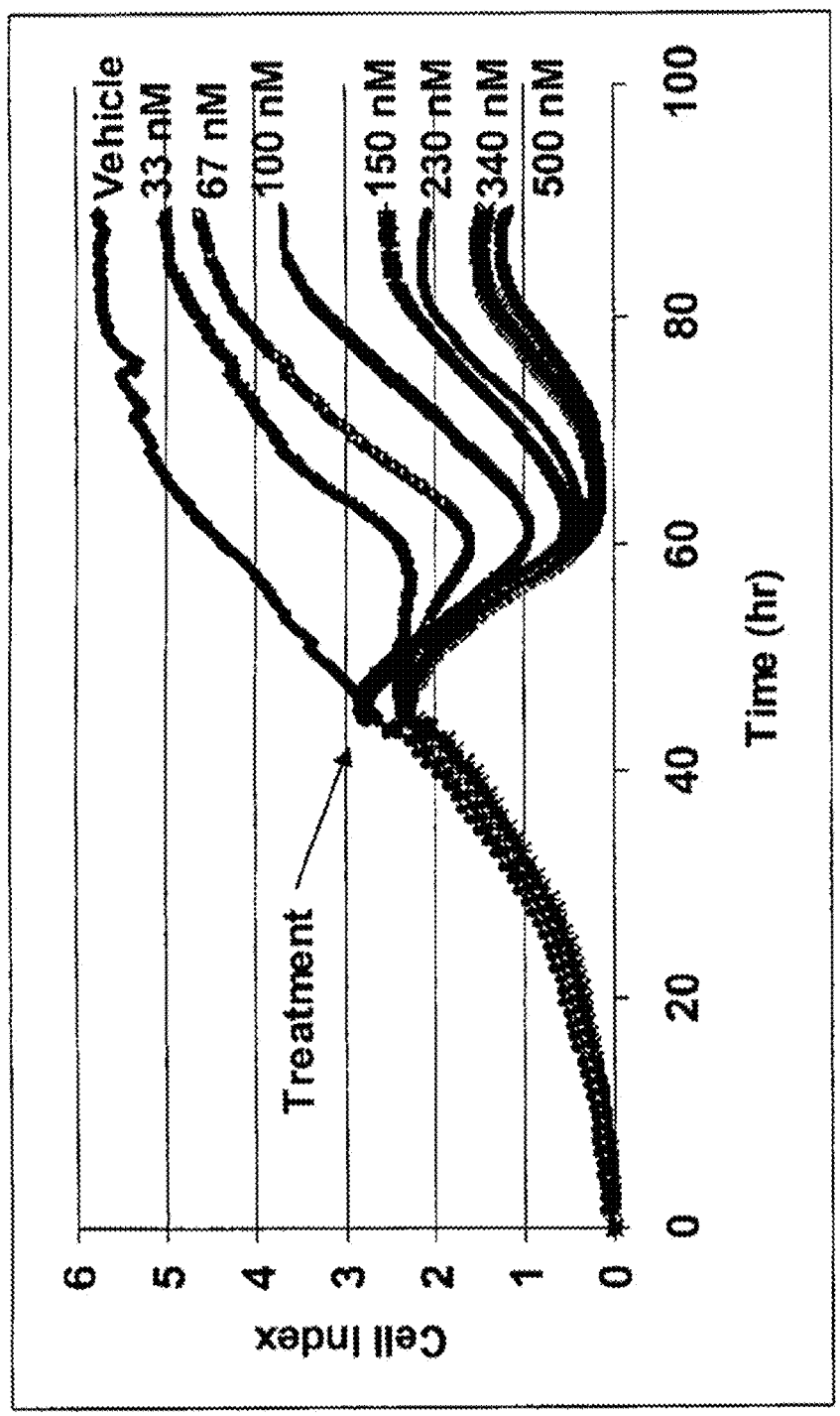
FIG. 5 shows time-dependent cell index for human non-small cell lung cancer cells (H460 cells) treated by anticancer drug paclitaxel. Different wells of cultured H460 cells were treated at their exponential growth phase with different concentrations of Paclitaxel. The dynamic response of the cells to different doses of paclitaxel was monitored in real time every 15 minutes for 50 hours after treatment using a cell-substrate impedance monitoring system. For paclitaxel concentration between 67 nM and 500 nM, H460 cells exhibited a gradual decrease in cell index initially after the compound addition. However, the cell index reached a minimum at a time dependent on the compound concentration between about 15 hours and 20 hours after compound addition. After that point, the cell index exhibited a gradual increase in cell index. The cell index for compound concentration of 33 nM exhibited a near-constant value for time up to about 15 hours after compound addition. After 15 hours following the compound addition, the cell index exhibited a gradual increase in cell index.

To demonstrate that dose dependent changes in cell-substrate impedance can be measured during the reaction of cancer cells to anticancer compounds, FIG. 5 shows curves that represent the time-dependent cell index for H460 cells treated with different concentrations of the anticancer drug paclitaxel. In this experiment, H460 cells were introduced into wells of a 16× cell-substrate impedance monitoring device (16× E-Plate). The device was positioned on a device station that was located in an incubator maintaining conditions of 37° C. and 5% $CO_2$. The cells were cultured and treated at their exponential growth phase with different concentrations of paclitaxel. The dynamic response of the cells to different doses of paclitaxel was monitored by monitoring cell-substrate impedance in real time every 15 minutes for 50 hours after treatment using a cell-substrate impedance monitoring system. The cell-substrate impedance monitoring system calculated the cell index at each time point monitored and plotted the cell index as a function of time. For paclitaxel concentrations between 67 nanomolar and 500 nanomolar, H460 cells exhibited a gradual decrease in cell index after compound addition. However, the cell index reached a minimum at a time dependent on the compound concentration, between about 15 hours and 20 hours after compound addition. After that point, there was a gradual increase in cell index in these wells. The cell index for compound concentration of 33 nanomolar exhibited a near-constant value for up to about 15 hours after compound addition. After 15 hours following compound addition, the cell index exhibited a gradual increase.

Figure 6:
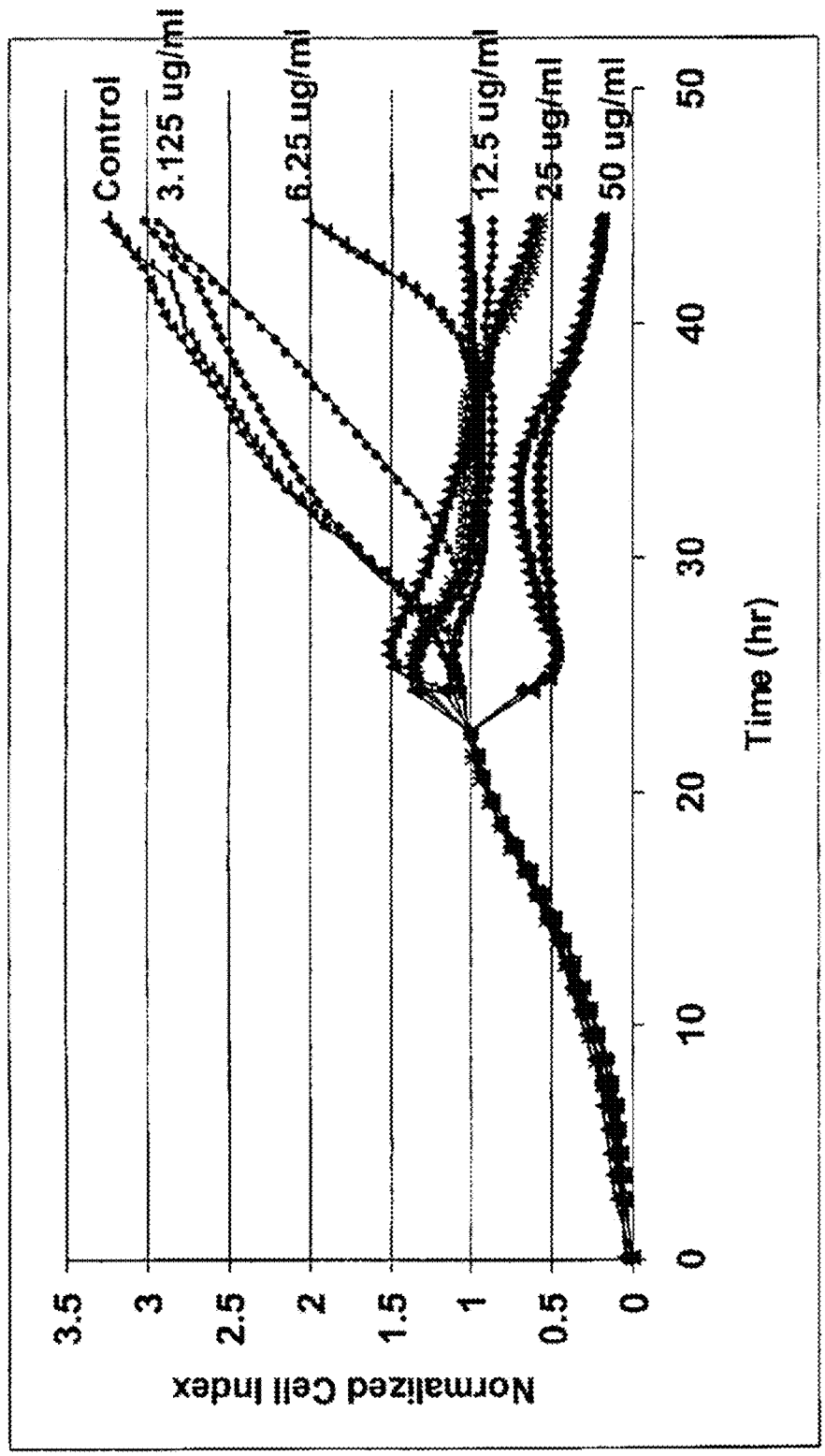
FIG. 6 shows time-dependent cell index for human non-small cell lung cancer cells (H460 cells) treated by anticancer drug AC101103. Different wells of cultured H460 cells were treated at their exponential growth phase with different concentrations of AC101103. The dynamic response of the cells to different doses of AC101103 was monitored in real time every 30 minutes for about 20 hours on a cell substrate impedance monitoring system. The time-dependent cell index in FIG. 6 is significantly different from those shown in FIG. 5. For compound concentrations at 3.125 µg/ml, 6.25 µg/ml and 12.5 µg/ml, the cell index exhibited a near-constant value for about 5 hrs, about 15 hrs and >20 hrs respectively. For compound concentrations at 3.125 µg/ml and 6.25 µg/ml, the cell index started to increase after about 5 hrs and about 15 hrs following compound addition. For the compound concentration of 25 µg/ml, there was a gradual, yet slow decrease in the cell index after compound addition. For the compound concentration of 50 µg/ml, there was an about 10 hr time period over which the cell index remained near-constant, and after that, the cell index decreased steadily.

FIG. 6 shows curves that represent the time-dependent cell index for H460 cells treated with anticancer drug AC101103. H460 cells were introduced into wells of a 16× cell-substrate impedance monitoring device (16× E-Plate). The device was positioned on a device station that was located in an incubator maintaining conditions of 37 degrees C. and 5% $CO_2$. The cells were cultured and treated at their exponential growth phase with different concentrations of AC101103. The dynamic response of the cells to different doses of AC101103 was monitored by measuring impedance in real time every 30 minutes for about 20 hours after treatment on the cell-substrate monitoring system.

Notably, the time-dependent cell index in FIG. 6 is significantly different from those shown in FIG. 5. For compound concentrations at 3.125 microgram/mL, 6.25 microgram/mL and 12.5 microgram/mL, the cell index exhibited a near-constant value for about 5 hrs, about 15 hrs and >20 hrs respectively. For compound concentrations at 3.125 microgram/ml and 6.25 microgram/ml, the cell index started to increase after about 5 hrs and about 15 hrs following compound addition. For the compound concentration of 25 microgram/mL, there was a gradual, yet slow decrease in the cell index after compound addition. For the compound concentration of 50 microgram/ml, there was an about 10 hr time period over which the cell index remained near-constant, and after that, the cell index decreased steadily.

Figure 7:
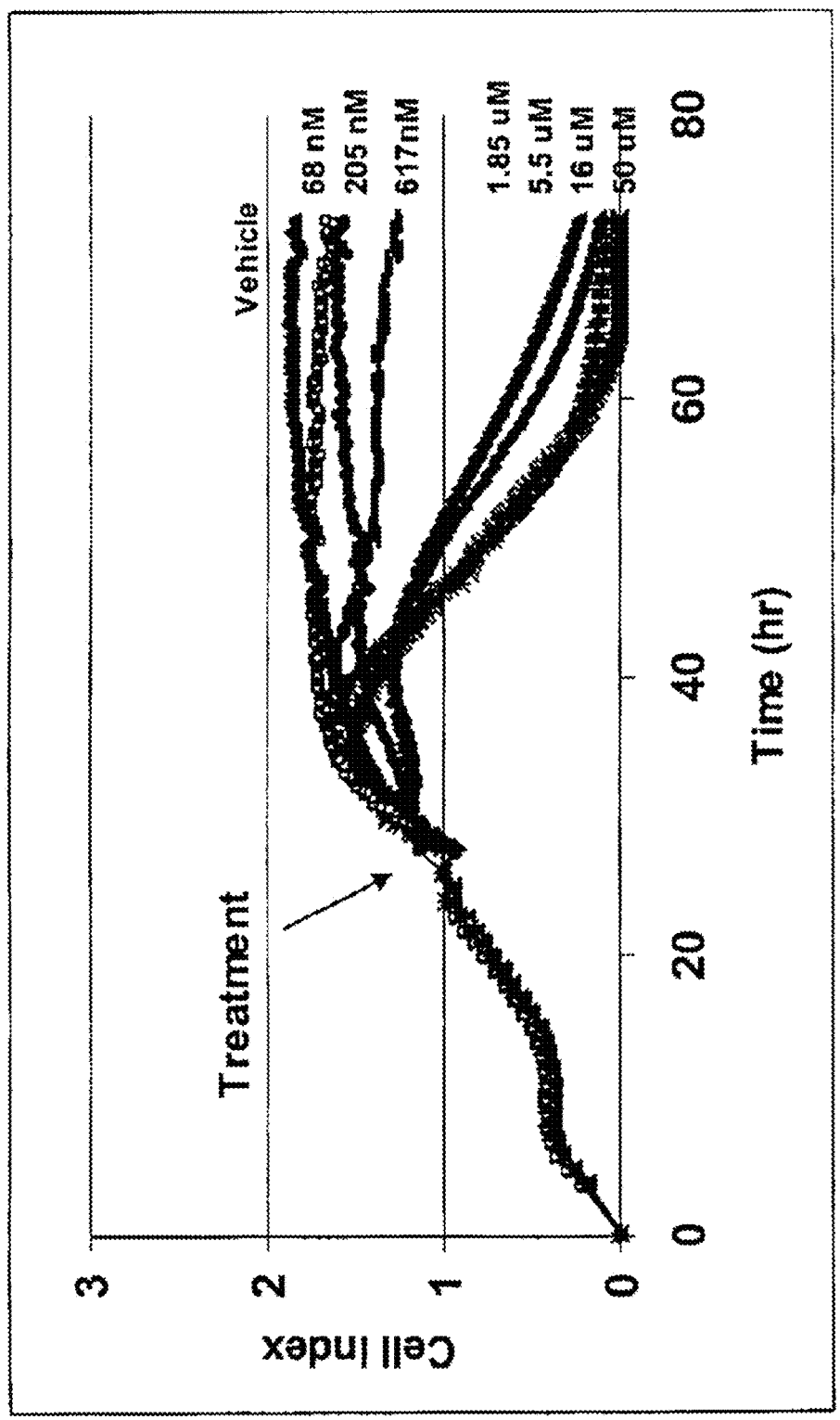
FIG. 7 shows dynamic drug response curves of adenocarcinomic human alveolar basal epithelial cells (A549 cells) treated with doxorubicin. 10,000 A549 cells were seeded in each well of a 16× device. The cell attachment and cell growth were monitored on the cell-substrate impedance monitoring system of the present invention in real time before treatment. When the cells were in exponential growth phase, doxorubicin at different concentration was added to the cells. Same volume of a solvent used for dissolve the drug was served as vehicle control. The time, and drug dose dependent cell response to doxorubicin was recorded in real time.
Figure 8:
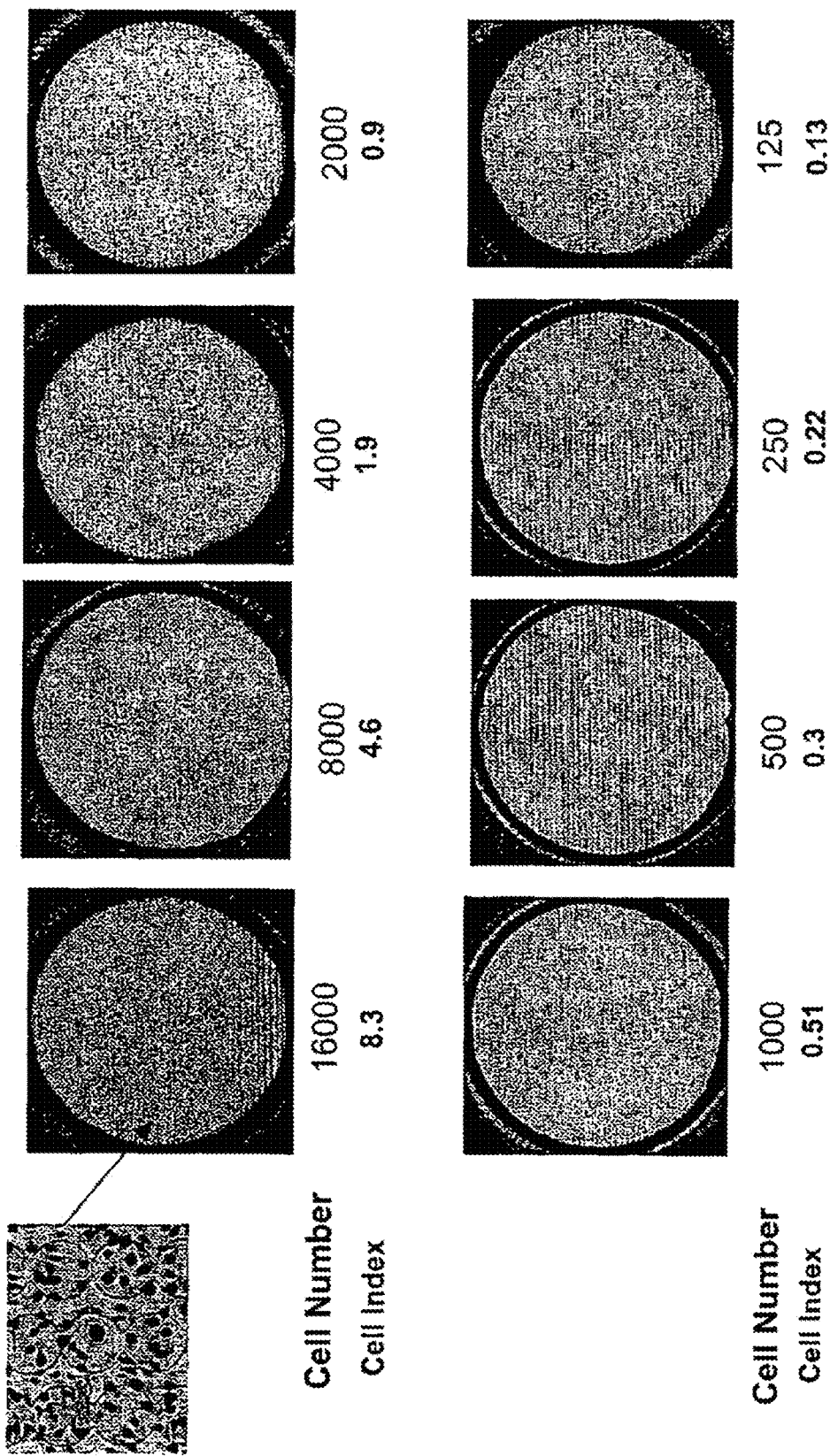
FIG. 8 shows the correlation of cell number and cell index of NIH3T3 cells on a cell-substrate impedance monitoring device. The indicated cell number of cells were seeded into microtiter devices fabricated with electronic sensor arrays substantially as shown in FIG. 1B. The electronic sensor arrays were-precoated with fibronectin. Two hours after seeding, the cell index number was determined using a cell-substrate impedance monitoring.
Figure 9A:
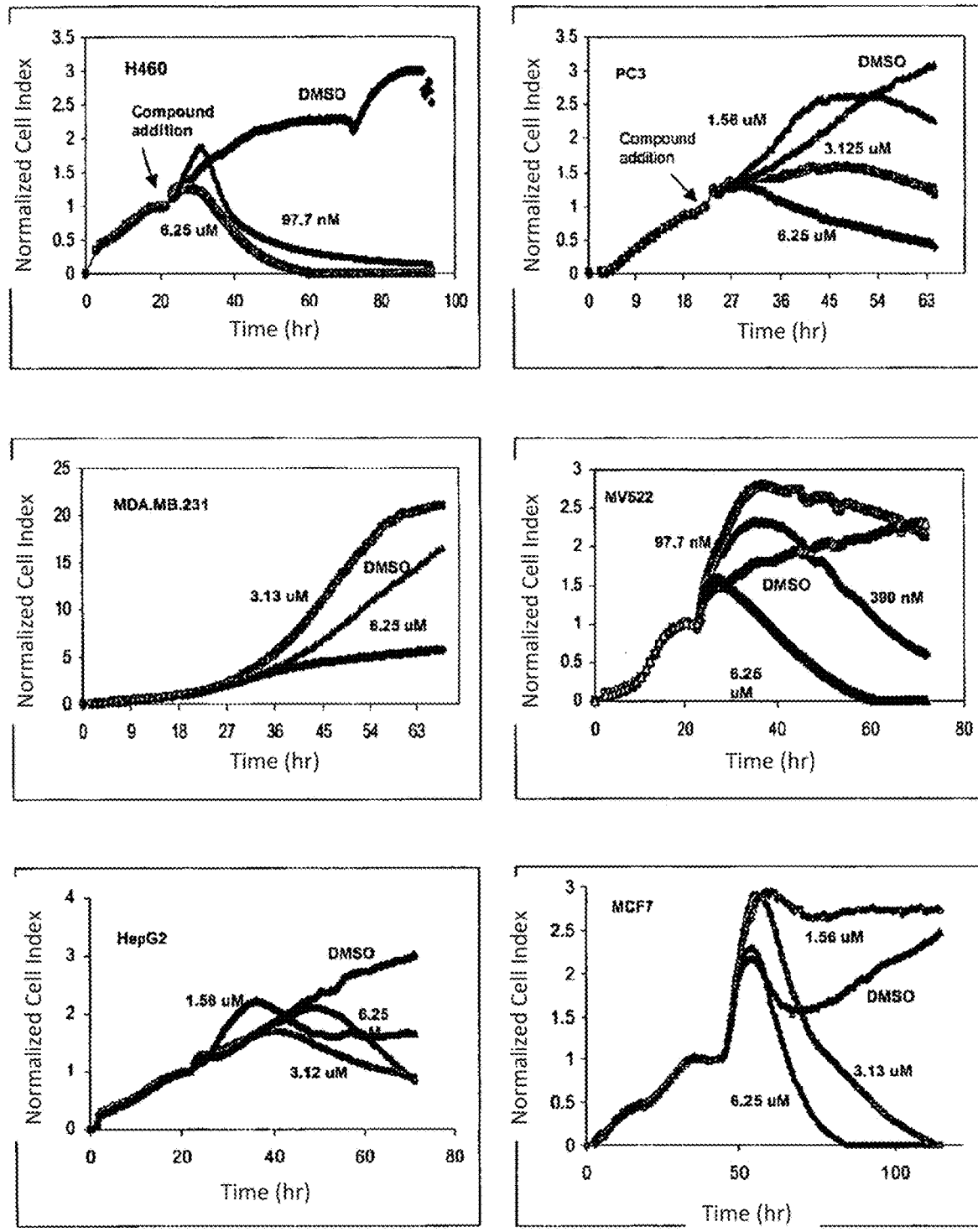
FIGS. 9A-B show responses of various cancer cell types (listed in TABLE 1) to doxorubicin treatment as monitored using a cell-substrate impedance monitoring system. The indicated cell lines were seeded onto microtiter devices fabricated with electronic sensor arrays. The cellular responses were continuously monitored at 15 or 30 or 60 minutes time interval before and after treatment with doxorubicin.
Figure 9B:
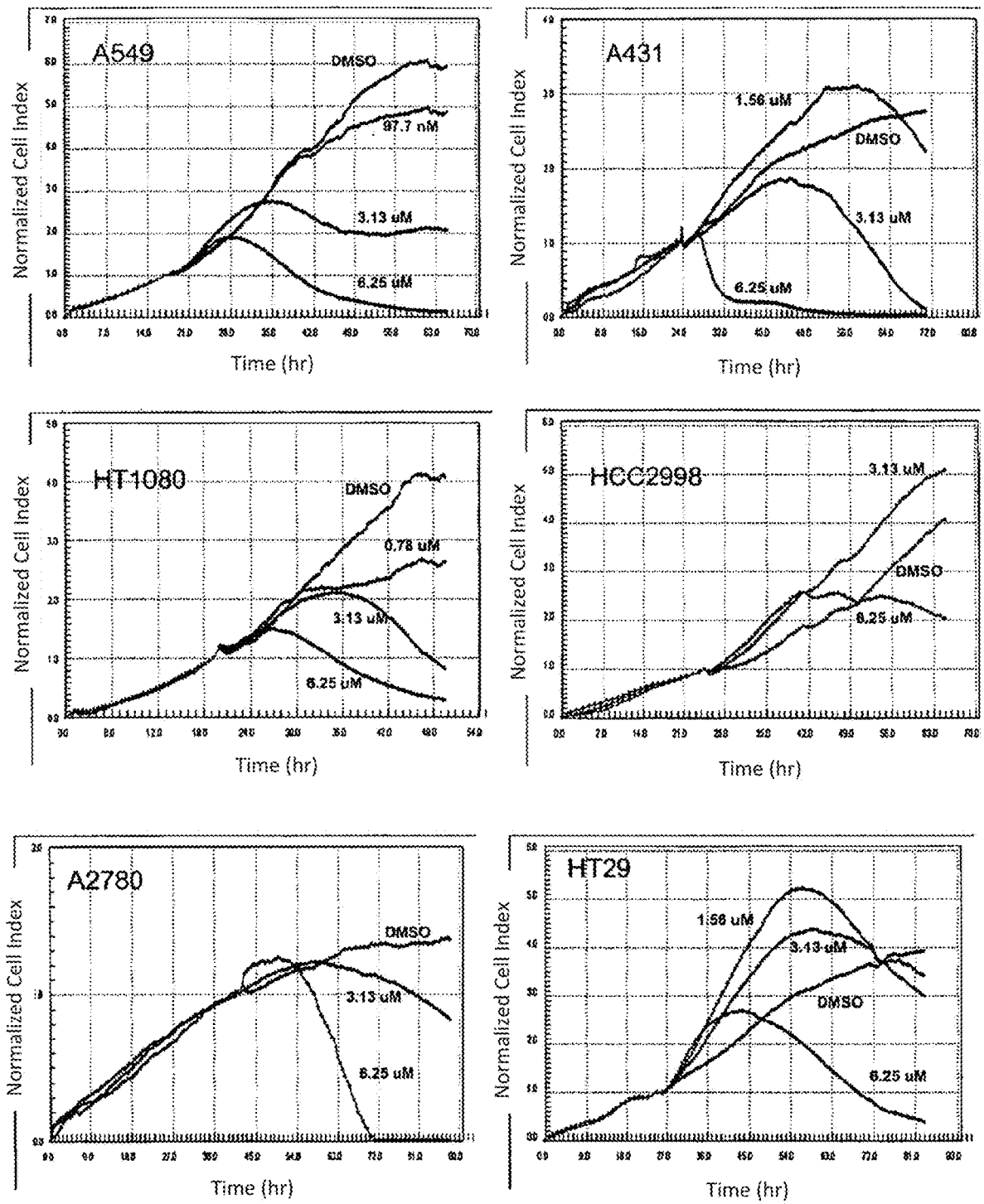
Figure 10A:
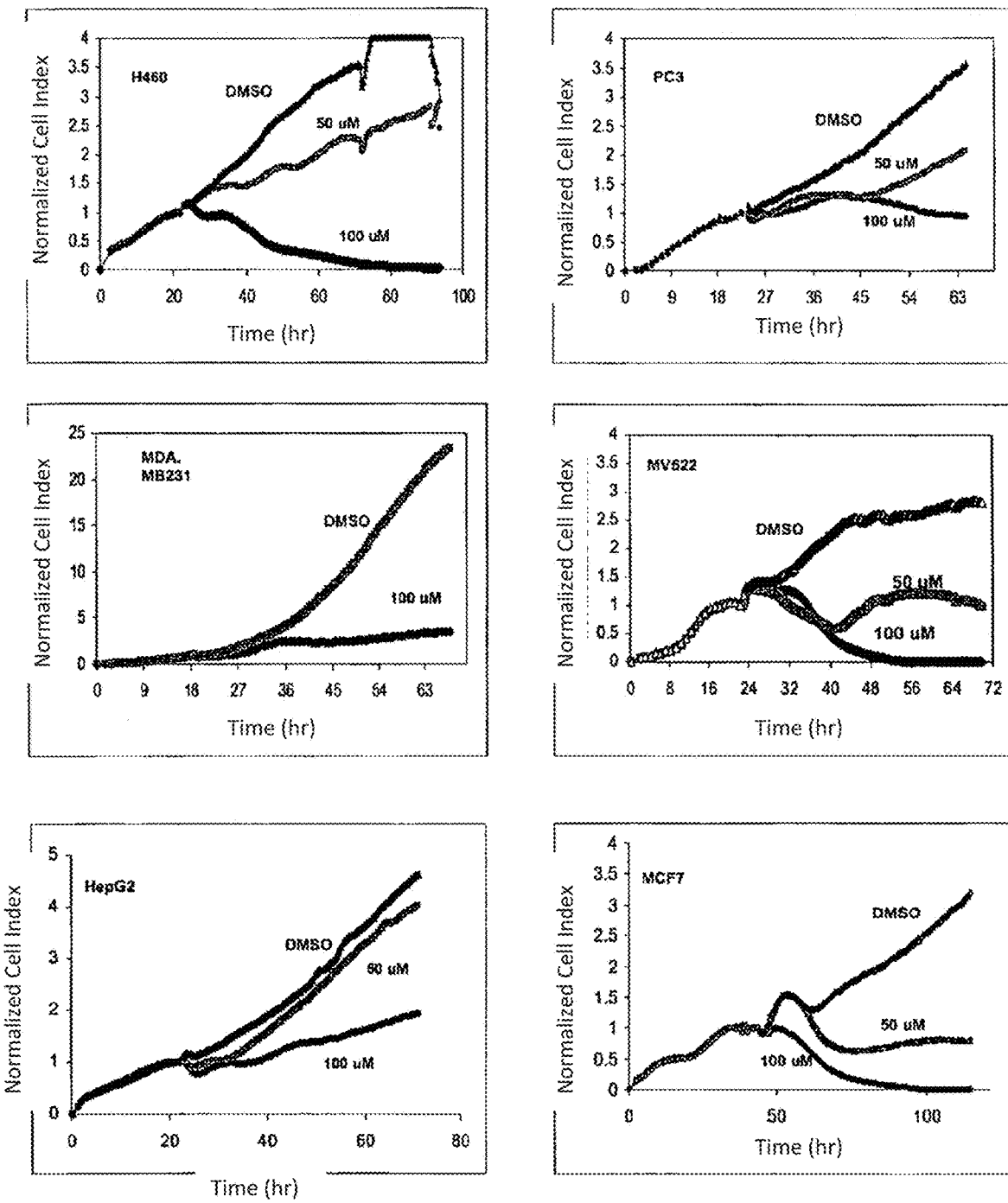
FIGS. 10A-B show responses of various cancer cell types (listed in TABLE 1) to olomoucine treatment as monitored using a cell-substrate impedance monitoring system. The indicated cell lines were seeded onto microtiter devices fabricated with electronic sensor arrays. The cellular responses were continuously monitored at 15 or 30 or 60 minutes time interval before and after treatment with olomoucine.
Figure 10B:
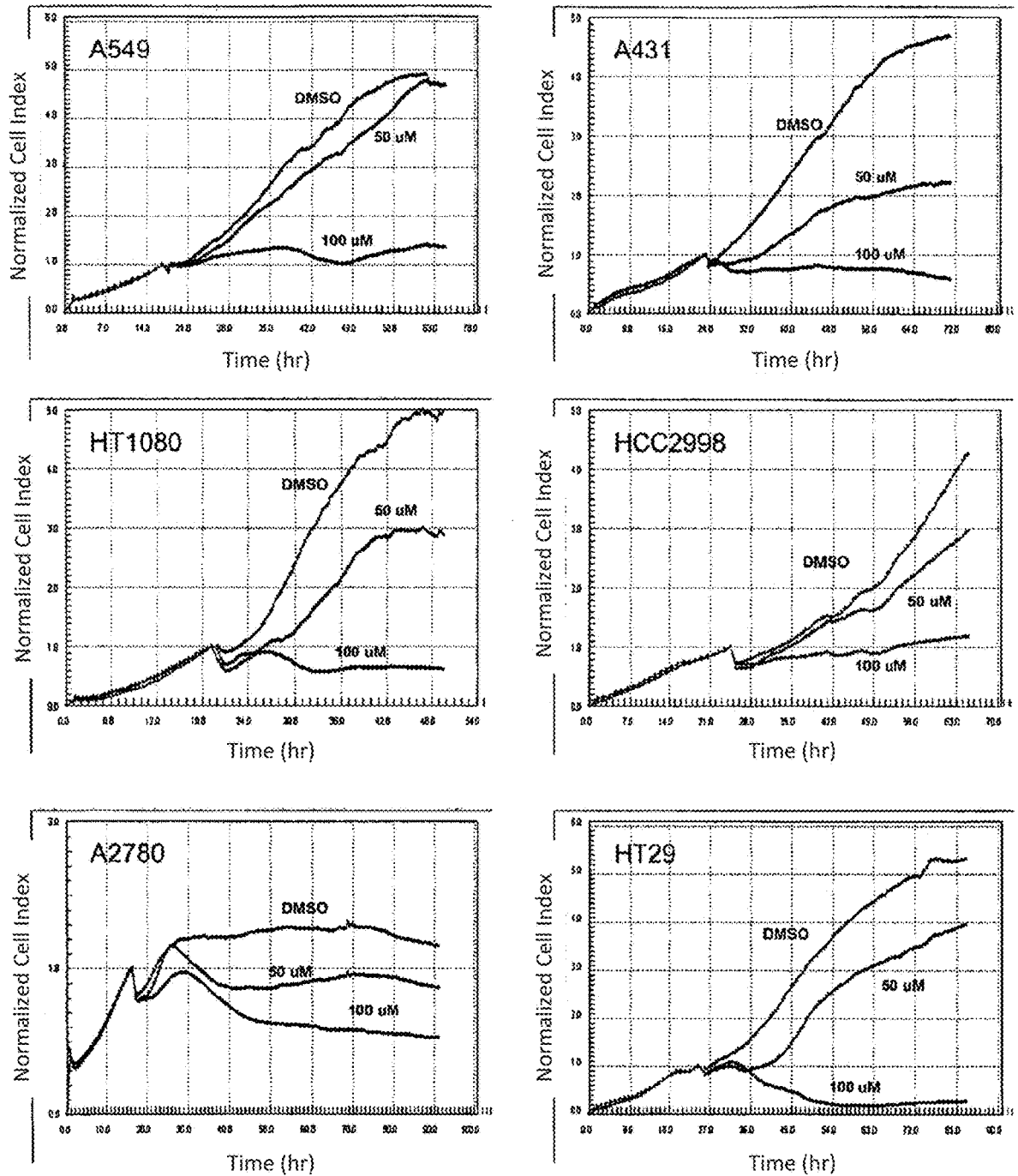
Figure 11A:
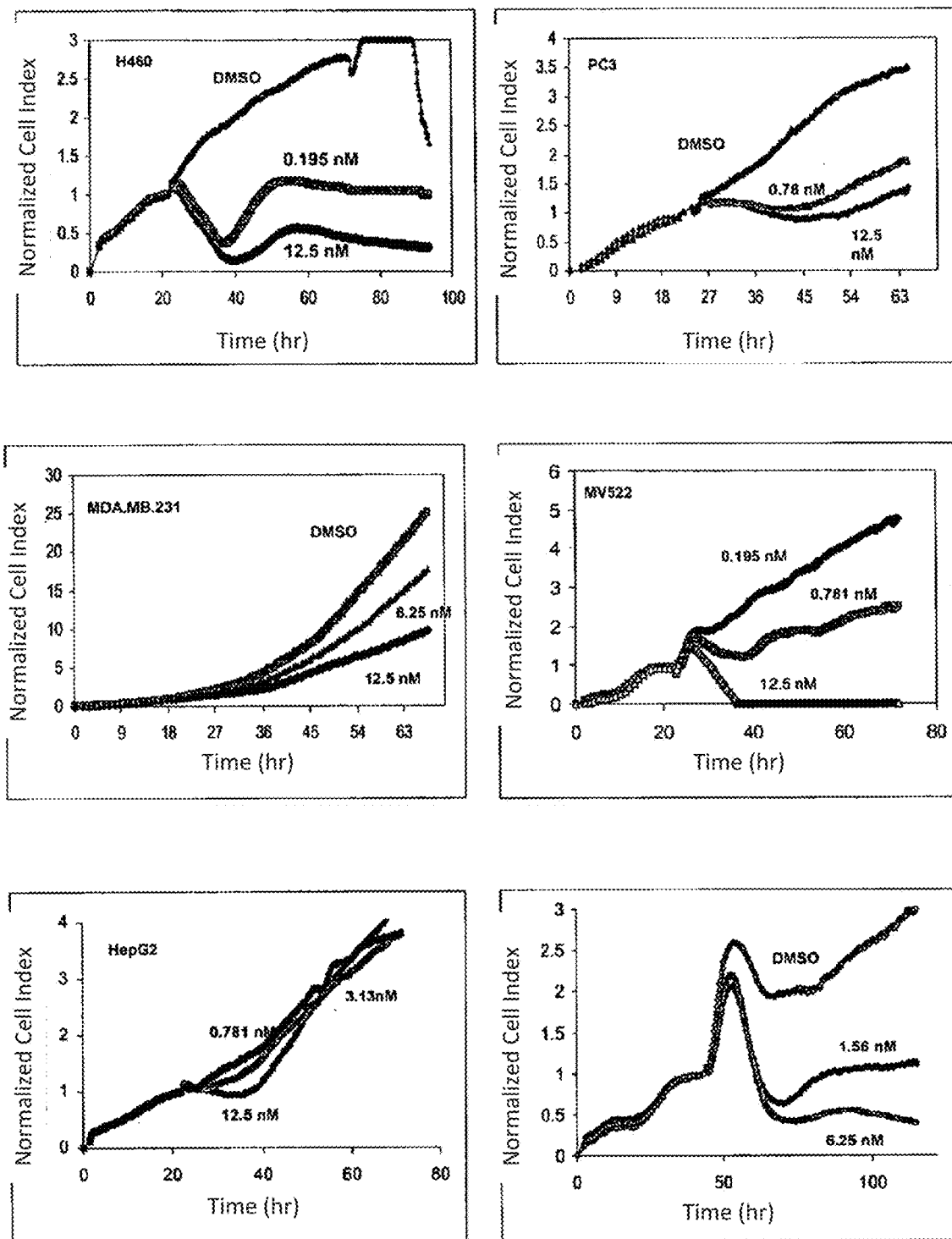
FIGS. 11A-B show responses of various cancer cell types (listed in TABLE 1) to paclitaxel treatment as monitored using a cell-substrate impedance monitoring system. The indicated cell lines were seeded onto microtiter devices fabricated with electronic sensor arrays. The cellular responses were continuously monitored at 15 or 30 or 60 minutes time interval before and after treatment with paclitaxel.
Figure 11B:
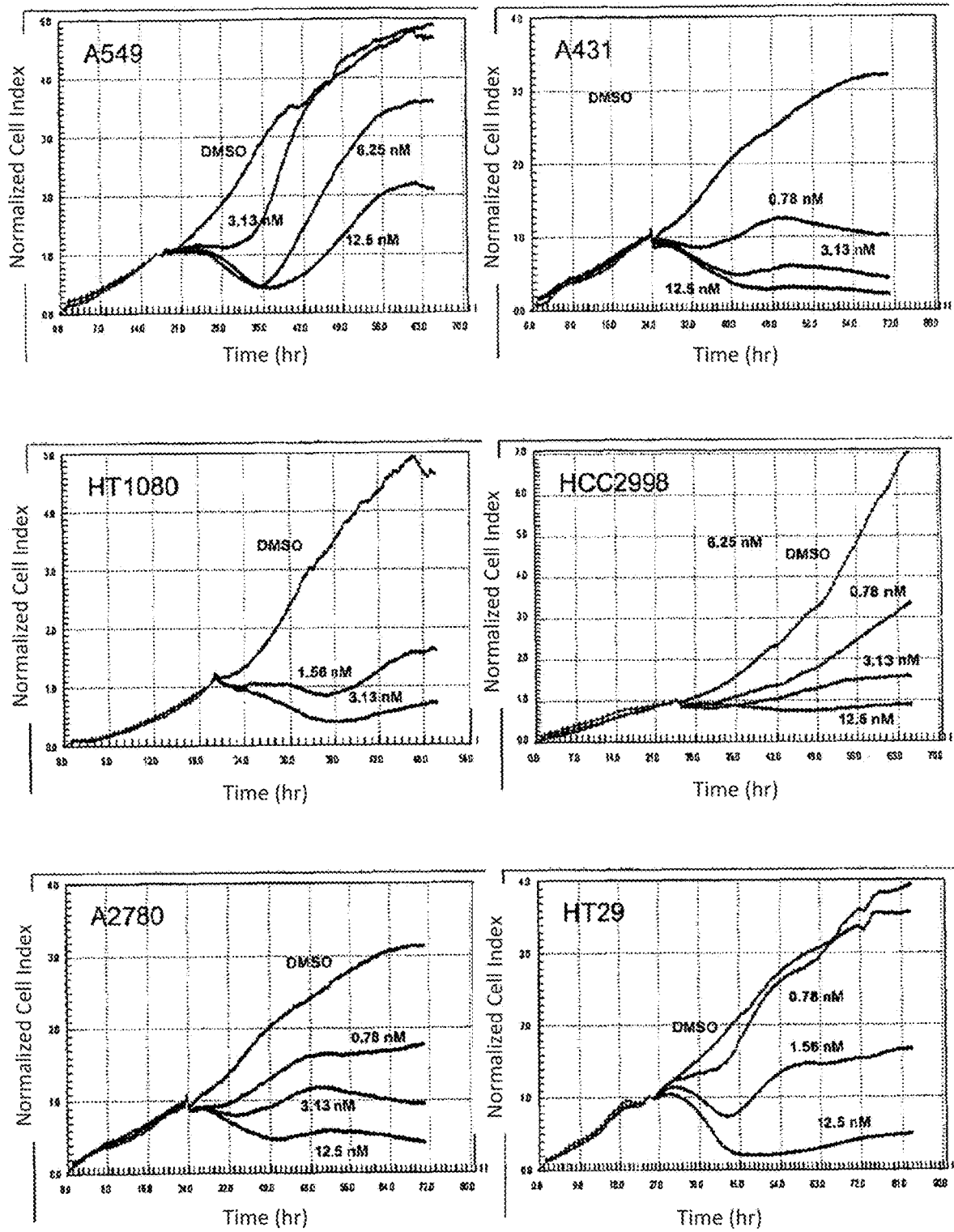
Figure 12A:
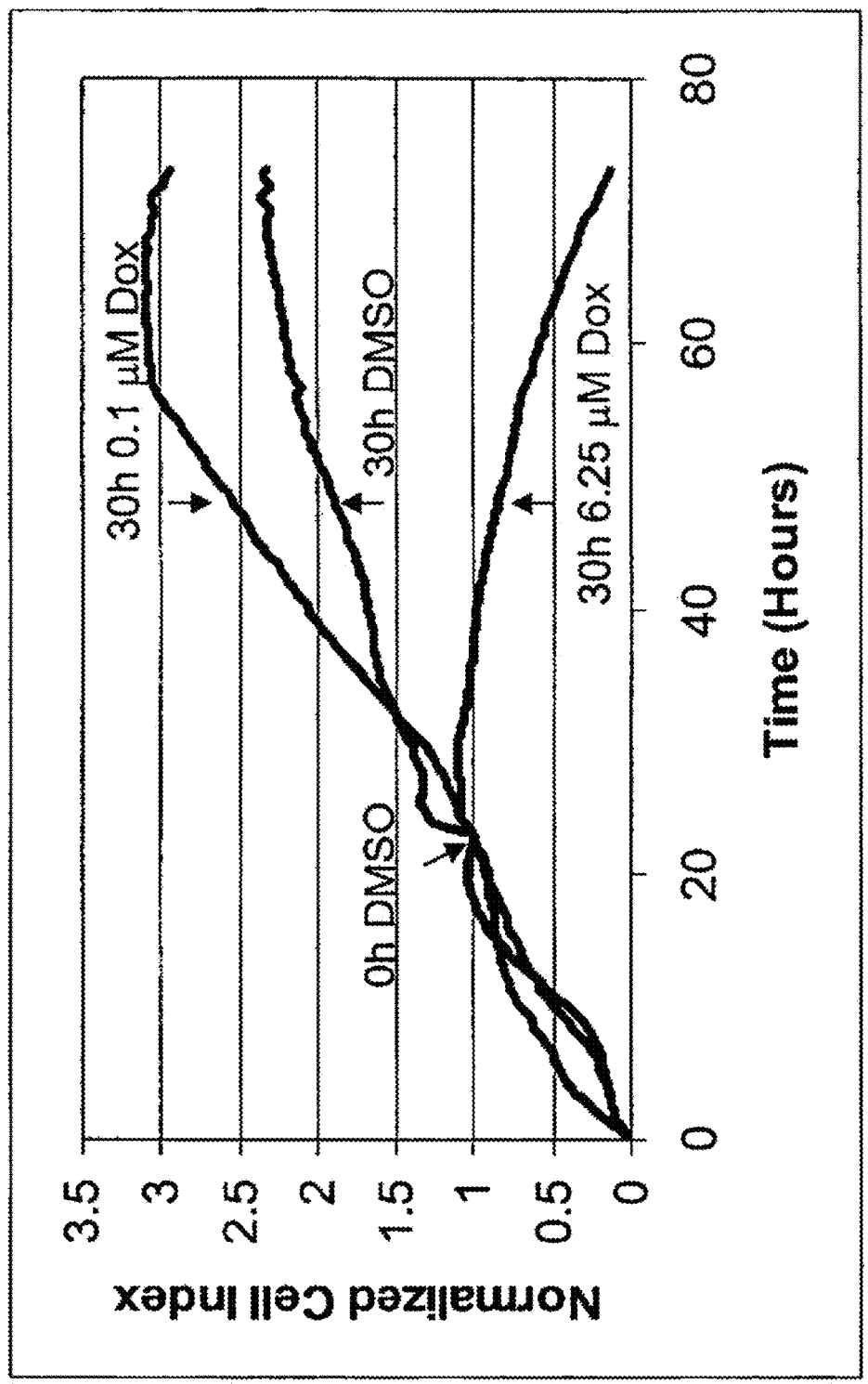
FIG. 12A shows the response of human colon adenocarcinoma cells (MV522 cells) to doxorubicin treatment as monitored using a cell-substrate impedance monitoring system. MV522 cells were seeded onto microtiter devices fabricated with electronic sensor arrays and were treated with either DMSO or doxorubicin at the indicated time and concentration.
Figure 12B:
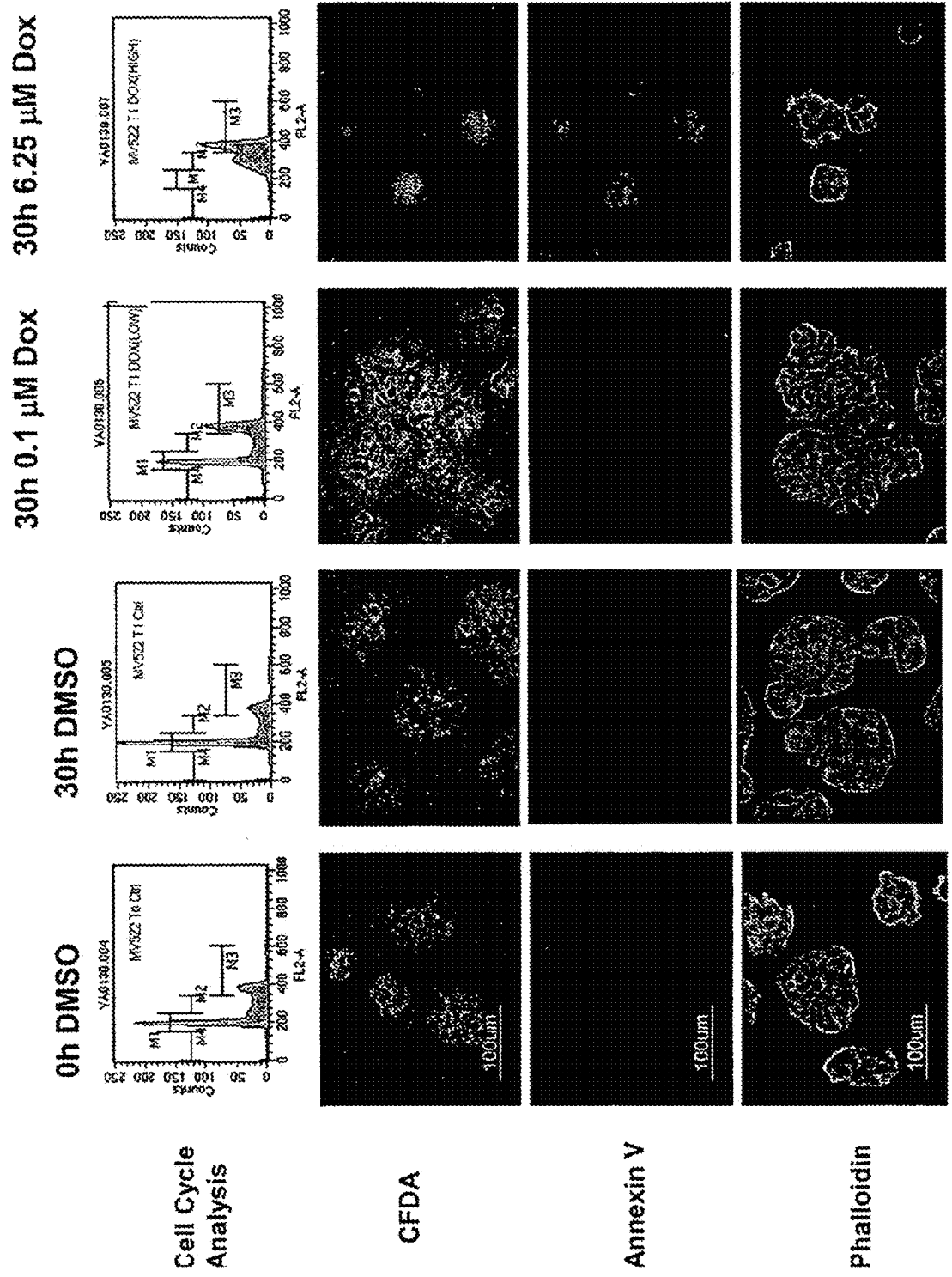
FIG. 12B shows the characterization of the cell biological effect of doxorubicin treatment on human colon adenocarcinoma cells (MV522 cells). The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 13A:
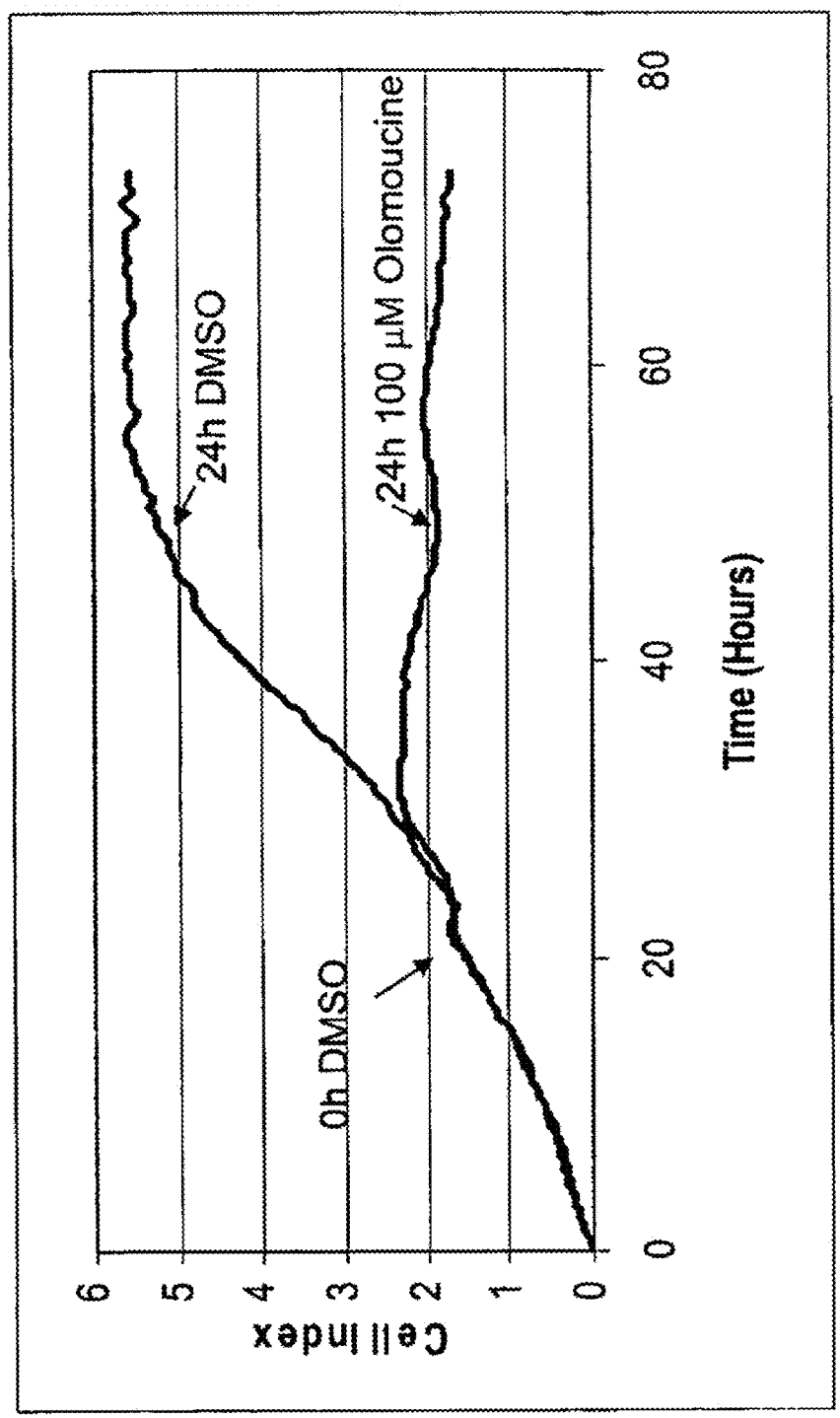
FIG. 13A shows the response of adenocarcinomic human alveolar basal epithelial cells (A549 cells) to olomoucine treatment as monitored using a cell-substrate impedance monitoring system. A549 cells were seeded onto microtiter devices fabricated with electronic sensor arrays shown in FIG. 1B and were treated with either DMSO or olomoucine at the indicated time and concentration.
Figure 13B:
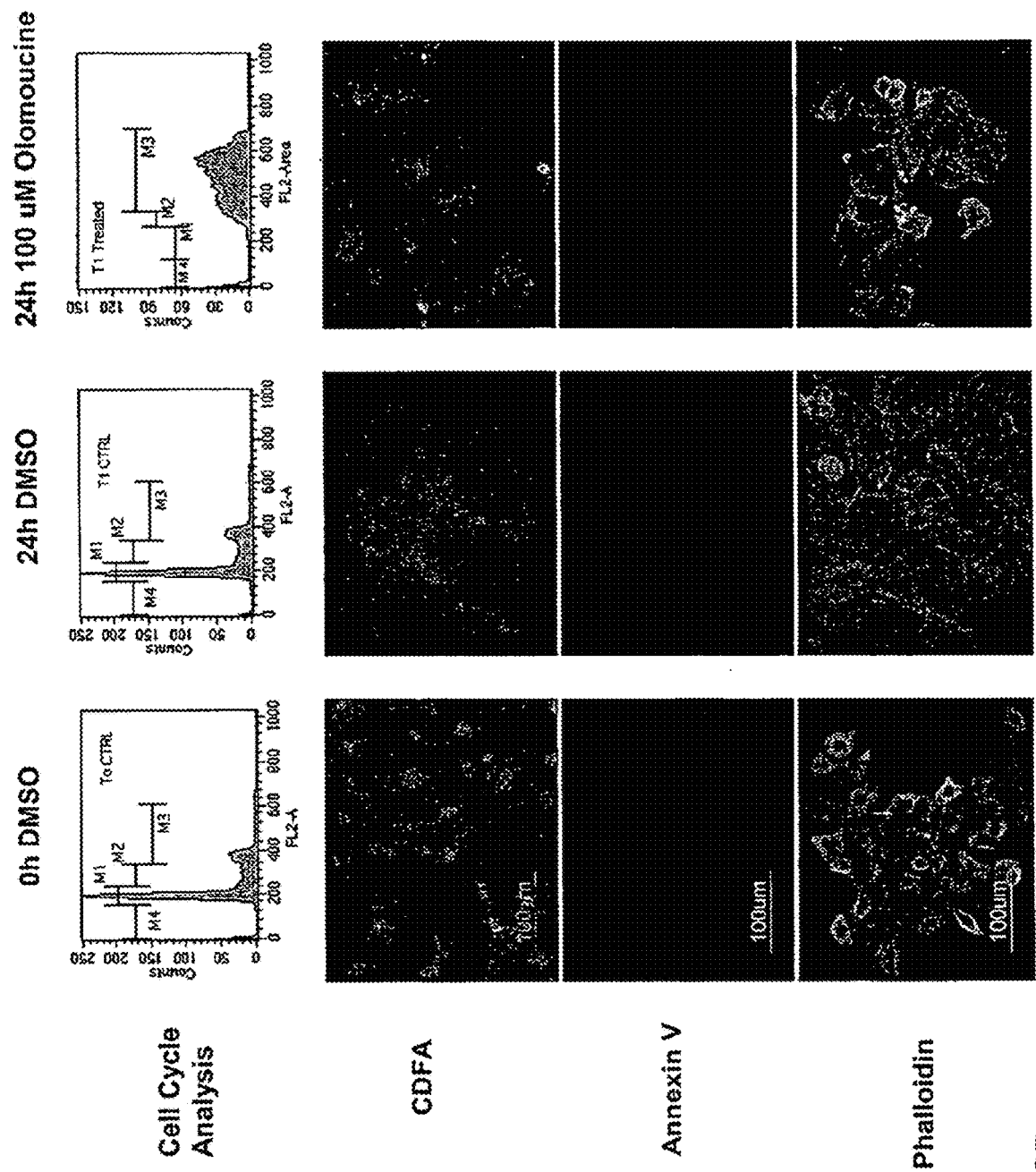
FIG. 13B shows the characterization of the cell biological effect of olomoucine treatment on human colon adenocarcinoma cells (MV522 cells). The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 14A:
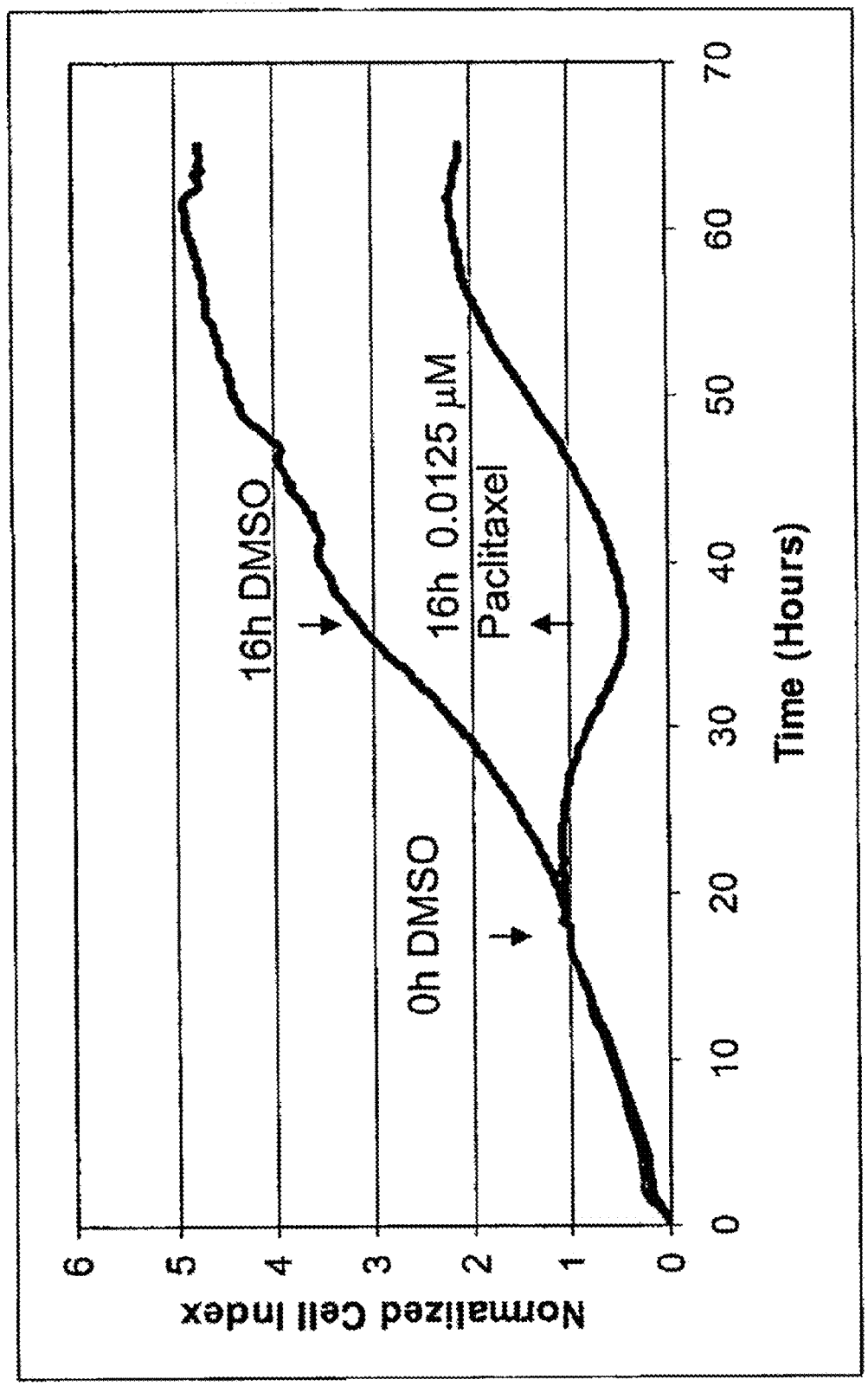
FIG. 14A shows the response of adenocarcinomic human alveolar basal epithelial cells (A549 cells) to paclitaxel treatment as monitored using a cell-substrate impedance monitoring system. A549 cells were seeded onto microtiter devices fabricated with electronic sensor arrays and were treated with either DMSO or paclitaxel at the indicated time and concentration.
Figure 14B:
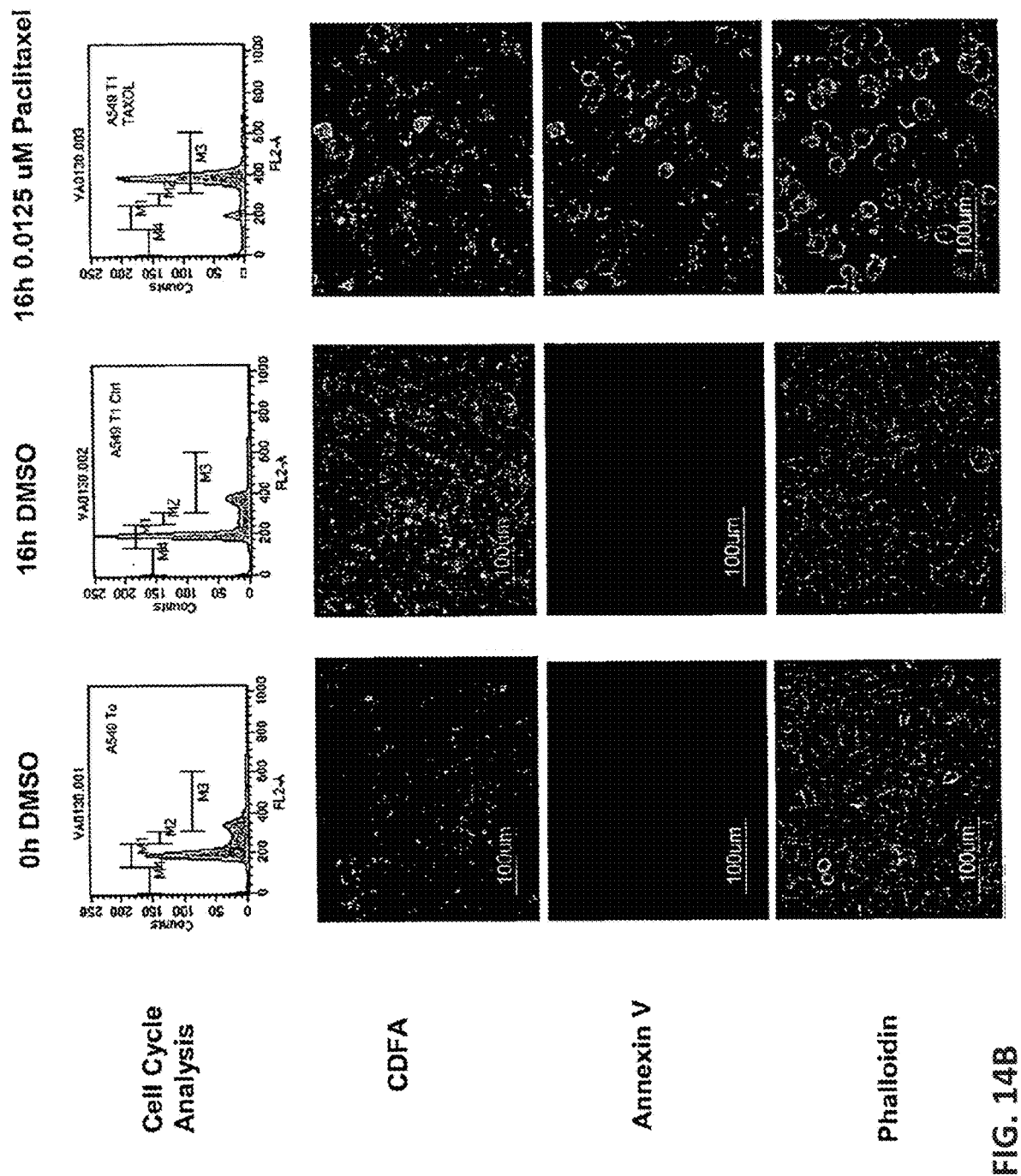
FIG. 14B shows the characterization of the cell biological effect of paclitaxel treatment on adenocarcinomic human alveolar basal epithelial cells (A549 cells). The cells were either processed for cell cycle analysis using FACS or treated with CFDA and Cy3-Annexin V to assess cell viability. In addition, the cells were fixed and stained with phalloidin to examine cell morphology. For viability and morphology, the cells were visualized and photographed using a fluorescence microscope equipped with CCD camera.
Figure 15A:
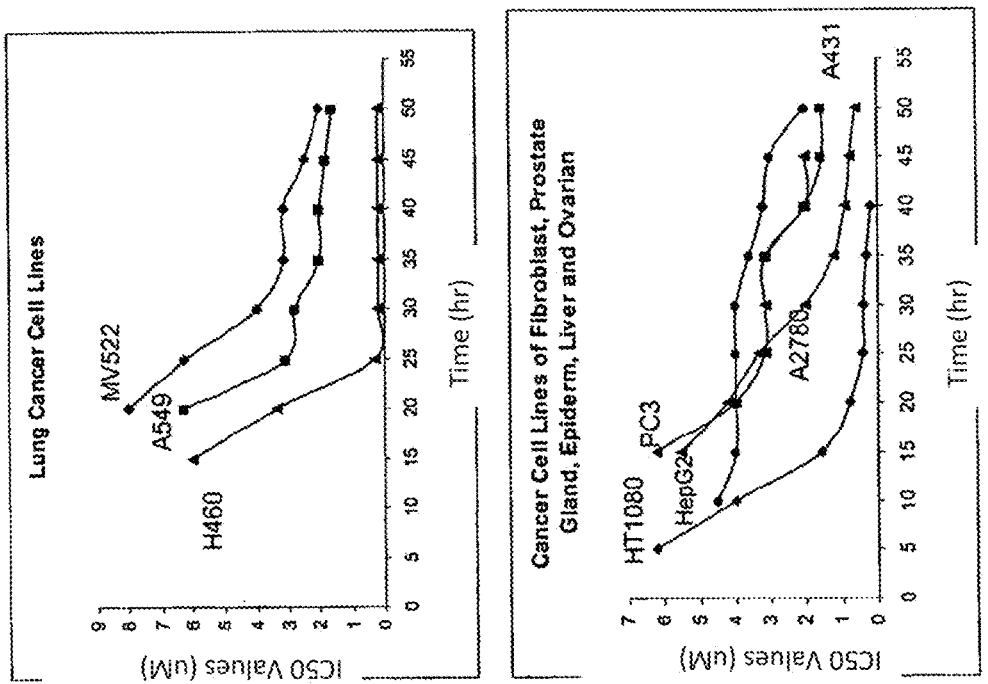
FIG. 15A-D are graphs depicting time dependent IC values for each compound (15A: Doxorubicin; 15B: Paclitaxel; 15C: Olomoucine; 15D: Tamoxifan) for cancer cell lines accepted as breast cancer, lung cancer, colon cancer, and fibrosarcoma, prostate cancer, epidermal cancer, liver cancer and ovarian cancer estimated at 5 hr intervals from the cell index curves obtained using a cell-substrate impedance monitoring system.
Figure 15A:
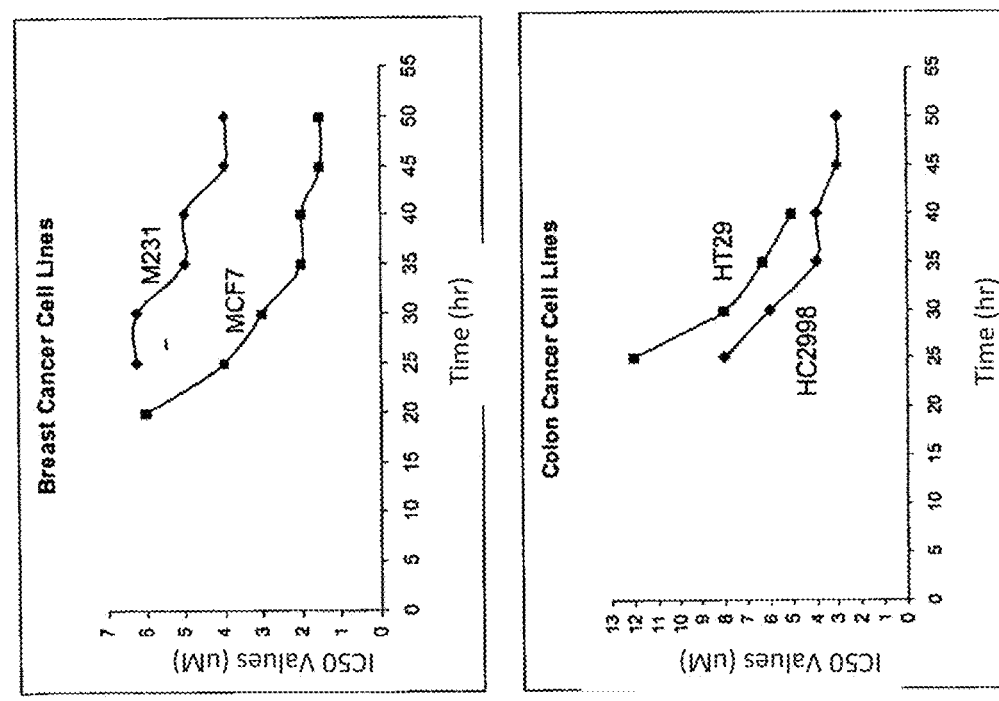
Figure 15B:
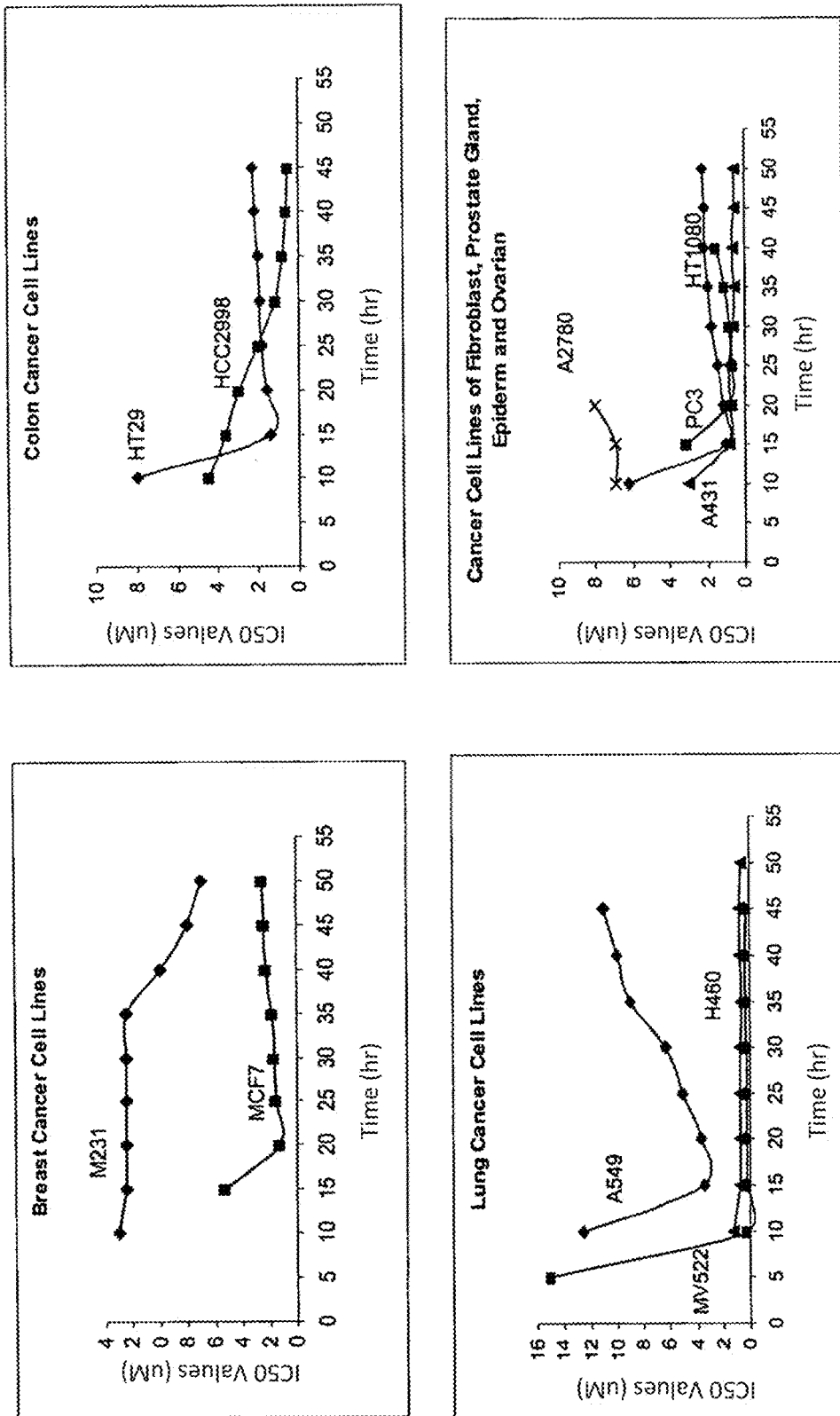
Figure 15C:
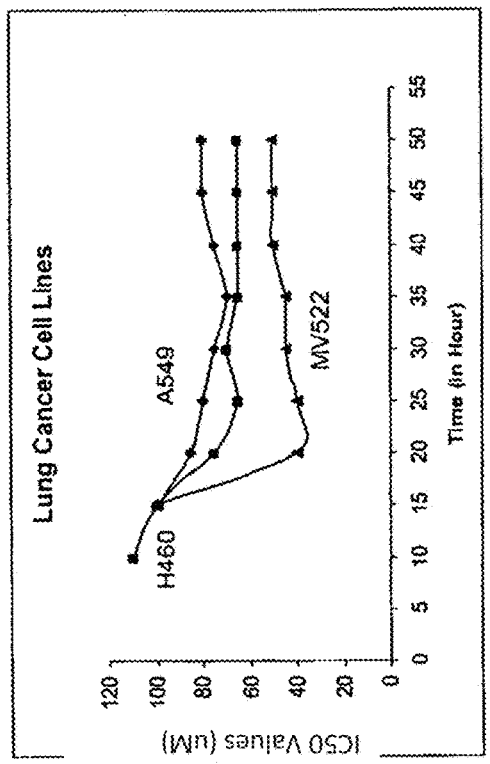
Figure 15C:
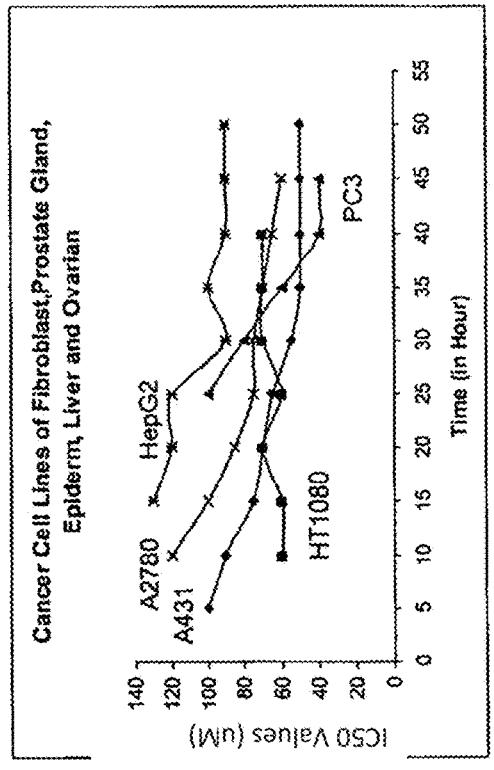
Figure 15C:
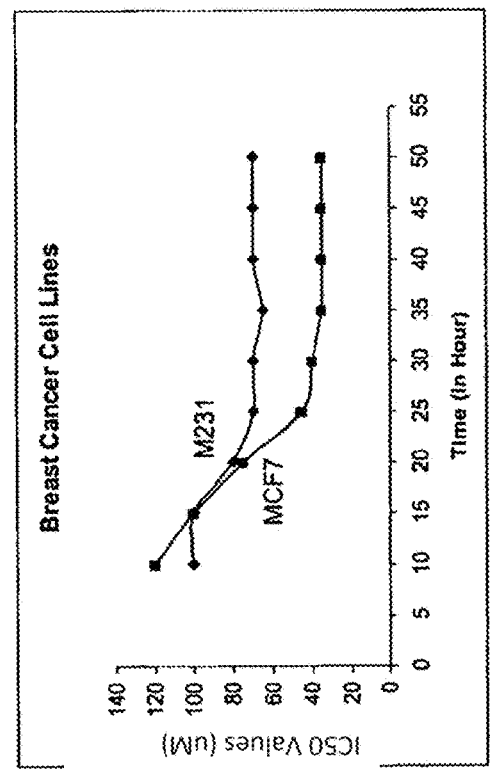
Figure 15C:
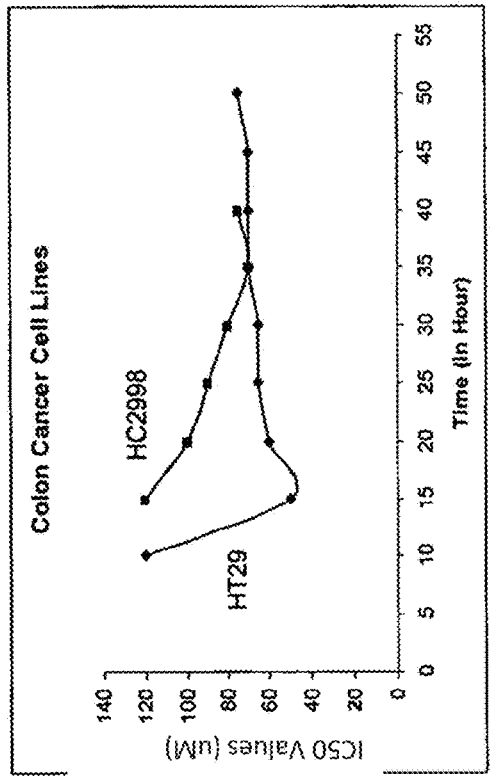
Figure 15D:
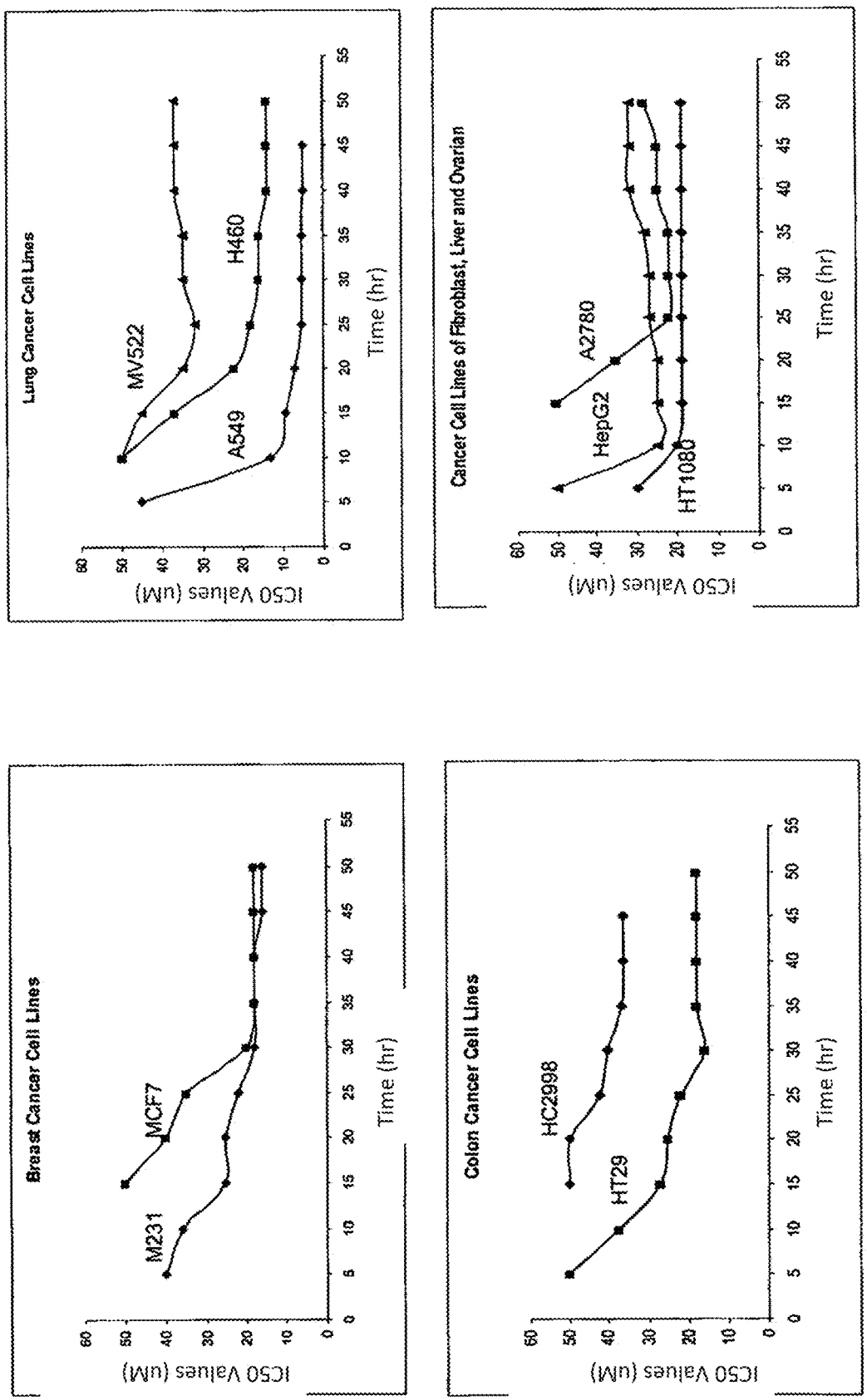

FIG. 7 shows dynamic drug response curves of A549 cells treated with doxorubicin. 10,000 A549 cells were seeded into each well of a 16× device (16× E-Plate). The device was positioned on a device station that was located in an incubator maintaining conditions of 37° C. and 5% $CO_2$. Cell attachment and cell growth were monitored on a cell-substrate impedance system in real time before treatment by monitoring impedance at regular intervals. When the cells were in exponential growth phase, doxorubicin at different concentrations was added to the wells. The same volume of the solvent used to dissolve the drug was added to some wells as a control. The time, and drug dose dependent cell response (calculated as cell index) to doxorubicin was recorded in real time on the cell-substrate impedance monitoring system as shown in this figure.

Figure 3:
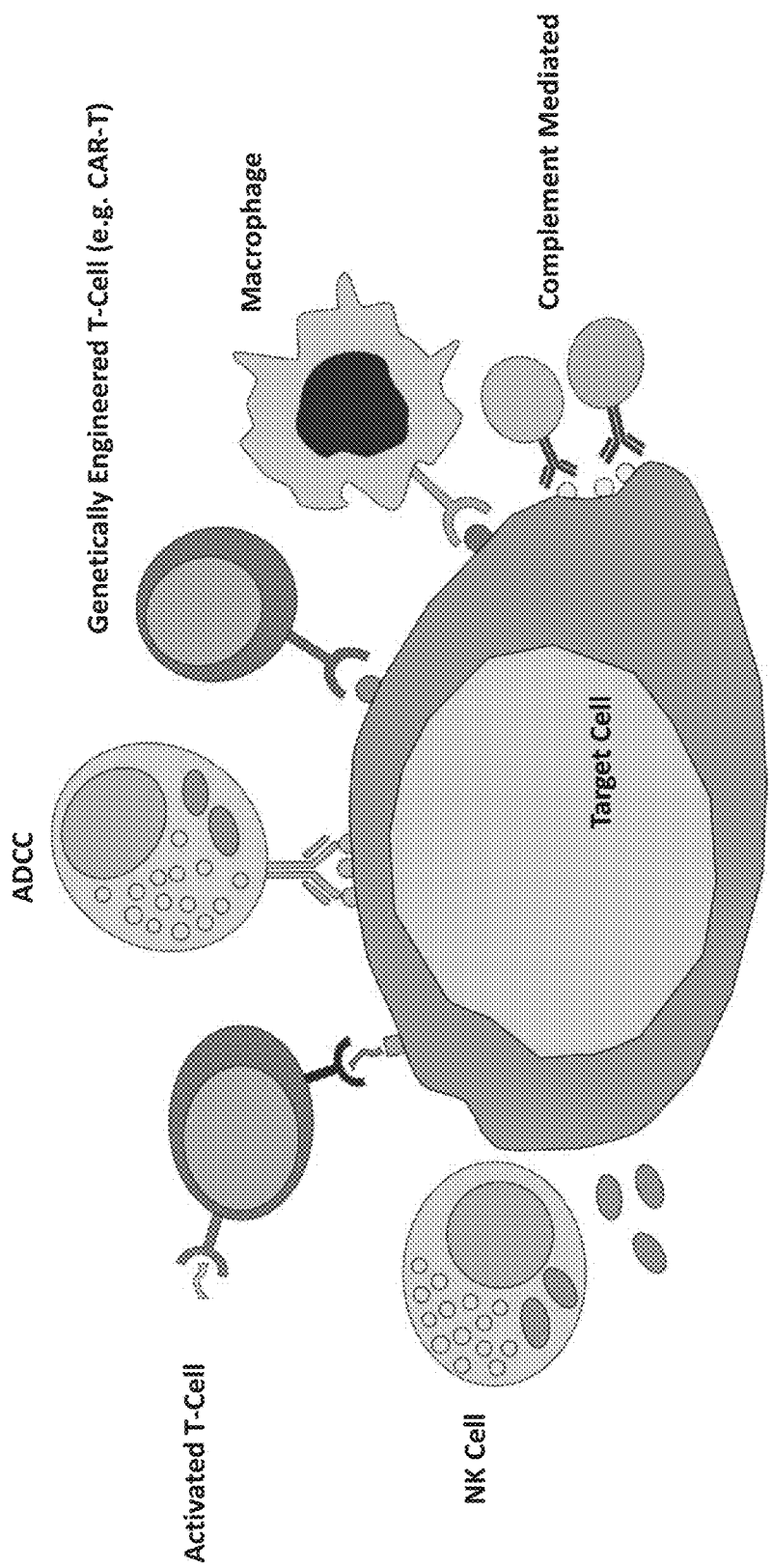
FIG. 3 shows different approaches to immune-mediated tumor cell killing that can be monitored using cell-substrate impedance technology.

Although experiments summarized above demonstrate cell-substrate impedance can be used to monitor changes in cancer cell populations in response to administration of anticancer compounds directly, the invention also determines the effectiveness of cancer cell killing in response to the presence of effector cells. FIG. 3 provides an overview of different effector cells that may be added to the wells of the device to assess cancer cell killing.

Prior to and after adding effector cells to wells containing target cells, cell-substrate impedance should be measured. Since the effector cells are suspended in the well they do not substantially interfere with the sensor electrodes in the well. Therefore, the change in impedance in response to the addition of effector cells is almost entirely due to the changes in the target cell population.

Effector cells may be any cell capable of killing or lysing a target cell, or presenting or marking a target cell for lysis by another effector cell, such as by marking the surface of the target cell with an antibody. As non-limiting examples effector cells may be Natural Killer (NK) cells, Cytotoxic T-Lymphocytes (CTLs), neutrophils, easonophils, macrophages, Natural Killer T (NKT) cells, B-cells, T-cells, genetically modified T cells or NK cells and a cell type having cytolytic activity. Further, T cells can be any selected from the group consisting of T helper cells (Th cells), cytotoxic T cells, and memory T cells.

As such, the methods provide an approach to determine cytotoxic activity of effector cells on target cells by determining antibody-dependent cellular toxicity (ADCC), BiSpecific Antibody-mediated cellular cytotoxicity, CAR-T-mediated cellular cytotoxicity, complement-mediated cellular cytotoxicity, complement-dependent effector cell-mediated cellular cytotoxicity and other cytoxicity relying at least in part on effector cells.

In some embodiments, the effector cells are further engineered to increase expression of an exogenous compound, such as but not limited to Interleukin 2, to promote growth, proliferation or persistence of the effector cells. Effector cells may be added to one or more wells or fluid containers at a predetermined ratio to the target cells. One skilled in the field of immunology would be able to provide or determine the appropriate ratio (or ratios) of effector cell to target cell.

The present invention also provides for the addition of a compound or factor capable of activating, deactivating or stimulating effector cells. Such compounds may vary depending on the effector cell but may include lipopolysaccharide (LPS), an antibody, an accessory compound, a compound obtained or screened from a library of compounds and the others. Thus, the compound or factor may be any suitable compound or factor used in the biological arts for stimulation of an effector cell. As non-limiting examples the compound may be a monoclonal antibody, a polyclonal antibody, a peptide, a protein, a lipid, a biomolecule, a nucleic acid molecule, a naked DNA molecule and others. A variety of antibodies may be obtained or provided for the present invention such as but not limited to IgG, IgM, IgE, IgA as well as heavy chain portions, light chain portions including kappa and lambda light chains, Fc portions, Fab portions, Fab'2 portions and the like. Antibodies may be humanized or may be cross-species.

Similarly additional cell types or cell lines may be provided with effector cells. Such cells include but are not limited to accessory cells.

In some embodiments, a check point inhibitor is added to the well to increased effectiveness of cancer cell killing. Check point inhibitors seek to overcome one of cancer's main defenses against an immune system attack by blocking normal proteins on cancer cells. Examples of check point inhibitors include antibodies or antibody fragments targeting PD1, CTLA-4, CD137, OX40, CD27, CD40L, TIM3 on the surface of effector cells or their respective cognate ligand on the surface of target cells.

Antibody-dependent cell-mediated toxicity (ADCC) is a mechanism of cell-mediated immune defense, where an effector cell of the immune system actively lyses a target cell, whose membrane-surface antigens have been bound by specific antibodies. In humans, ADCC is usually mediated by IgG. Classical ADCC is mediated by natural killer (NK) cells; but macrophages, neutrophils, and easonophils can also mediate it. ADCC is part of the adaptive immune response due to its dependence on a prior antibody response.

A specific receptor for the constant region of IgG, called FcγRIII is expressed on the NK cell membrane and mediates activation of NK cells and subsequent ADCC. ADCC is the dominant component of the activity of antibodies against tumors. It is believed that certain tumors bear antigens which are recognized by the humoral immune system. The subsequent interaction of the antibody with the antigen on tumor cells will mark the tumor cells for demise by the innate immune components such as NK cells.

Accordingly, a method of screening for antibody-dependent cellular toxicity (ADCC) is provided, which includes providing a cell-substrate impedance monitoring device operably connected to an impedance analyzer, wherein the device comprises a well for receiving cells and an electrode array at a base of the well; adding target cells characterized as cancer cells to the well; adding a proposed therapeutic capable of interacting with the target cells to the well; adding effector cells to the well; monitoring cell-substrate impedance of the well before and after adding effector cells and optionally deriving impedance-based parameters from the impedances; and determining effectiveness of effector cell killing of the target cells by comparing the impedances or impedance based parameters over time. Comparison can be way of comparing the impedance or impedance-based parameter to a same well or to a positive or negative control well. As with the embodiments above, preferably the effector cells are from a same subject as the cancer cells.

In some embodiments, the proposed therapeutic is a bispecific engager. As such, the step of adding the proposed therapeutic could be further characterized as adding a bispecific engager to the well having target cells to form a test well, wherein the bispecific engager is a molecule configured to bridge the effector cells to the target cells. The bispecific engager refers to two polypeptides linked together, in which one polypeptide binds either effector cell or target cell and the other peptide binds the remaining effector cell or target cell thereby joining the effector cells to the target cells. Bispecific engagers can be used with macrophages, neutrophils, and easonophils. However, preferably the bispecific engager is a bispecific T-cell engager (BiTe) that binds T-cells to the cancer cells.

As such a method of assessing cytolytic activity on cancer cells can include providing a cell-substrate impedance monitoring device operably connected to an impedance analyzer, wherein the device comprises a well for receiving cells and an electrode array at a base of the well; adding target cells characterized as cancer cells to the well; adding effector cells to the well, wherein the effector cells are immune cells, optionally from a same patient as the target cells; adding a bispecific engager to the well to form a test well, wherein the bispecific engager is a molecule configured to bridge the effector cells to the target cells; monitoring cell substrate impedance of the test well over time, including before and after the step of adding the bispecific engager, and optionally deriving impedance-based parameters from the impendences; and determining the effectiveness of effector cell killing in response to the bispecific engager by comparing the impedances or impedance based parameters over time.

Exemplary target cells are circulating tumor cells (CTCs) collected from blood or tumor cells, optionally collected from a tissue biopsy. Cancer cells can be obtained from a number of different biological samples, such as a solid tumor, a haematopoietic tumor, blood, and pleural effusion.

The effector cells can be natural killer cells (NK cells), macrophages, neutrophils, eosinophils, T-cells, or B-cells. When the effector cells are T-cells, the T cells are selected from one or more of the group consisting of T helper cells (Th cells), cytotoxic T cells, and memory T cells.

In preferred the bispecific engager binds a T-cell surface moiety (referred to as BiTe), optionally cluster of differentiation 3 (CD3). BiTe are modified forms of antibodies which have two distinct domains. One domain recognizes a specific antigen expressed in target cells such as tumor cells and the other domain recognizes and binds to the CD3 subunit of the T cell receptor complex. By binding to the CD3 subunit, the modified antibodies activate CD3 expressing immune cells such as cytotoxic T lymphocytes and facilitates the destruction of the target cell by the immune cells.

In some embodiments the impedance based parameter is a cell index or a normalized cell index that is normalized to a time point before adding the bispecific engager. In some embodiments the impedance based parameter is an impedance-based curve, in further embodiments effectiveness of effector cell killing of target cells is determined by comparing impedance-based curves over time. Typically, a decreasing impedance or impedance based parameter is indicative of increased effectiveness. In a related embodiment, effectiveness of effector cell killing of target cells is determined by calculating and comparing percent cytolysis of the target cells.

In some embodiments the assay also includes monitoring the impedance of a control well, whether positive or negative. For example, the method can include adding the target cells to a second well of the device designated a control well, adding a negative control compound to the control well that does not join effector cells to target cells, monitoring impedance of the control well and optionally deriving an impedance-based parameter from the impedance of the control well; and comparing the impedances or impedance based parameters over time between the control well and test well to determine whether adding the bispecific engager increases effector cell killing of target cells.

In some embodiments, a check point inhibitor is added to the well to increased effectiveness of cancer cell killing. Check point inhibitors seek to overcome one of cancer's main defenses against an immune system attack by blocking normal proteins on cancer cells. Examples of check point inhibitors include antibodies or antibody fragments targeting PD1, CTLA-4, CD137, OX40, CD27, CD40L, TIM3 on the surface of effector cells or their respective cognate ligand on the surface of target cells.

Furthermore, among the benefits of the invention include the ability to effectively test adoptive cell transfer therapeutic approaches on a patient's cancer cells. Adoptive cell transfer (ACT) is an approach usually involving the engineering of a patient's own immune cells to recognize and attack tumors and other cancer cells. Although still in clinical trials many patient's cancers have disappeared entirely and several have remained cancer free for extended periods.

The most commonly known ACT approach involves chimeric antigen receptor (CAR) T cells. CAR-T cells are T cells genetically engineered to produce special receptors on their surface (chimeric antigen receptors), which allow T-cells to recognize specific antigens on tumor cells. These engineered cells are then grown in the laboratory and infused into the patient. The T-cells then multiply in the patient's body and target the cancer cells displaying the specific antigens.

Accordingly, the invention provides a method of determining the effectiveness of proposed adoptive cell transfer (ACT) therapies on cancer cells by monitoring cell-substrate impedance of a cancer cell population in response to the addition of engineered immune cells, such as CAR-T cells; and comparing the measured impedance or impedance based parameter (e.g. cell index, normalized cell index, cell change index, cell number calculated by cell index) over time to assess the effectiveness of cancer cell killing. An exemplary method includes providing a cell-substrate impedance monitoring device operably connected to an impedance analyzer, wherein the device comprises a well for receiving cells and an electrode array at a base of the well; adding one or more target cells characterized as cancer cells to the well; adding effector cells to the well to form a test well, wherein the effector cells are immune cells, further wherein the effector cells are engineered to display a binding moiety suspected of binding the target cells, such as engineered CAR-T cells; monitoring cell-substrate impedance of the test well before and after adding the effector cells and optionally deriving impedance-based parameters from the impedances; and determining effectiveness of effector cell killing of target cells by comparing the impedances or impedance based parameters over time.

The method can be used with the target cells embodied as circulating tumor cells (CTCs) collected from blood or tumor cells, optionally collected from a tissue biopsy. Furthermore, cancer cells can be used from a variety of biological samples such as a solid tumor, a haematopoietic tumor, blood, and pleural effusion.

Although described primary in regards to CAR-T cells, the method can also apply to effector cells such as natural killer cells (NK cells), macrophages, neutrophils, eosinophils, T-cells, and B-cells.

Thus, in some embodiments the effector cells added to the target cells are CAR-T cells, which are preferably engineered from T-cells collected from the patient from which the target cells were also collected. Methods for collecting effector cells, such as T-cells are well known in the art and typically including purification from a blood sample using one or more approaches such as density centrifugation, surface marker detection or binding, flow cytometric sorting and others. Genetically engineering cells, such as CAR-T cells may be performed using protocols known in the immunology arts. In still further embodiments, the CAR displays a single-chain fragment variable (scFv) region for binding to the cancer cell. In other embodiments, a single CAR displays multiple scFv regions which bind different moieties (against a same or different protein) on the surface of target cells. In further embodiments the scFv is obtained using phage display technology known in the immunology arts. Relatedly, in some embodiments the method also includes a step of engineering the effector cells to express an exogenous protein to form part of the CAR.

In some embodiments, the effector cells are engineered to display multiple distinct CARs targeting multiple proteins on the surface of target cells.

In further embodiments the effector cells are further engineered to increase expression of an exogenous compound, optionally Interleukin 2, to promote growth, proliferation or persistence of the effector cells.

The methods may be used to assay for complement-mediated cellular cytotoxicity in the presence of neutrophils or anti-MHC antibody. The complement system is one of the major effector mechanisms of the humoral and innate immunity. Complement proteins bind to tumor cells that have been targeted by IgG and IgM antibodies through interaction with the constant domain of the antibodies. The interaction of complement proteins with the antibody on the surface of tumor cells will lead to the destruction of the tumor cells by the formation of pores on the membrane of target cells by components of the complement pathway or by recruitment of neutrophils which either engulf tumor cells or induce its destruction by granzymes. Neutrophils contain specific receptors which recognize components of the complement system.

Thus a method of assaying for complement-mediated cellular cytotoxicity is also provided, which includes providing a cell-substrate impedance monitoring device operably connected to an impedance analyzer, wherein the device comprises a well for receiving cells and an electrode array at a base of the well; adding target cells characterized as cancer cells to the well; adding complement and a proposed therapeutic antibody capable of interacting with the target cells to the well; monitoring impedance of the well before and after adding complement and optionally deriving impedance based parameters from the impedances; and determining effectiveness of effector cell killing of the target cells by comparing the impedances or impedance based parameters over time.

Oncolytic viruses are another recent class of therapeutic agents that promote anti-tumor responses. As the infected cancer cells are destroyed by oncolysis they release new infections virus particle or virons to help destroy the remaining tumor. Oncolytic viruses are though not only to cause direct destruction of the tumor cells, but also to stimulate host anti-tumor immune responses. To this end, a method of assessing cytolytic activity on cancer cells is provided, which includes providing a cell-substrate impedance monitoring device operably connected to an impedance analyzer, wherein the device comprises a well for receiving cells and an electrode array at a base of the well; adding one or more target cells characterized as cancer cells to the well; adding an oncolytic virus to the well to form a test well, wherein the virus is suspected of recognizing and lysing cancer cells; monitoring cell-substrate impedance of the test well before and after adding the oncolytic virus and optionally deriving impedance-based parameters from the impedances; and determining effectiveness of target cell lysis by comparing the impedances or impedance based parameters derived from the impedances over time.

The cancer cells can be obtained from any suitable biological sample such as a solid tumor, a haematopoietic tumor, blood, and pleural effusion. In some embodiments target cells are circulating tumor cells collected from blood. In other embodiments, the target cells are tumor cells collected from a tissue biopsy. In still other embodiments the target cells are of a tumor cell line.

The oncolytic virus itself does not significantly interact with the electrode and thus the impedance corresponds the status of the target cells. To this end, the impedance based parameter can be a cell index or a normalized cell index that is normalized to a time point before adding the virus. Impedances or impedance based parameters decreasing over time are indicative of increased oncolytic activity. Relatedly the impedance based parameter can an impedance based curve. In other embodiments effectiveness of target cell lysis is determined by calculating and comparing percent cytolysis of the target cells.

E. Pharmaceutical Formulations & Medicaments

Once the proposed therapeutic is determined effective at killing cancer cells using the cell-substrate impedance monitoring technology, it can be formulated as a medicament or a pharmaceutical formulation ultimately for treating a cancer patient and most preferably the cancer patient from which the target cells were collected. One of ordinary skill in the art to which the invention belongs will recognize that the formulation can depend on the form of the therapeutic and its route of administration as known in the pharmaceutical arts.

In embodiments where the proposed therapeutic is an effector cell, such as a CAR-T cell, the effector cell may be expanded to a larger effector cell population under sterile conditions, suspended in a saline solution and infused into the bloodstream or surgically applied against a tumor for treatment.

In embodiments where the proposed therapeutic is a compound, such as a bispecific engager, the compound can be combined with pharmaceutically acceptable excipients, carriers, diluents, sweeteners, disintegrants, binders, lubricants, glidants, colorants, flavors and mixtures thereof then administered orally, applied locally or provided through other routes consistent with the pharmaceutical arts for cancer treatment.

Diluents may include, but are not limited to, mannitol, sorbitol, xylitol, microcrystalline cellulose, silicified microcrystalline cellulose, hydroxypropyl methylcellulose, hydroxypropyl cellulose, and pullulan.

Glidants may include, but are not limited to, silicon dioxide, colloidal silicon dioxide, calcium silicate, magnesium silicate, magnesium trisilicate, talc, starch, and mixtures thereof.

Binders may include, but are not limited to, sodium alginate, cellulose, methylcellulose, ethyl-cellulose, hydroxypropyl cellulose, hydroxypropyl methylcellulose, sodium carboxymethyl cellulose, polypropylpyrrolidone, polyvinylprrolidone, gelatin, polyethylene glycol, starch, pre-gelatinized starch, sugars, trehalose, glucose, tragacanth sorbitol, acacia, alginates, carrageenan, xanthan gum, locust bean gum and gum arabic, waxes, poly acrylamide, and mixtures thereof.

Lubricants may include, but are not limited to, calcium stearate, glyceryl monostearate, glyceryl behenate, glyceryl palmitostearate, hydrogenated vegetable oil, light mineral oil, magnesium stearate, mineral oil, polyethylene glycol, poloxamer, sodium benzoate, sodium lauryl sulfate, sodium stearyl fumarate, stearic acid, talc, zinc stearate, and mixtures thereof.

Disintegrants may include, but are not limited to, sodium starch glycolate, sodium carboxymethyl cellulose, calcium carboxymethyl cellulose, croscarmellose sodium, crospovidone, alginic acid, chitosan, methyl cellulose, microcrystalline cellulose, powdered cellulose, lower alkyl substituted hydroxypropyl cellulose, polacrilin potassium, starch, pregelatinized starch, sodium alginate, and mixtures thereof.

EXAMPLES

Example 1

Profiling of Cancer Cell Responses to Anti-Cancer Drugs Using Cell-Substrate Impedance Monitoring In this study, we used cell-substrate impedance monitoring (RT-CES system, ACEA Biosciences, Inc, San Diego, CA) to dynamically monitor cancer cell responses to chemotherapeutic compounds with characterized mechanisms, and to profile the specific cell response patterns. Thirteen cancer cell lines including cancers of breast, prostate, lung, colon, ovary, kidney, fibroblast, and central nervous system were tested (TABLE 1). Each cancer cell type was treated with 11 chemotherapeutic compounds, classified as DNA damaging agents, protein kinase inhibitors, anti-mitotic drugs, cell cycle specific inhibitors, protein synthesis inhibitors plus a compound of unknown category (TABLE 2). Dynamic and dose dependent cell-compound interaction patterns were characterized and summarized for all the tested cell lines and compounds. The profiles for three drugs, doxorubicin, olomoucine and paclitaxel against a panel of 12 different cell lines are presented in FIGS. 9A-11B, respectively. In addition, we characterized the biological effect of these compounds on cells by monitoring cell cycle progression, cell viability and morphological status of the cells in an attempt to correlate specific cellular response to the shape of the cell index trace (FIGS. 12A-14B). Furthermore we calculated the time-dependent IC-50 values for each compound against the various cell lines (FIGS. 15A-D) and developed an algorithm to calculate Cell Change Index to profile the dynamic cell response of the different chemotherapeutic agents across the different cell lines.

Figure 16A:
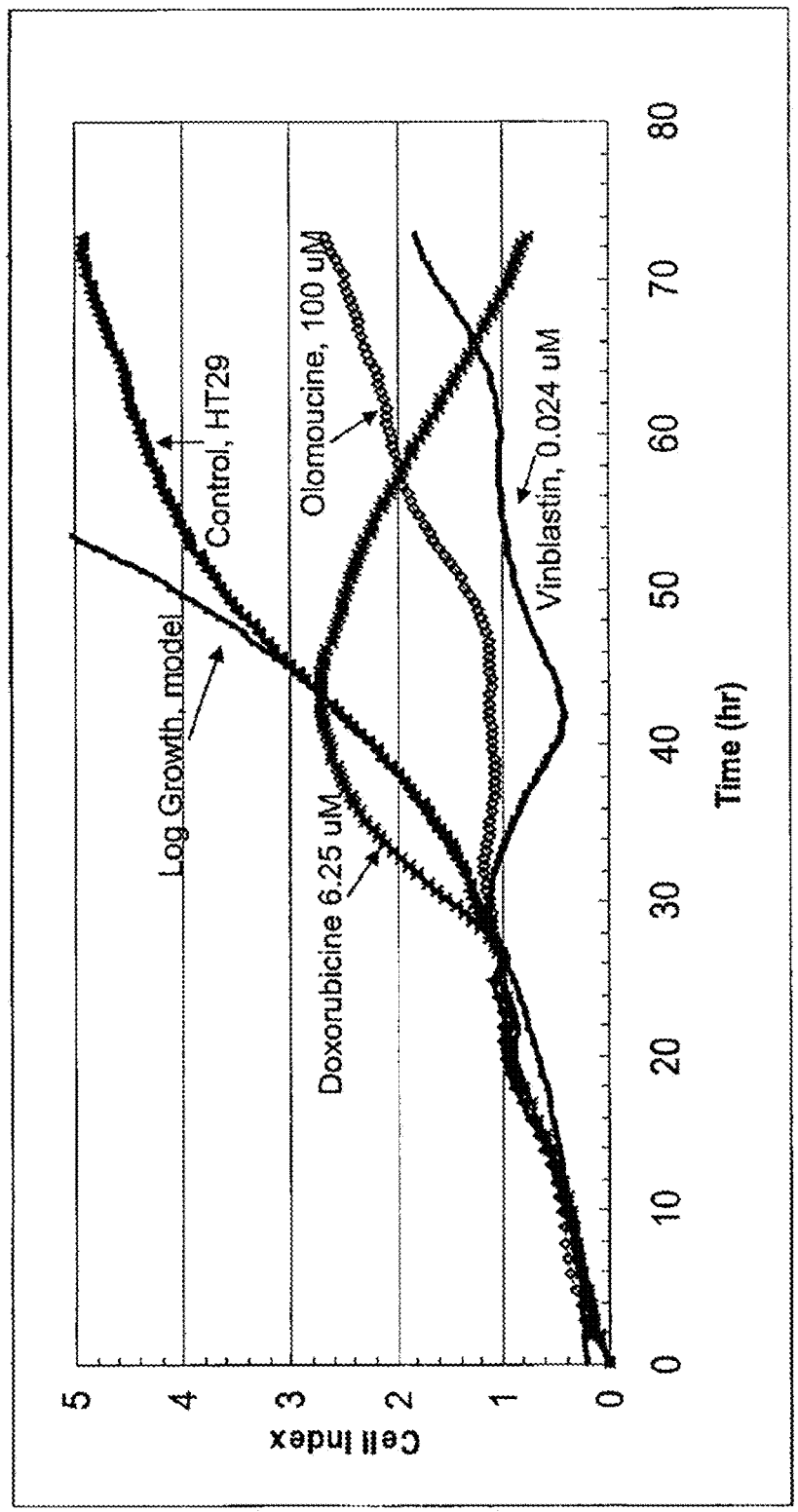
FIG. 16A shows the cell index curves of human colorectal adenocarcinoma cells (HT29 cells) before and after treatment with doxorubicine, vinblastine, or olomoucine. Also shown is a theoretical exponential increase of cell index with time (labeled as "Log-growth, model") and cells treated with DMSO vehicle control (labeled as "Control, HT29").
Figure 16B:
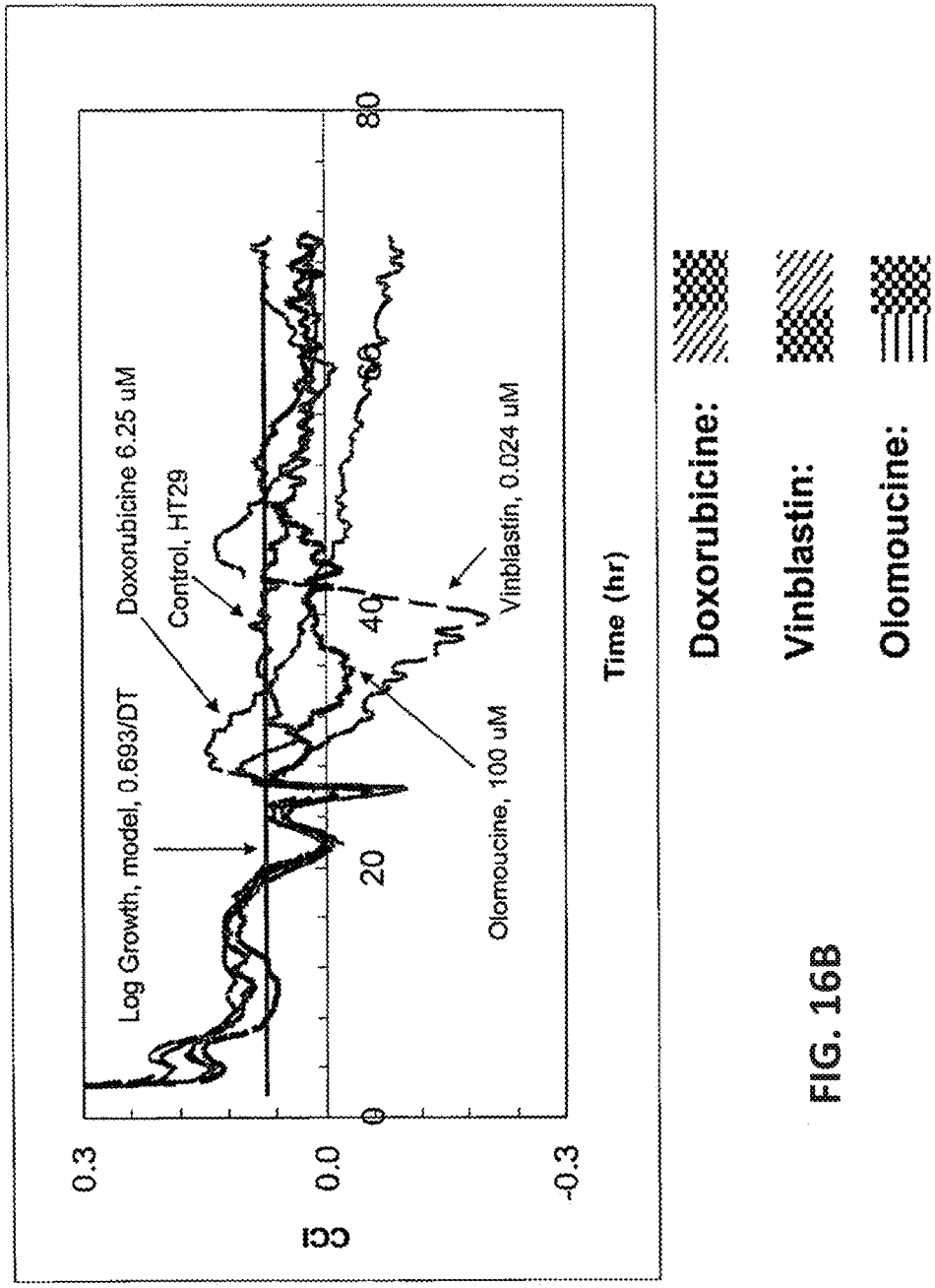
FIG. 16B shows the derived cell change index (CCI) from the cell index curves shown in FIG. 16A. Also shown is the "black-white shading codes" used for different responses based on the convention shown in FIG. 16C.
Figure 16C:
FIG. 16C shows the color-coding scheme used for representing the CCI curves. If the DT is the doubling time for the cells undergoing exponential growth in the cell culture media used, then CCI having different values relative to 0.7/DT indicates the different cell change status. If CCI>>0.7/DT, cell index increases faster than that expected for an exponential growth (or log growth) of the cells (such region n the CCI curve is represented as ▓ Rectangle). If CCI is about 0.7/DT, cell index increases in the same rate as that expected for an exponential growth of the cells (such region in the CCI curve is represented as ▓ Rectangle). If CCI is more than zero but somewhat smaller than 0.7/DT, then cell index increases in the rate slowed than that expected for an exponential growth (such region of the CCI curve is represented as ▓ Rectangle). If CCI is about zero, then cell index shows a near constant value (such region of the CCI curve is represented as ▓ Rectangle). If CCI is negative, then the cell index is decreasing with time, showing the cells losing attachment to the electrode surface or changing their morphology (such region of the curve is shown as ▓ Rectangle). If CCI is very negative, then the cell index decreases rapidly with time, showing that either cells lose attachment to the electrode surfaces quickly or cells change their morphology very quickly (such region of the CCI curve is represented as ▓ Rectangle). The transient, quick noise in the CCI values are removed so that the whole CCI curve is represented after compound addition by one, two or three black/white-shaded rectangles.
Figure 16C:
Figure 16C:
Figure 16C:
Figure 16C:
Figure 16C:
Figure 17:
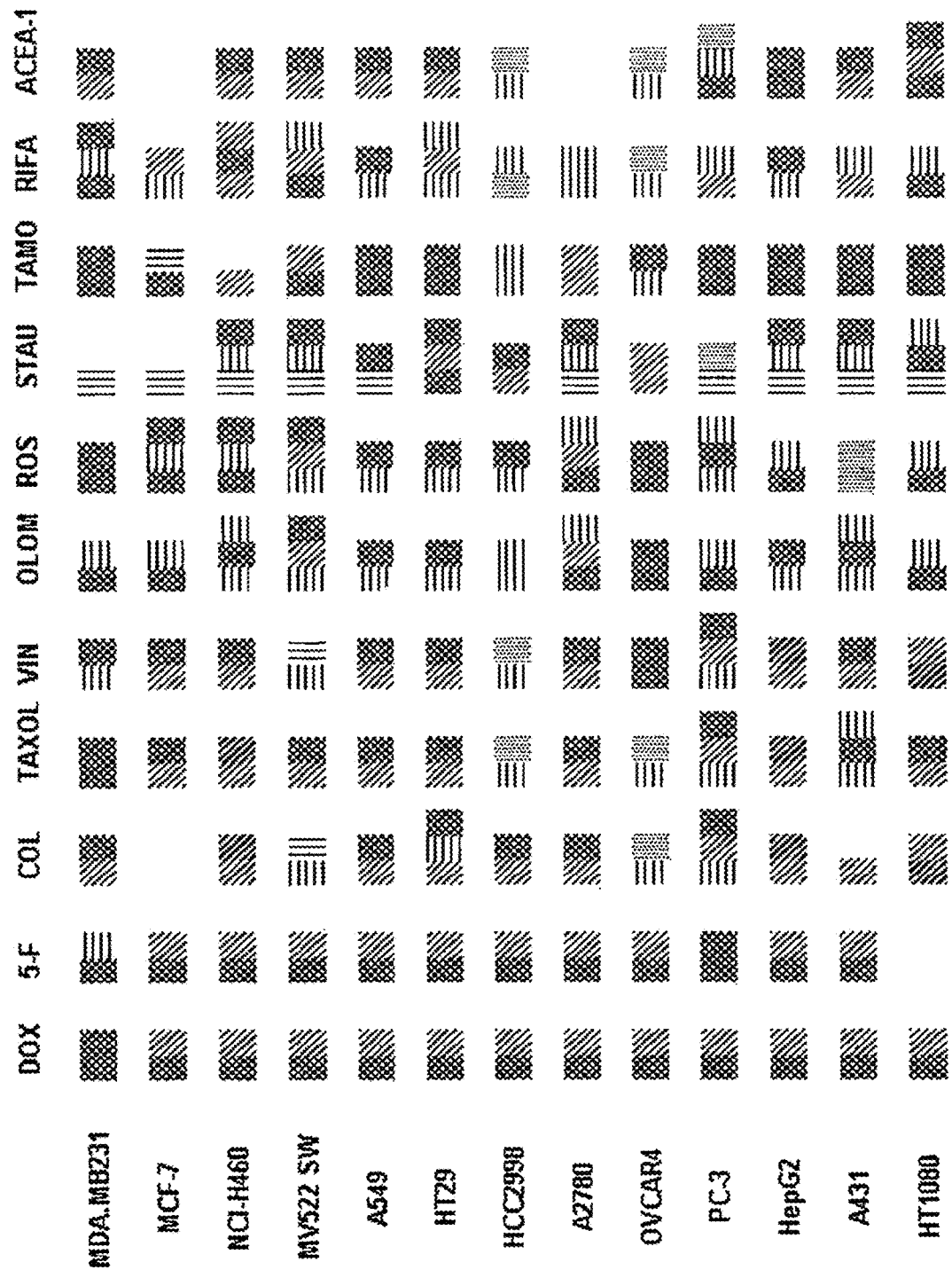
FIG. 17 shows the cell response profile of each cell line tested against the indicated chemotherapeutic agents. For each cell line and compound, the time-dependent cell change index (CCI) was calculated from their corresponding RT-CES responses at an IC50 concentration. (IC 50 is time dependent so that the IC50 concentration at 30 h, or the concentration closest to that, after drug addition is used). The specific CCI curves as related to specific cellular responses were coded according to the convention described in FIG. 16C and displayed in groups of compounds with similar mechanism of action. DOX: doxorubicin; 5-F: 5-Fluorouracil; COL: Colcemid; TAXOL: paclitaxel; VIN: vinblastin; OLOM: Olomoucine; ROS: Roscovitine; STAU: Staurosporine; TAMO: Tamoxifan; RIFA: Rifampicin; ACEA-1: an ACEA test compound.

Cell Change Index was calculated for the dynamic RT-CES responses of the different cell lines to different chemotherapeutic agents using the definitions described above. Based on the time-dependent values of CCI, each CCI value region across the time scale is represented by black-white shading-based coding. For example, if after compound addition, the CCI value (for a particular cell line under a specific compound treatment at the concentration of IC50 value) is nearly zero for certain period of time and then becomes positive, attaining a value about 0.7/DT (DT is doubling). Then the cell response to this compound is represented as a  rectangle followed by a  rectangle. Examples of such analysis is shown in FIG. 16A-C. The overall black-white shading-based coding map representing the cell dynamic responses to various compounds is shown in FIG. 17.

In summary of this study, we note that using the RT-CES system to screen chemotherapeutic agents results in unique activity patterns that is dependent on the compound itself, the concentration, length of incubation and the cell type. The "signature" patterns of each drug correlates with specific biological phenomenon such as log growth, cell cycle rest, morphology change and cell death. Cell Change Index was a good parameter derived from RT-CES data to mathematically describe cell changes. Cell response profiling based on CCI value indicates that drugs with similar mechanism of action displays similar patterns. Thus, the similarity in the dynamic cell-compound interaction patterns may indicate similarity in mechanism of action, mode of resistance and possibly molecular targets. The RT-CES system can be readily adapted to high throughput dynamic screening and analysis of anti-cancer compounds and the information-intensive approach presented in this study can be applied to profile existing cancer chemotherapeutic agents, screen new compounds and provide insight into the mechanism of action of anti-cancer agents.

TABLE 1

List of cancer cell lines tested against a number of chemical compounds.

| Cancer Cell Line | Organ or Tissue Origin |
| --- | --- |
| MDA.MB231 | Breast Cancer |
| MCF7 | Breast Cancer |
| NCI-H460 | Non-Small Cell Lung Cancer |
| MV522 SW | Non-Small Cell Lung Cancer |
| A549 | Non-Small Cell Lung Cancer |
| HT29 | Colon Cancer |
| HCC2998 | Colon Cancer |
| A2780 | Ovarian Cancer |
| OVCAR4 | Ovarian Cancer |
| PC-3 | Prostate Cancer |
| HebG2 | Human Hepatosarcoma |
| A431 | Epidermoid Cancer |
| HT1080 | Fibrosarcoma |

TABLE 2

List of chemical compounds used in the study of profiling cell dynamic responses to a number of anti-cancer compounds.

| Mechanism of Action | Chemical Compound | Concentration (dilution factor of 2) |
| --- | --- | --- |
| Effect DNA replication or Topology | Doxorubincin | 6.25 µM-0.098 µM |
| Effect DNA replication or Topology | 5-Fluorouracil | 50 µM o 0.78 µM |
| Mitotic Poison | Colcemid | 3.12 µM-0.049 µM |
| Mitotic Poison | Paciltaxel | 0.0125 µM-0.00019 µM |
| Mitotic Poison | Vinblastin | 1.56 µM-0.024 µM |
| Cell Cycle Arrest | Olomoucine | 100 µM-1.56 µM |
| Cell Cycle Arrest | Roscovitine | 50 µM-0.78 µM |
| Kinase Inhibitor | Staurosporine | 5 µM-0.078 µM |
| Kinase Inhibitor | Tamoxifan | 50 µM-0.78 µM |
| Protein Synthesis Inhibitor | Rifampicin | 100 µM-1.56 µM |
| Unknown | ACEA-1 | |

Example 2

Cytotoxicity Profiling

Methods

Cells. All the cells used in this study were obtained from ATCC and maintained at 37° C. incubator with 5% $CO_2$ saturation. H460, HepG2 and HT1080 cells were maintained in RPMI media containing 5% FBS and 1% penicillin and streptomycin. NIH3T3 cells were maintained in DMEM media containing 10% FBS and 1% penicillin and streptomycin.

Cell Proliferation Assays. For each of the cell type, the indicated number of cells was seeded per well in 96× microtiter plates (E-plate™) with incorporated electrode structures in individual wells device in 100 μL of media. The attachment, spreading and proliferation of the cells were continuously monitored every 30 minutes using the RT-CES system (a cell-substrate impedance monitoring system). Cell proliferation was monitored for a period of 48-72 hours depending on the experiment. The electronic readout, cell-sensor impedance is displayed as a parameter called Cell Index.

Figure 18:
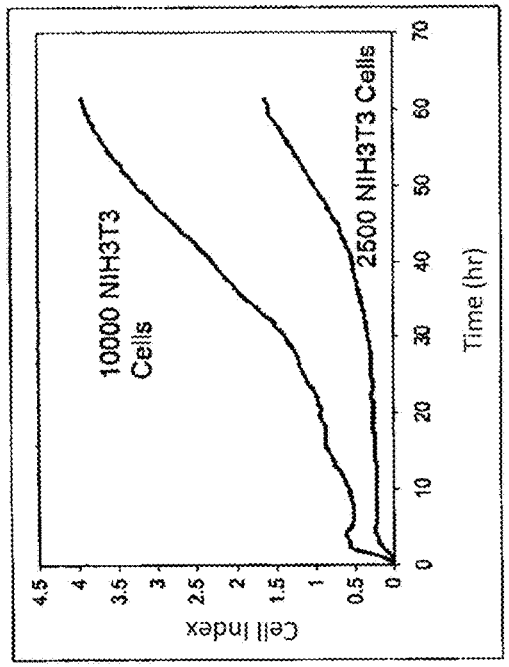
FIG. 18 shows the monitoring of cell proliferation over time of fibrosarcoma cells (H1080 cells), lung cancer cells (H460 cells), hepatosarcoma cancer cells (HepG2) and mouse fibroblast cell lines NIH3T3 after seeding at a density of 2500 and 10,000 cells per well of ACEA 96× e-Plate device. The adhesion, spreading and proliferation of the cells were dynamically monitored every 30 minutes using the cell-substrate impedance monitoring system.
Figure 18:
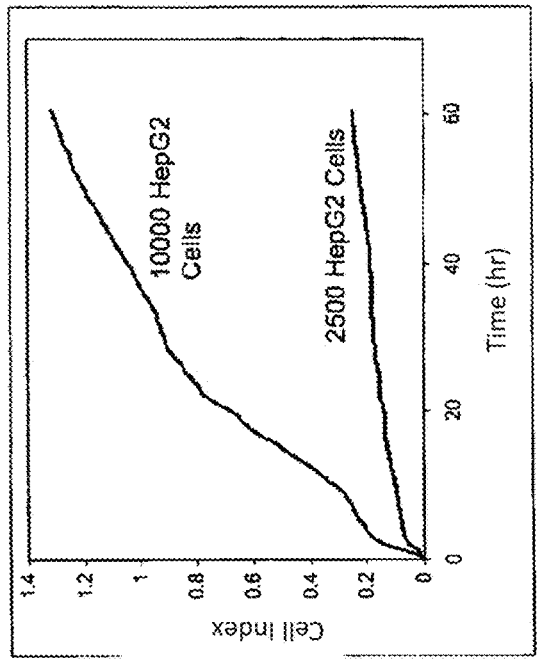
Figure 18:
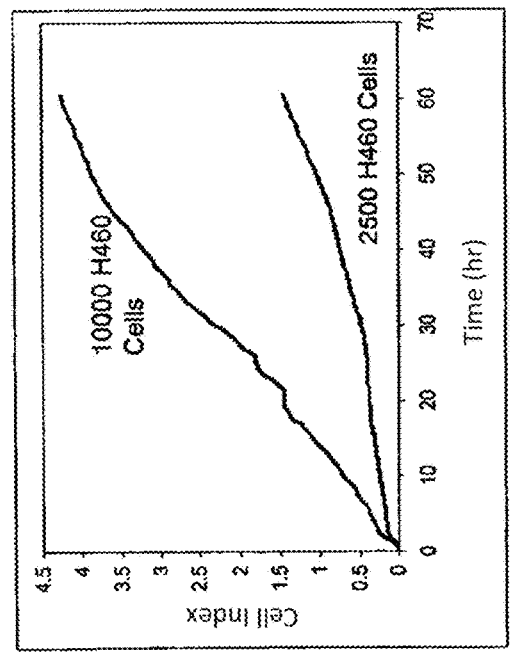
Figure 18:
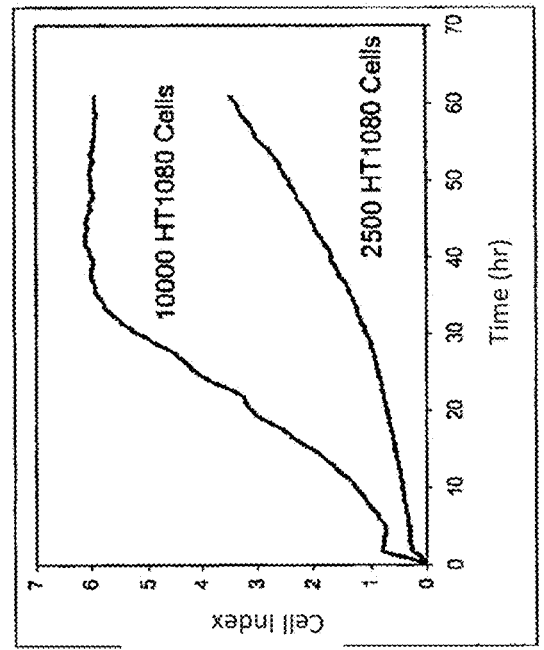

Drug Treatment and Cytotoxicity Assessment. For each cell type the optimum cell concentration was chosen based on their respective proliferation pattern (FIG. 18). The indicated cell numbers were seeded per well of ACEA's 16× or 96× E-Plate (device for monitoring cell-substrate impedance) in 100 μL final volume. The attachment, spreading and proliferation of the cells were continuously monitored every 30 minutes using the RT-CES system (cell-substrate impedance monitoring system). Approximately 24 hours after seeding, when the cells were in the log growth phase, the cells were treated with 100 μL of the indicated compounds dissolved in cell culture media. The cells were also treated with DMSO, which served as vehicle control. Depending on the experiment, the final DMSO concentration in the media was in the range of 0.25%-0.5%.

MTT Assay. Increasing numbers of NIH3T3 cells were seeded in 16× e-plate and monitored by RT-CES to obtain the corresponding Cell Index. The media was immediately aspirated and the cells were then assayed by using the standard MTT assay according to the manufacturer's protocol.

Flow Cytometry. A549 cells were seeded at a density of 500,000 cells/well in 60 mm tissue culture dishes. Approximately, 24 hours after seeding, the cells were treated with the indicated final concentration of Olomoucine and 16 hours later the cells were washed with PBS, trypsinized, washed twice with PBS and fixed in 70% methanol and stored at 4° C. until the staining step. The cells were stained with propidium iodide and analyzed by FACS using a wavelength of 488 nm.

Example 3

Monitoring Cancer Cell Proliferation in Real-Time Using the RT-CES

In order to assess dynamic cell proliferation cell-substrate impedance monitoring with the RT-CES System, H460 human lung cancer cells, H1080 fibrosarcoma cells, HepG2 human hepatosarcoma cells and NIH3T3 mouse fibroblasts were seeded at 2500 and 10,000 cells per well in triplicate in ACEA's 96× E-plate™. The cells were continuously monitored every 30 minutes using the RT-CES system for the indicated period of time (FIG. 18). As shown in FIG. 18, each cell type has its own characteristic kinetic trace, based on the number of cells seeded, the overall size and morphology of the cells and the degree to which the cells interact with the sensor surface. Also, the adhesion and spreading kinetics as well as time when the cells enter the log growth phase is characteristic of each of the indicated cell lines and therefore offers an excellent internal control and a way to standardize and validate stock cultures during different phases of the manufacturing process.

Figure 19A:
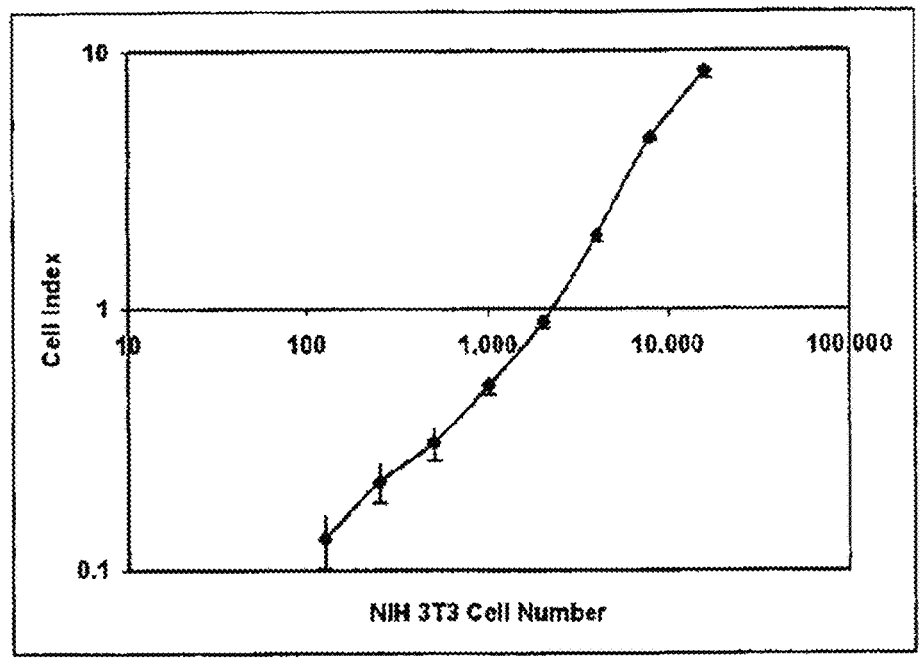
FIGS. 19A-B shows a series of graphs correlating cell-substrate impedance (Cell Index) and number of cells seeded for comparing Cell Index with MTT.
Figure 19B:
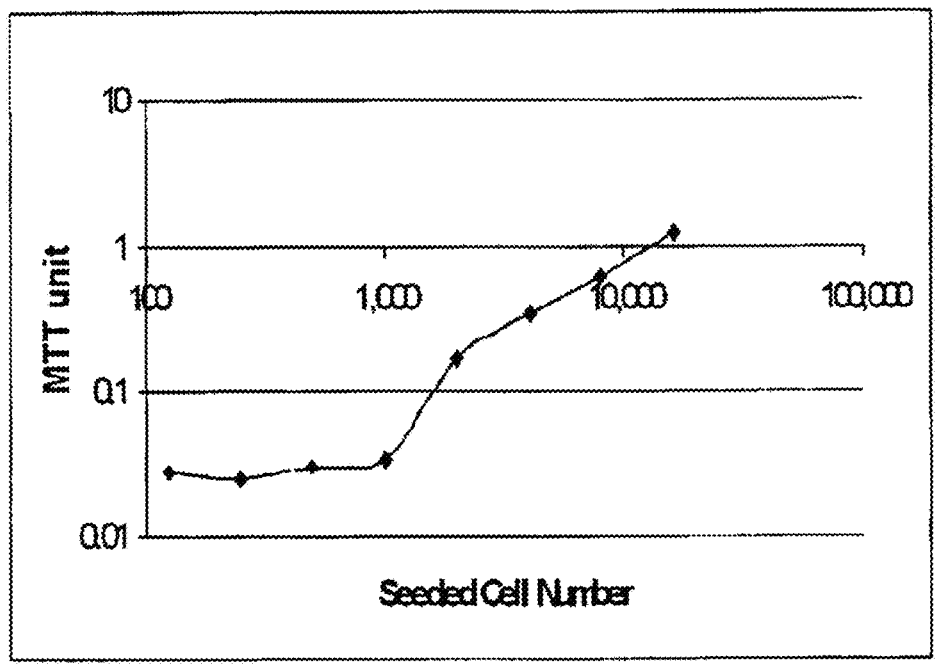

To ascertain that the RT-CES units of Cell Index correlates with the number of the cells in the well, increasing numbers of NIH3T3 cells were seeded in ACEA 16× E-plate™ and were monitored for up to 10 hours, at which time the Cell Index was acquired. FIG. 19A shows a plot of Cell number seeded versus the Cell Index obtained and indicates that for this particular cell type the RT-CES system could detect as little as 100 cells and the readout is linear by two orders of magnitude all the way up to 10000 cells. In addition, at the end of the experiment described in FIG. 19A, the cells were also assayed by the MTT assay. As shown in FIG. 19B, even at up to 1000 cells the MTT assay is not appreciably different than background values and for cell numbers exceeding 1000, then the MTT units correlates with the number of cells seeded in a linear fashion. However, it is important to remember that while the RT-CES system is capable of dynamic and continuous measurements, for comparative reasons the experiment described in FIG. 19 was only conducted at a single point, since MTT is a single point assay.

Example 4

Determining Potential Therapeutic Treatments Against Cancer Cells Using the RT-CES Cell-Substrate Impedance Monitoring System To assess drug potency using the RT-CES cell-substrate impedance monitoring system, the IC-50 value of Tamoxifen was determined for different cell lines and compared with MTT assay at 48 hours after Tamoxifen addition. According to TABLE 3, the IC-50 values obtained for Tamoxifen for the different cell lines using the RT-CES system is very consistent with the values obtained by the MTT assay, indicating that the RT-CES system can be used to assess the potency of various drugs against different adherent cell lines.

Figure 20A:
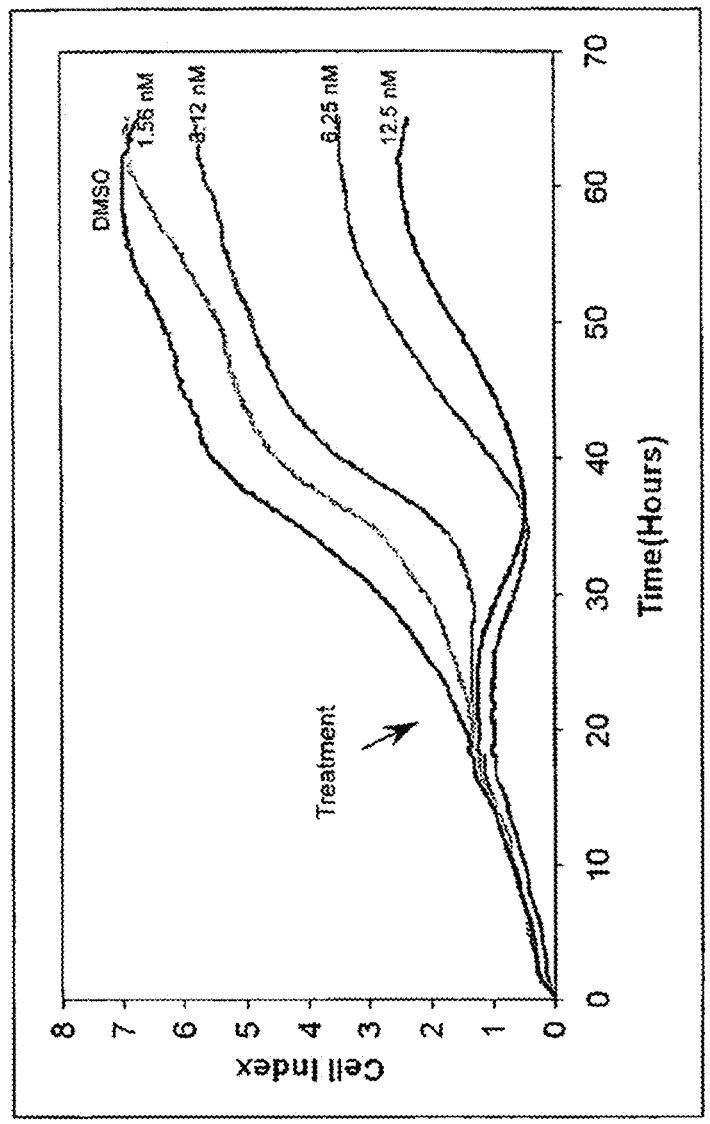
FIGS. 20A-B depict dynamic monitoring of drug interaction with target cells using a cell-substrate impedance monitoring system.
Figure 20B:
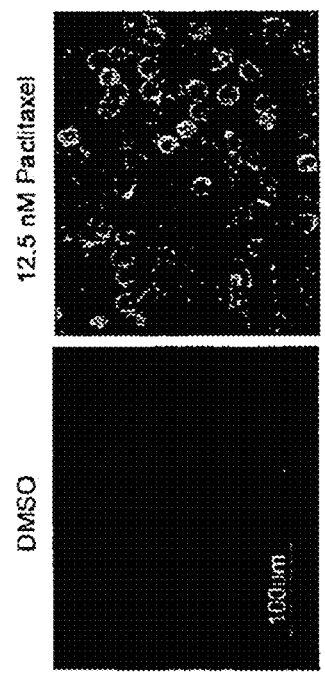

In order to observe the kinetics of drug interaction with target cells, A549 non-small lung cancer cells were seeded in ACEA 96× E-plate™ and continuously monitored until the cells reached the log growth phase at which point different concentrations of paclitaxel were added to the cells at the indicated final concentration. As shown in FIG. 20A, paclitaxel at the highest concentration initially induces a cytotoxic effect which is mainly due to cell death as judged by Annexin V staining (FIG. 20B). Remarkably, the cells recover from the initial cytotoxic effect of the drug and start to re-proliferate. While it remains to be determined if this phenomenon is due to metabolism and inactivation of paclitaxel or due to the emergence of paclitaxel-resistant subpopulation, this experiment clearly exemplifies the tremendous advantage of real-time measurement which is offered by the RT-CES system and allows the user to the opportunity to observe and assess the entire history of drug interaction with the target cells which provides further information in addition to cell viability or cytotoxicity. The phenomenon observed in FIG. 20A would've been easily missed by traditional single-point assays such as MTT.

Figure 21A:
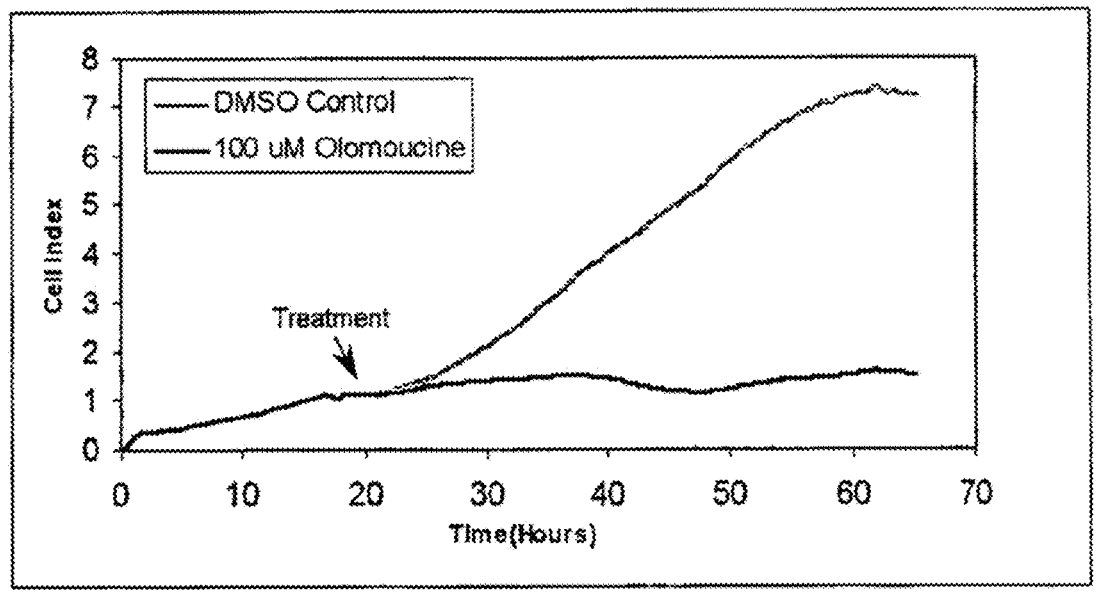
FIGS. 21A-B depict dynamic monitoring of cell cycle arrest using a cell-substrate impedance monitoring system. Human alveolar basal epithelial cells (A549 cells) were seeded in a cell-substrate monitoring device at 10,000 cells per well and continuously monitored using the RT-CES. The cells were treated with either (FIG. 21A) DMSO or 100 µM Olomoucine.
Figure 21B:
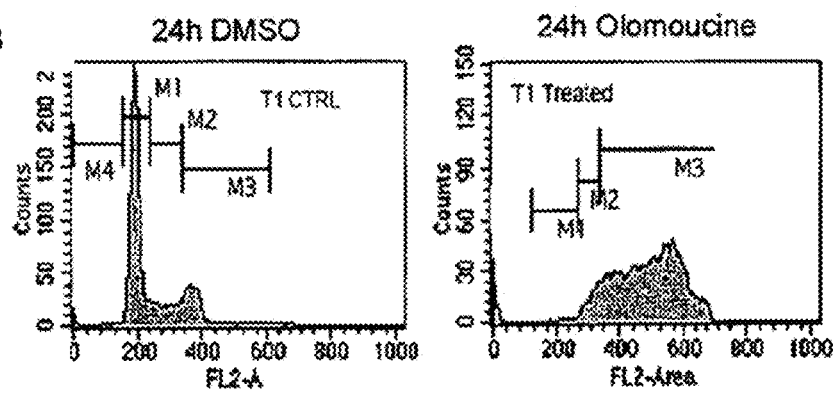

Yet another major advantage of using the RT-CES system to continually monitor the interaction of drugs with target cells is that the user can obtain insight into the mechanism of action of the drug of interest. To demonstrate this point, A549 cells were seeded in ACEA 96× microtiter device and continually monitored by the RT-CES. The cells were treated with either DMSO as the vehicle control or with 100 µM Olomoucine which is a CDK inhibitor and induces cell cycle arrest either at G1→S transition or at the G2→M transition, depending on the cell line. As shown in FIG. 21A addition of Olomoucine to exponentially growing A549 cells causes the trace of the Cell Index recordings of the cells to level off and remain in a steady state that is reminiscent of cell cycle block, where the cells are neither proliferating nor dying off. The control cells treated with DMSO continue to proliferate until they reach confluence, at which time they are contact inhibited and the Cell Index recording levels off. To demonstrate that the effect of Olomoucine on A549 cells as monitored by the RT-CES was indeed due to an arrest of the cell cycle, A549 cells growing on tissue culture dish were treated with the same concentrations of DMSO and Olomoucine and subjected to flow cytometry analysis. As shown in FIG. 21B, the flow cytometry analysis indicates that treatment of A549 cells with the indicated concentration of Olomoucine induces cell cycle arrest at the G2→M transition, where CDKs such as CDK2 is active. Taken together, using the RT-CES system to dynamically monitor drug interaction with the target cells offers the user the opportunity to understand the mechanism of drug action and its mode of interaction with the target cell.

Figure 22A:
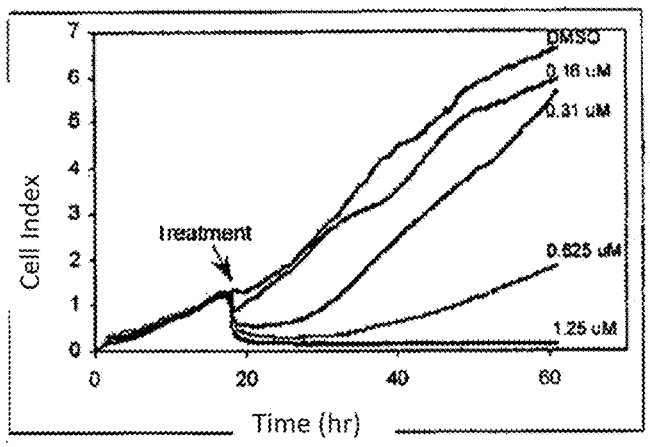
FIGS. 22A-C depicts dynamic monitoring of cytotoxic compounds with target cells using a cell-substrate impedance monitoring system. Human alveolar basal epithelial cells (A549 cells) were seeded in a cell-substrate monitoring device and continuously monitored using the RT-CES system. The cells were treated with the indicated final concentrations of (FIG. 22A) staurosporine, (FIG. 22B) vinblastine and (FIG. 22C) 5-fluorouracil.
Figure 22B:
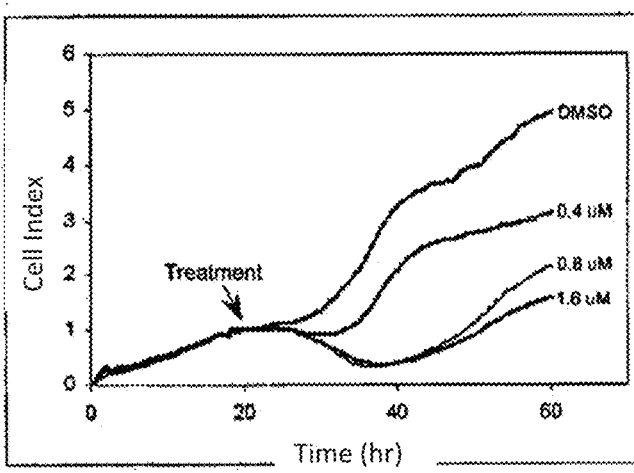
Figure 22C:
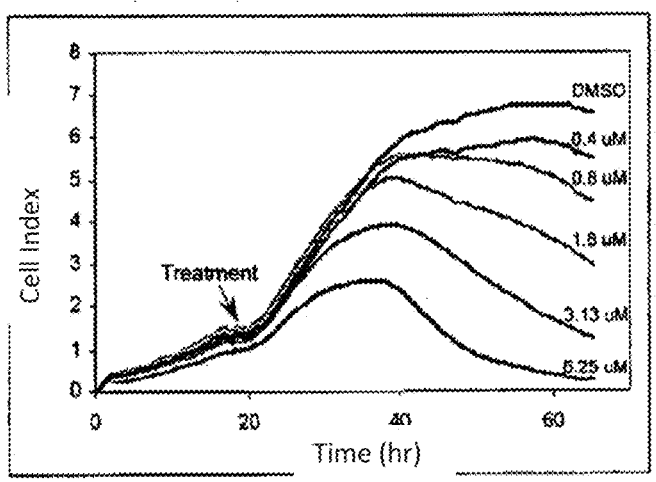

In order to assess the RT-CES system for analysis of cytotoxicity, the interaction of A549 cells was examined with cytotoxic agents with different mechanism of action. FIG. 22A-C shows the characteristic trace of A549 cells monitored by RT-CES™ and treated with different concentrations of 5-fluorouracil, vinblastine and staurosporine. According to FIG. 22A-C, dynamic monitoring of the interaction of the indicated cytotoxic agents leads to the generation of characteristic kinetic patterns that is dependent on the cellular background, the concentration of the drug, the duration of exposure and the mechanism of drug action. Since each compound has its own characteristic pattern, these kinetic traces could potentially be used to determine the mechanism of action of compounds with unknown targets by comparing the kinetic profile to the profile of compounds with known mechanism of action.

Label-free and dynamic monitoring of cell proliferation, viability and cytotoxicity using the RT-CES system offers very distinct and important advantages over traditional end-point assays. It allows for built in internal quality control to assure consistency and reproducibility between the different assays. Dynamic monitoring allows for observation of the entire episode of drug interaction with target cells and the user can therefore have a better understanding of the mode and mechanism of drug interaction. Furthermore, the actual kinetic trace of the drug interaction with the target cell is very significant because it can offer clues as to the mechanism of drug interaction with the target cell. Finally, since each compound or drug has its own characteristic profile with respect to its interaction with target cells, the RT-CES system can be used as a way to determine the mechanism of action of drugs with unknown targets.

TABLE 3. Comparison of IC-50 values for Tamoxifen treatment of different cancer cell lines using the RT-CES system versus MTT assay. The indicated cell lines were seeded in ACEA 16× devices and monitored by RT-CES. Approximately 24 hours later, the cells were treated with increasing concentrations of Tamoxifen and then continually monitored by RT-CES. The experiment was stopped about 48 hours later and the cells in the 16× devices (16× E-Plates) were assayed by using MTT. The IC-50 values derived from RT-CES system are time-dependent. In the table, the IC-50 values at about 48 hrs after compound treatment are shown for RT-CES system determination and MTT assay.

TABLE 3

| Cell type | RE-CES | MTT Assay |
| --- | --- | --- |
| HT1080 | 22.4 µM | 30.0 µM |
| NIH3T3 | 16.0 µM | 19.0 µM |
| HepG2 | 15.2 µM | 16.2 µM |
| HUEVEC | 7.5 µM | 8.0 µM |

Example 5

Figure 23:
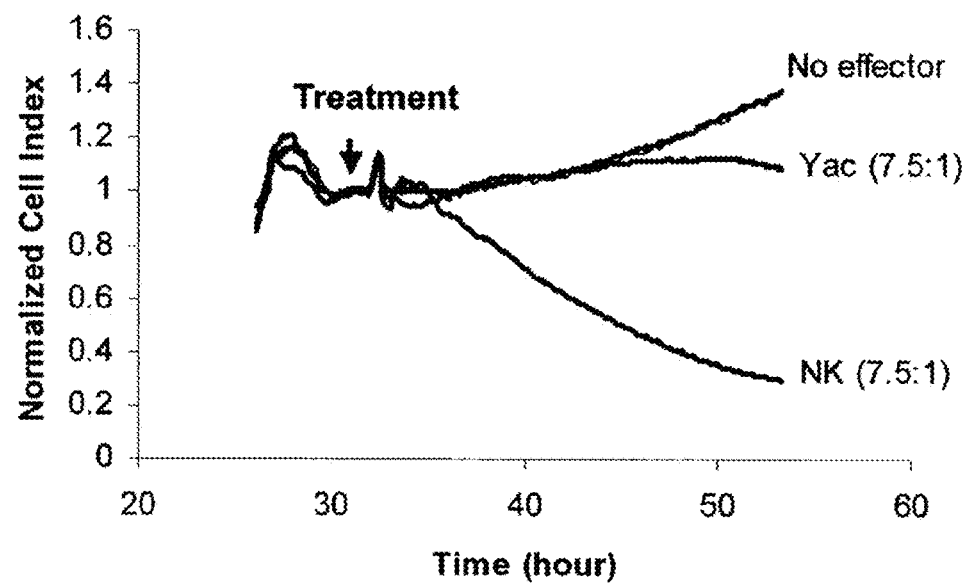
FIG. 23 depicts NIH3T3 cells (target cells) were seeded at a density of 20,000 cells/well on ACEA's microtiter plate (16× E-Plate). The adhesion and proliferation of the NIH3T3 cells were monitored continuously on RT-CES. The cells were allowed to proliferate to log growth phase and then treated with effector NK cells at a ratio effector:target of 7.5:1. As a control the target cells were treated with media alone or with effector cells that lack the killing ability.
Figure 24:
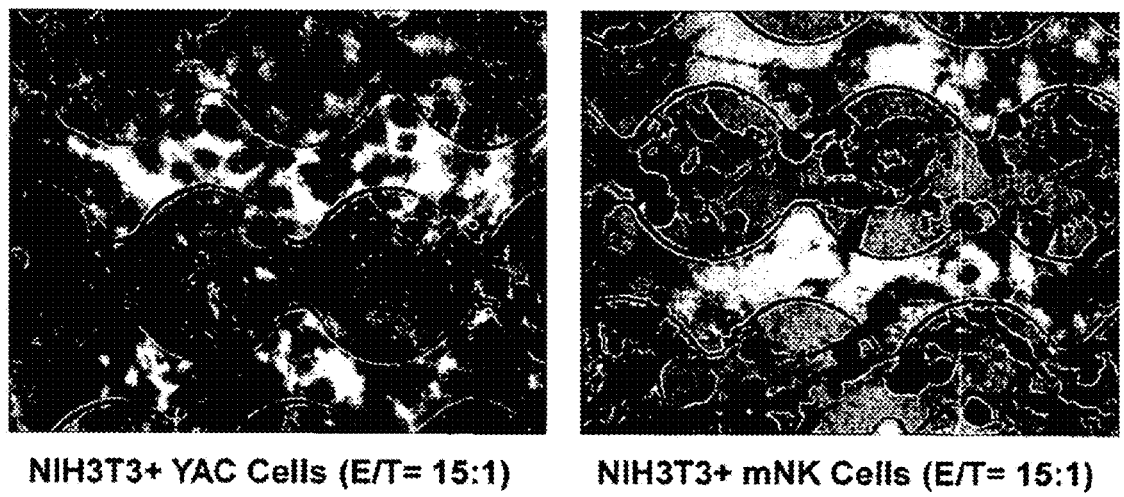
FIG. 24 depicts the NIH3T3 target cells described in FIG. 23 after washing, fixing in methanol and staining with Giemsa blue dye at the end of the assay. The cells were visualized and photographed using a light microscope connected to CCD camera. The cytotoxic effect of the NK cells (effector cells) upon the target cells is apparent by empty gaps in the bottom of the plate, where the target cells have undergone cell death due to interaction with the effector cells. The control effector Yac cell line has no effect on target cells as assessed by the absence of gaps.

NK-Mediated Cell Killing of NIH3T3 Target Cells Using the RT-CES Cell-Substrate Impedance Monitoring System NIH3T3 cells (target cells) were seeded at a density of 20,000 cells/well into wells of ACEA's 16× microtiter plates (16× E-Plate). The cells were monitored continuously using the RT-CES and were allowed to adhere and proliferate overnight. After 18 hours the cells were incubated with effector NK cell line at an effector to target ratio of 7.5:1. The target cell response was continuously monitored for the next 24 hours. As a control a mouse NK cell line which was deficient in its killing ability, Yac, was also added at an effector to target ratio of 7.5:1 or alternatively only 100 µL of media was added to the cells. As indicated by FIGS. 23 and 24, the mouse NK cell line mediates target cell killing as evidenced by a drop in the cell index number over time which is indicative of cell death. On the other hand the control Yac cell line did not have a major effect on target cells as did the addition of media alone. This experiment indicates that effector cell killing of target cells can be monitored in real-time using the RT-CES cell-substrate impedance monitoring system.

Example 6

Testing of Cytolytic Activity in Human and Murine NK Cell Lines

Using the RT-CES system, human and murine NK cell lines were each tested for their cytolytic activities using 9 different target cell lines, including cancer cell lines commonly used in the field. The quantitative and dynamic measurement of NK-cell mediated cytolysis was performed on RT-CES system without any labeling steps and reagents. The experimental results are consistent. Moreover, RT-CES system offers fully automated measurement of the cytolysis in real time, which enables a large scale screening of chemical compounds or genes responsible for the regulation of NK cell-mediated cytolytic activity Cells. The NK 92, the NIH 3T3 cell line, and all the cancer cell lines used in these experiments were purchased from ATCC. The mouse NK cell line (mNK) was provided by Dr. Hui Shao of University of Louisville. All the cell lines were maintained at 37° C. incubator with 5% $CO_2$. The NK92 and mNK lines were maintained in Alpha MEM with 2 mM L-glutamine, 1.5 g/L Sodium bicarbonate, supplemented with 0.2 m inositol, 0.1 mM 2-mercaptoethanol, 0.02 mM folic acid, 12.5% horse serum, 12.5% FBS, and 100-200 U/mL recombinant IL-2. Other cancer cell lines were maintained in RPMI media containing 5% FBS and 1% penicillin and streptomycin (GIBCO). The NIH 3T3 cells were maintained in DMEM media containing 10% FBS and 1% penicillin and streptomycin.

RT-CES system. The system includes three components: the analyzer and e-plate station, the integrated software, and 16-well or 96-well e-plates (16× or 96× E-Plates). The e-plate station or device station is placed inside the incubator and connected to the analyzer outside the incubator through a thin cable. The e-plate containing the cells is placed onto the e-plate station inside the incubator and the experiment data are collected automatically by the analyzer under the control of integrated software.

Cytolytic analysis. Target cells were seeded into the wells of either 16-well or 96-well e-plate in 100 µl of media. Cell growth was dynamically monitored using the RT-CES system for a period of 24-34 hours, depending on the experiment until they reached log growth phase and formed a monolayer. Effector cells at different concentrations were then directly added into individual wells containing the target cells. For background control, effector cells were added to a well without target cells. After addition of the effector cells, the e-plate was returned to the e-plate station and the measurements were automatically collected by the analyzer every 15 minutes for up to 20 hours.

Cell morphology analysis by microscopy. The effect of NK cell-mediated cytolysis on target cells was examined using a Nikon upright microscope. When Cell Index reached 50% of the control upon addition of effector cells, cells were fixed in 80% methanol for 5 minutes and stained with Giemsa blue. The morphology of the cells was examined by microscopy and photographed using an accompanying CCD camera.

Experiment data analysis. The integrated software is able to display entire history of the experiment from seeding the cells to the end of cytolysis. The time- and effector to target ratio (E/T)-dependent curves can be displayed in real time allowing for dynamic monitoring of NK cell activity. The electronic readout, cell-electrode impedance is displayed as a dimensionless parameter called Cell Index. The cell index here is determined by calculating, for each measurement frequency f, the relative-change (Relative change $(f) = (R_{cell}(f) - R_{background}(f))/R_{background}(f)$) in resistance (a component of impedance) of a well when target cells are present in the well ($R_{cell}(f)$) with respect to background resistance ($R_{background}(f)$) of the well when no cell is present and only cell culture medium is in the well, and then finding the maximum relative-change in resistance for all frequencies measured (Cell Index=max {Relative change (f)} for all measurement frequencies). The maximum relative-change in resistance is used as cell index. To quantify the lysis at specific time points, the cell index data was exported from RT-CES software to Microsoft Excel and percentage cytolysis at specific E/T ratio at a given time was determined by comparing the cell index for a well with specific E/T ratio to the cell index of a control well without adding NK cells and calculated using the following equation: Percentage of cytolysis=$(1 - CI_{at\ a\ given\ E/T\ ratio}/CI_{without\ NK\ cells}) \times 100$. Normalized cell index values were used in the calculation of percentage of cytolysis in FIGS. 25B, 26B, 26D, 27A and 27B.

Figure 25A:
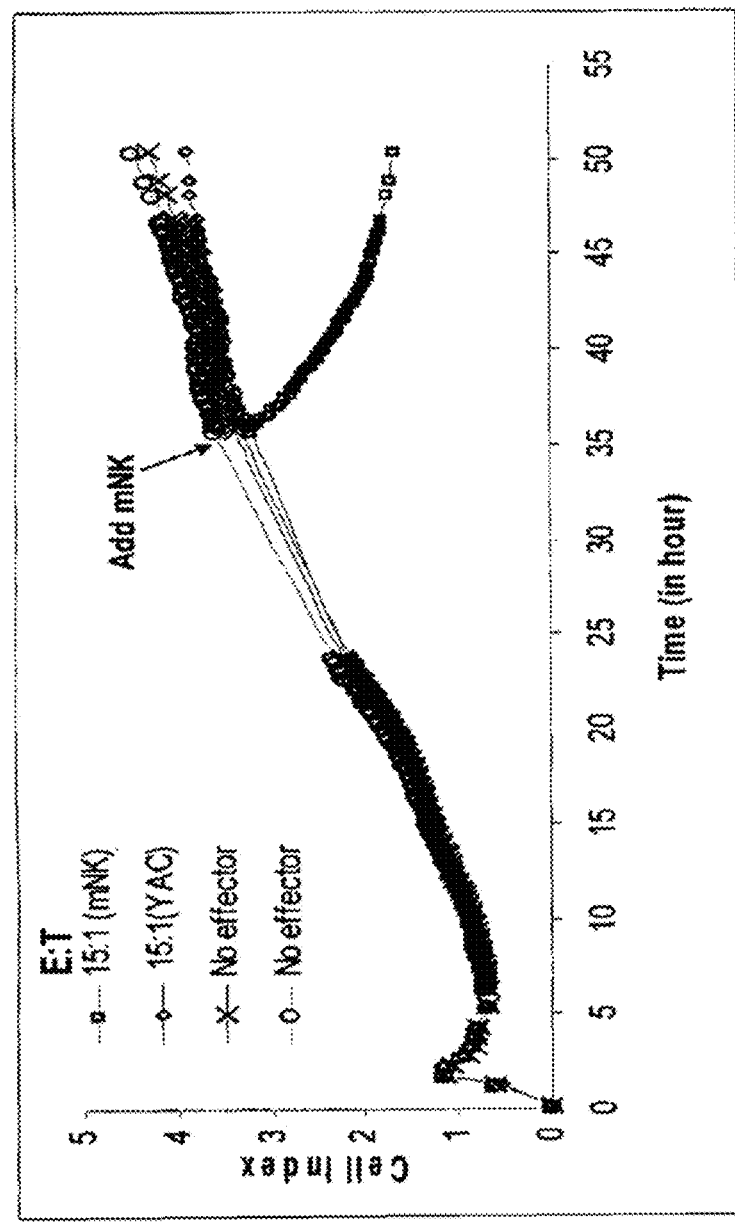
FIGS. 25A-B depict the dynamic monitoring of NK cell-mediated cytolysis on the RT-CES system.
Figure 25B:
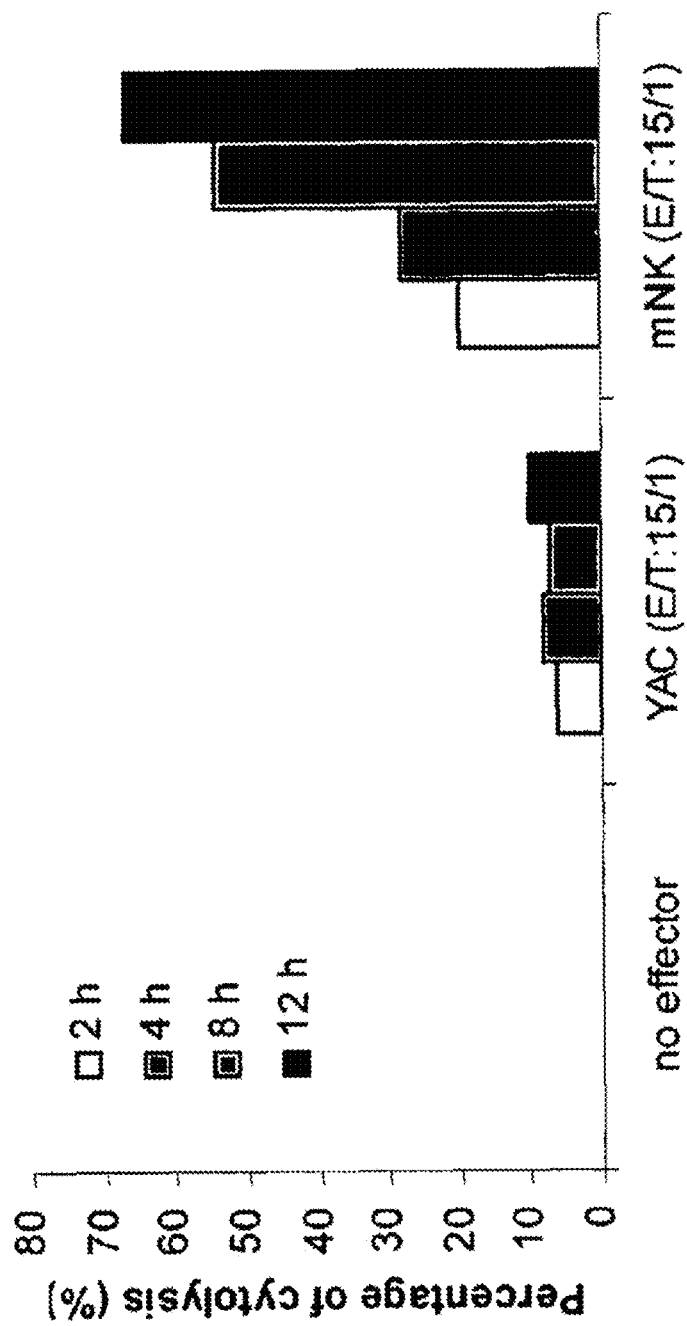

Results and Discussion: Dynamic monitoring of NK cell-mediated cytolysis. To assess NK cell-mediated cytolytic activity using the RT-CES system, a murine NK cell line (mNK line), and a target cell line, NIH 3T3 cells were used. The target NIH3T3 cells were seeded in the wells of 96-well e-plate at 5,000 cells per well and cell growth was continuously monitored on RT-CES system every 60 minutes until the cells reached growth phase, 34 hours later. The effector murine NK cells were then directly added to the well at different E/T ratio, and the NK cell-mediated cytolyses was dynamically monitored on the RT-CES system. As shown in the FIG. 25a, a significant decline of the Cell Index was seen in NIH 3T3 cells after the addition of mNK cells at the E/T ratio of 15 to 1, compared to the Cell Index from the media control. Furthermore, no significant decline of the Cell Index was seen in the effector control wells using YAC cells, a T lymphocyte line without cytolysis effect, indicating the decrease in the Cell Index due to addition of the mNK cells is specific and is most likely mediated by cytolysis. A time-dependent cytolysis of the NIH 3T3 cells was also seen in the presences of mNK cells but not in the presence of YAC cells (FIG. 25B). To further confirm the cytolysis effect, target cells were stained at 8 hours after addition of the mNK cells to target cells, when the cytolysis was approximately 50%, and then examined under microscope (data not shown). In the presence of mNK cells, the target cells were effectively cleared away by the cytolytic action of the mNK when compared to control YAC cells. In summary, RT-CES system offers the only assay format so far to directly monitor NK cell mediated cytolysis without labeling the target cells and without using any chemical reporters. In addition, the entire history of the cytolysis can be dynamically monitored on the RT-CES system, which is difficult to perform by any label-based and endpoint assay format. Analysis of the kinetics of cytolysis indicates that for the mNK cells, a slow cytolysis was detected. The cytolysis is detected within 2 hours of mNK cell addition and interestingly, after 4 hours only less than 30% cytolytic activity is detected. Four hour incubation time is the standard incubation period for radioisotope based endpoint assays. Data obtained by the RT-CES system clearly shows that cytolytic activity can reach up to 70%, which occurs after 12 hours of adding the mNK cells. Such cytolytic activity which occurs after the standard incubation time of the assay can be easily missed by existing label-based, endpoint assays. Therefore, the RT-CES system not only offers label free detection but, more importantly, also allows more accurate assessment of cytolytic activity by dynamically monitoring of the entire history of the cytolysis.

Example 7

Quantitative Measurement of NK Cell-Mediated Cytolysis

Figure 26A:
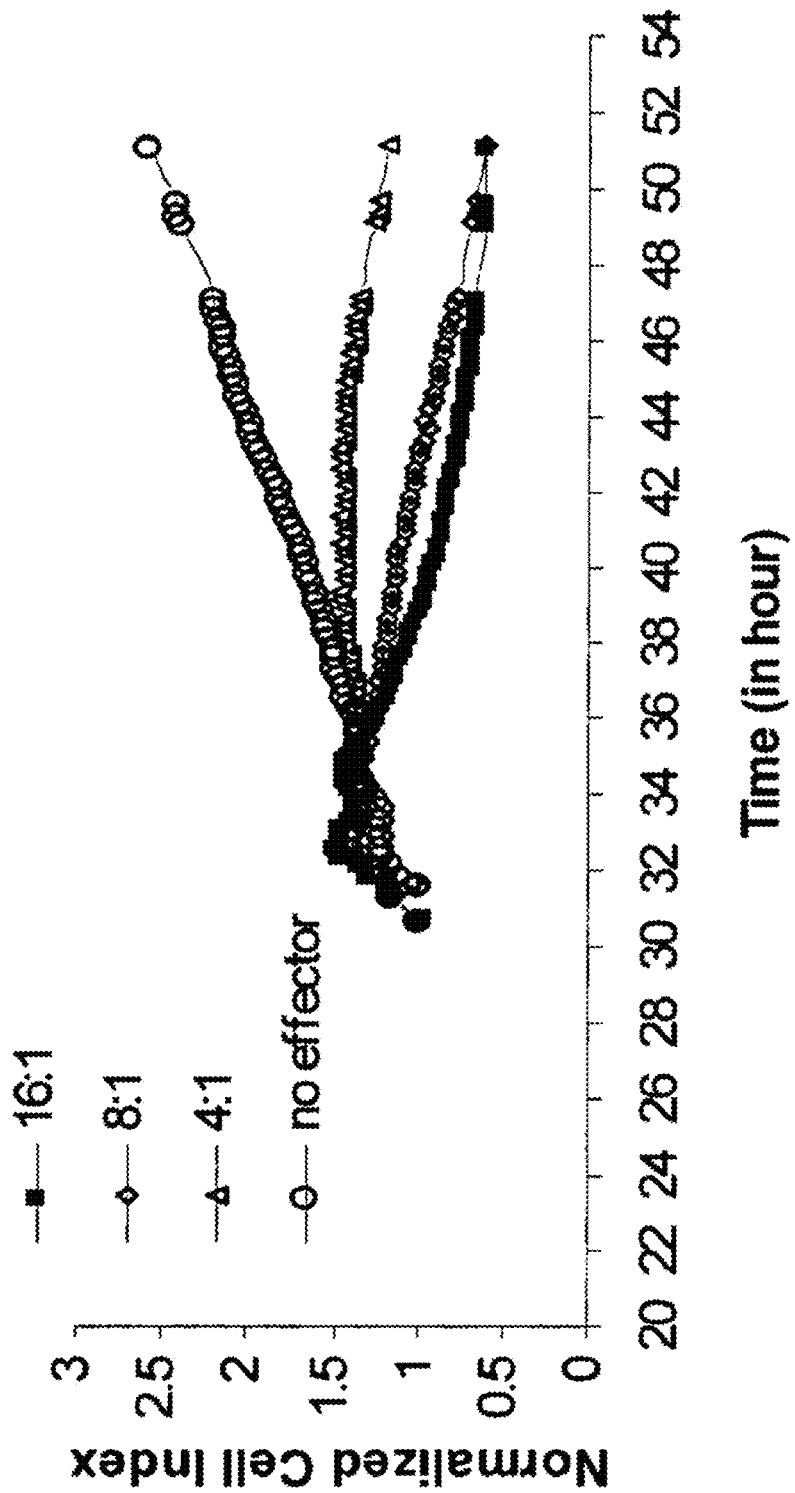
FIGS. 26A-D depict the label free and quantitative measurement of cytolytic activity of mNK cells (murine Natural Killer cells) and NK92 cells.
Figure 26B:
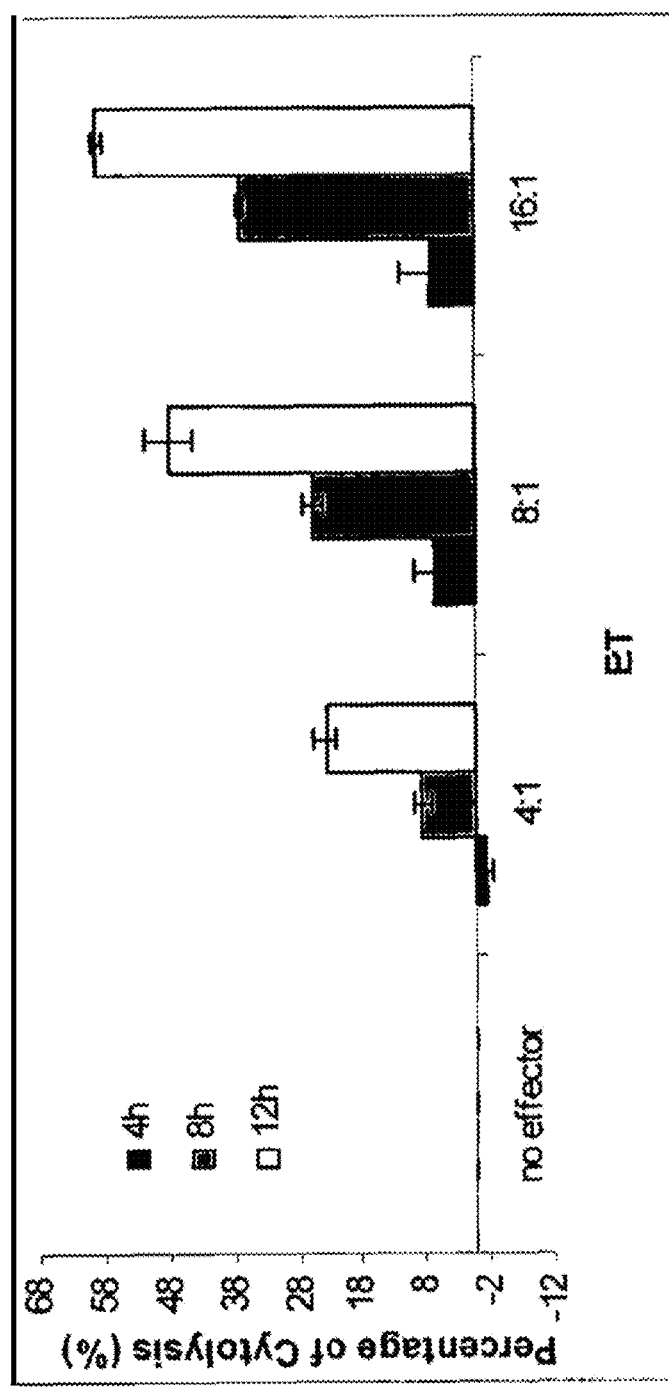
Figure 26C:
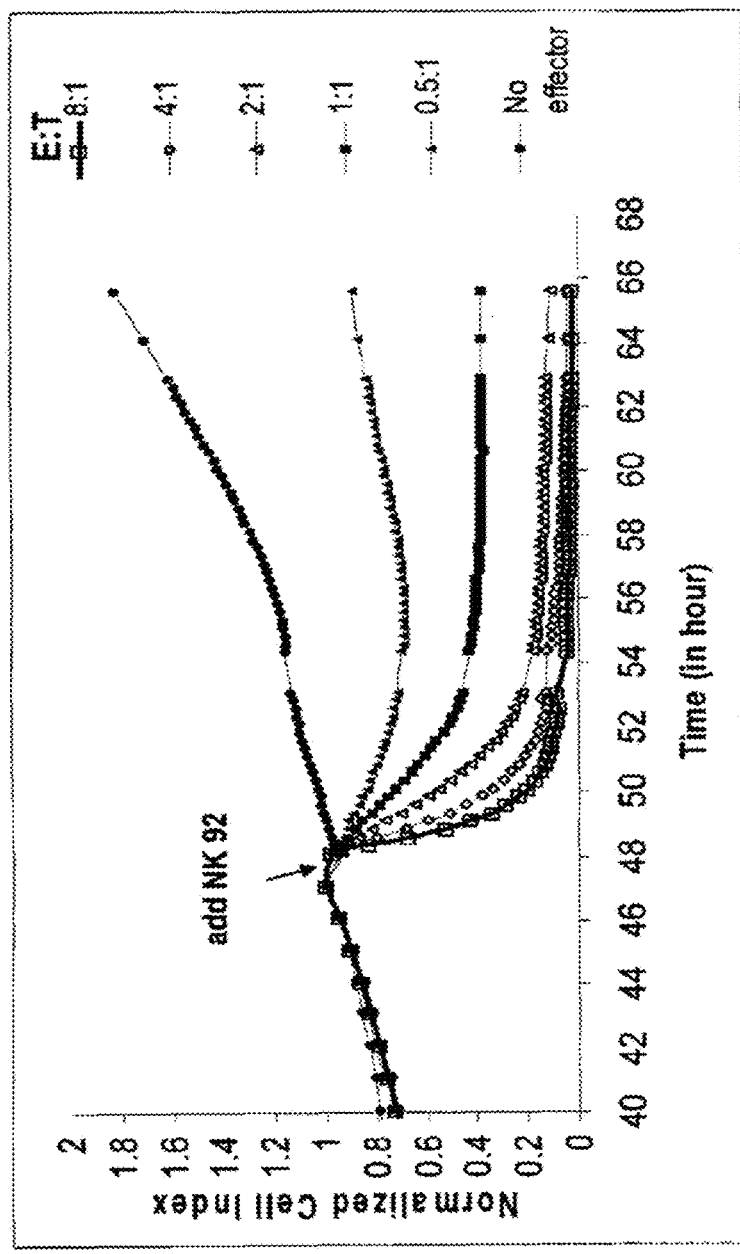
Figure 26D:
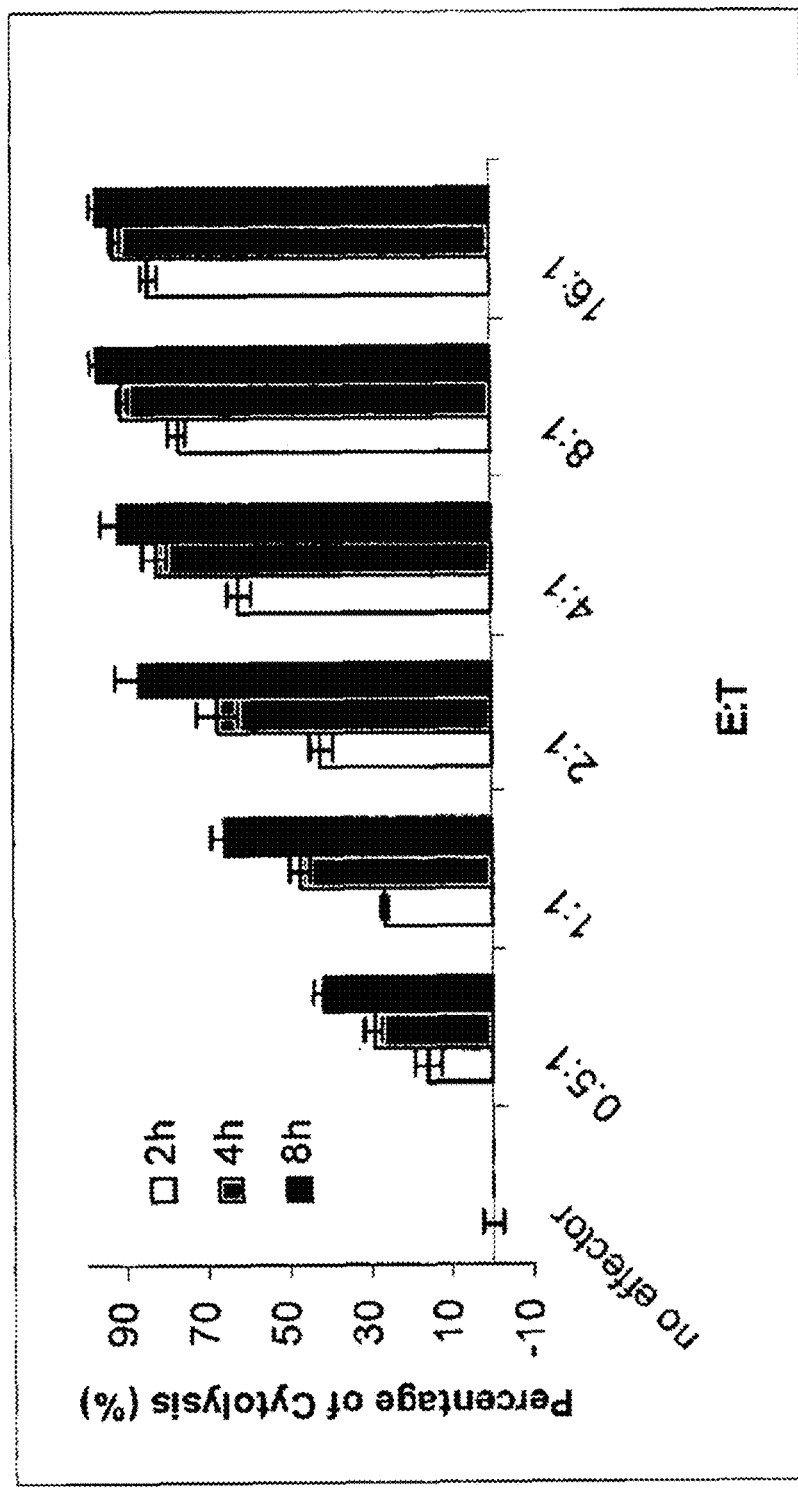

The Cell Index readout of the RT-CES system is correlated with cell number (Solly et al., 2004), and was used to quantitatively monitor cytotoxicity induced by chemical compounds such as anticancer drugs. To test whether mNK cell activity can be quantitatively assayed in the RT-CES system, we monitored cytolysis at different ratios of effector/target. Both murine and human NK cell lines (mNK and NK92) were used as effectors, and the NIH 3T3 line and the MCF7 line (human breast cancer cells) were used as the targets for each of the effectors, respectively. As described above, the target cells were first seeded to the 96 well e-plate at 5,000 cells/well, and the cell growth were then monitored on the RT-CES system. When the target cells reached growth phase, the NK cells were directly added to wells at different concentrations. The NK cell-mediated cytolyses at different E/T ratios were then monitored in real time on RT-CES system. As shown in FIGS. 26A and 26C, subsequent to the addition of mNK or NK92 cells to its target cells, the Cell Indices declined compared to the no effector control. The decline in the Cell Index values is E/T ratio dependent. For either case (FIG. 26A for NIH3T3 cells and FIG. 26C for MCF7 cells), the higher the E/T ratio, the lower Cell Index value was obtained. This strongly indicates that RT-CES system allows for specific and quantitative measurement of NK cell-mediated cytolytic activity. Moreover, the dynamic monitoring of the cytolysis may provide more insights with respect to the underlying mechanisms of NK cell-mediated killing. For example, analysis of the dynamics of cytolysis indicates that the NK92 cells are much more potent effectors than mNK cells. At the E/T ratio of 4 to 1 or higher, greater than 90% cytolysis of the MCF7 can be achieved within 4 hours after addition of NK92 cells (FIG. 26D), whereas as for mNK cells it is only about 30% (FIG. 26b). The different cytolytic kinetics of NK cells indicates the distinct nature of interaction between effector cells and target cells, such as expression of NK receptors and ligands, and mechanisms underlying the NK cell-mediated cytolysis.

Figure 27A:
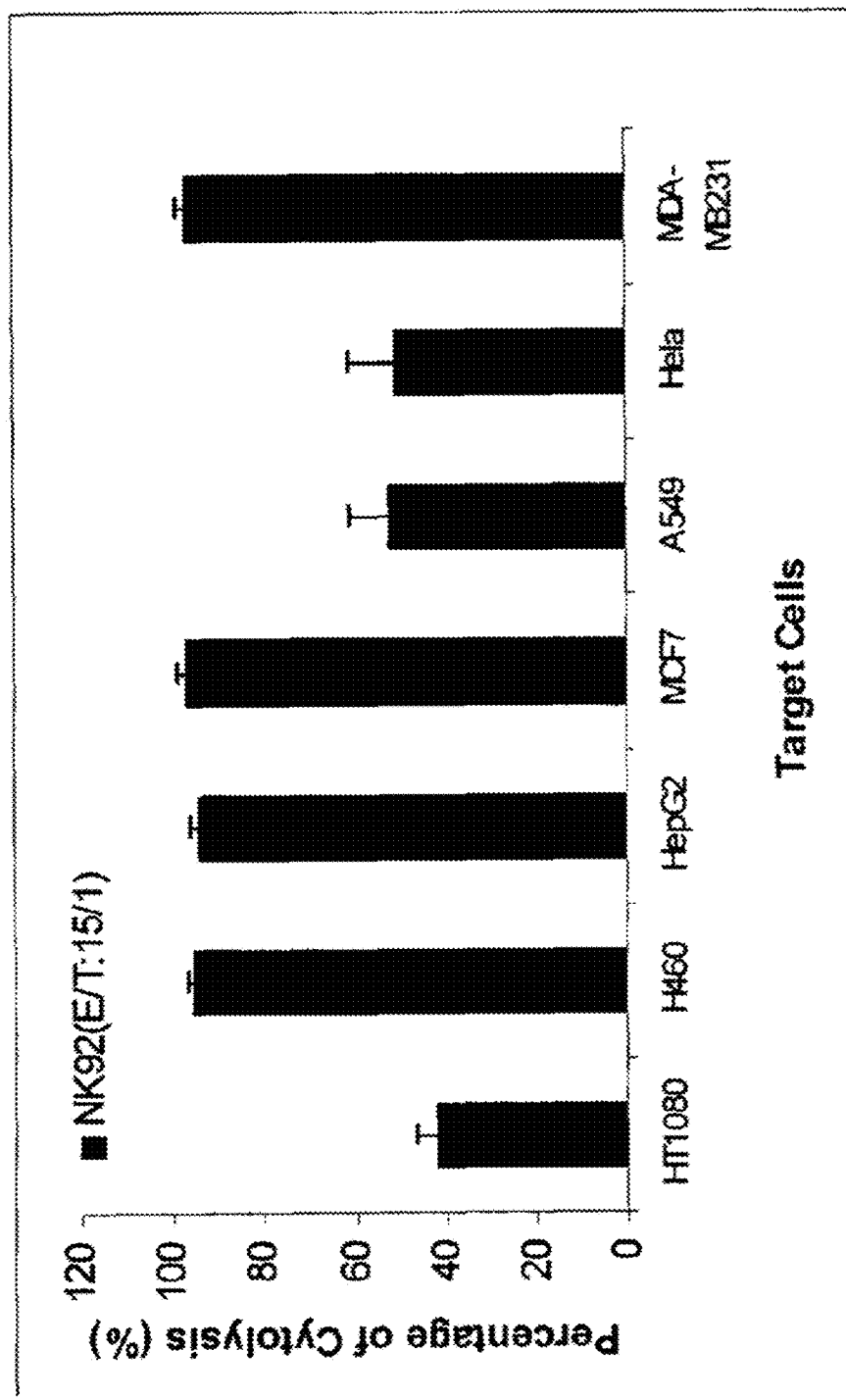
FIG. 27A-B depicts label free assessing cytolysis of a variety of cell lines by NK cells on RT-CES system.
Figure 27B:
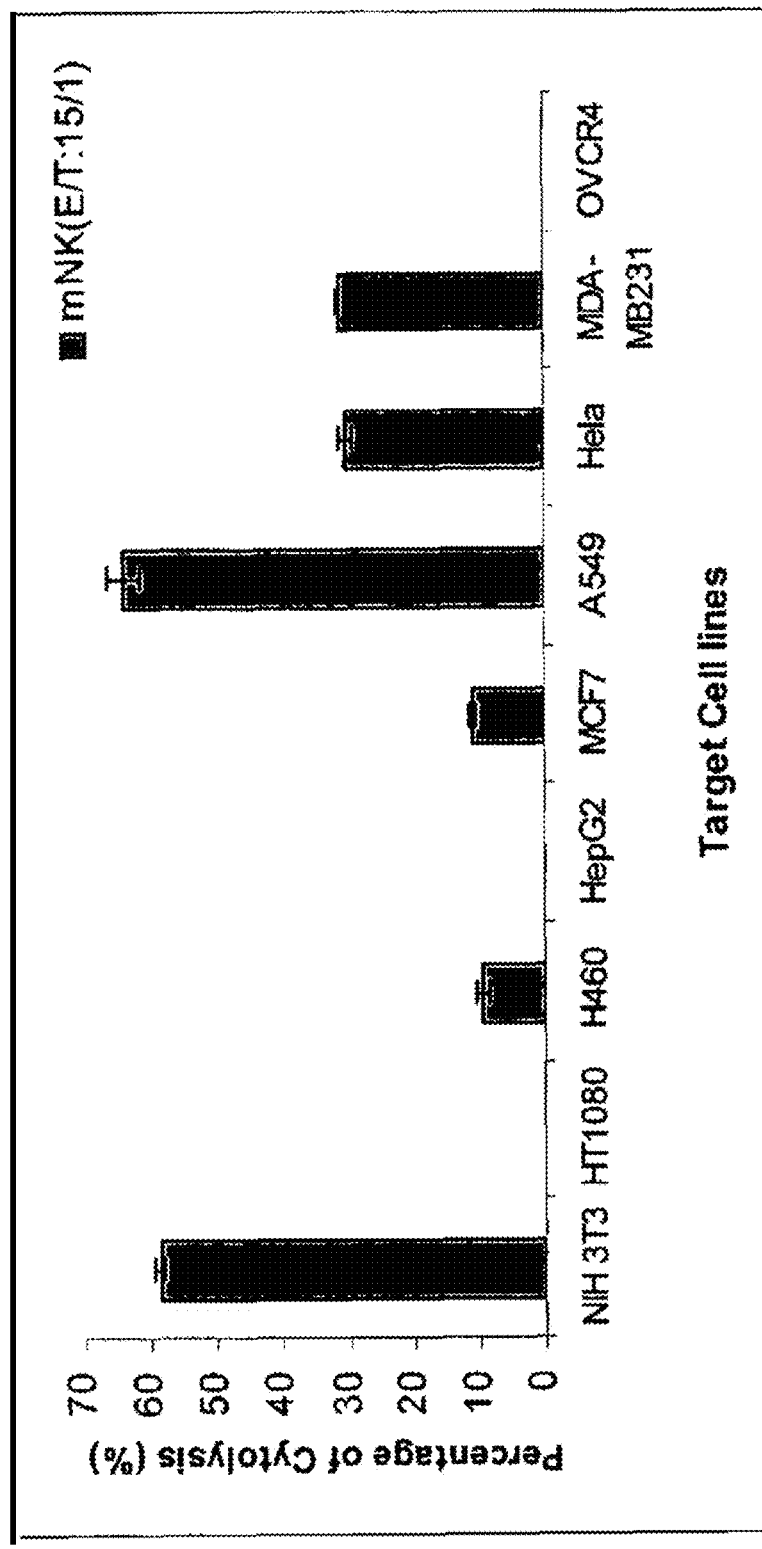
Figure 28A:
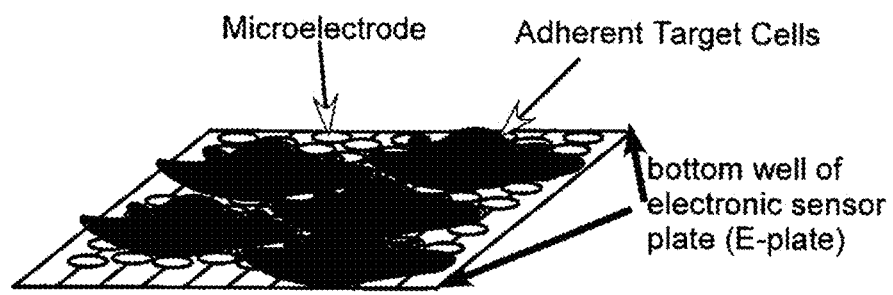
FIGS. 28A-C depicts the underlying principle of the RT-CES system as used for measurement of effector-mediated cytolysis of target cells.
Figure 28B:
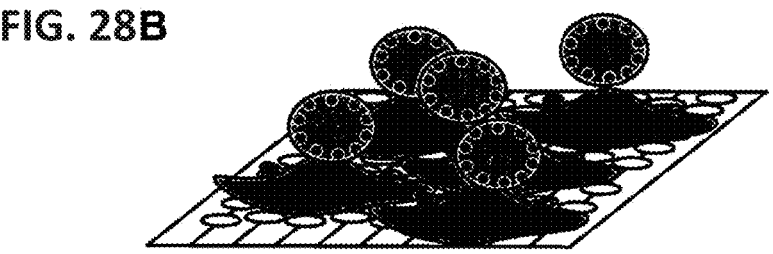
Figure 28C:
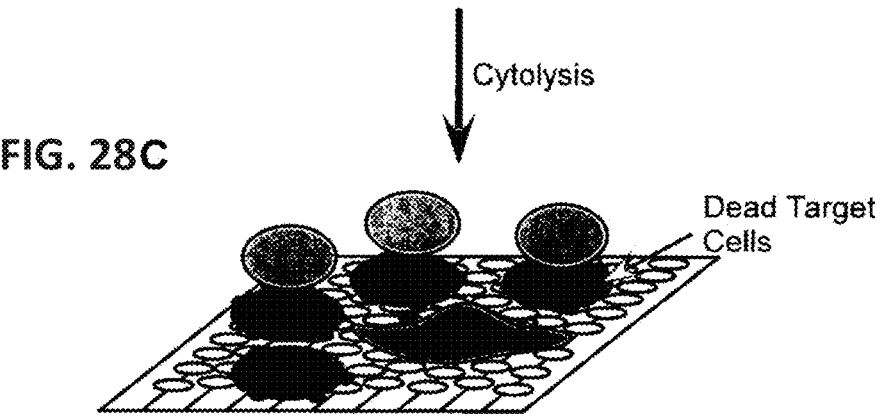

Label free assessment of NK cell cytolytic activity in a variety of target cell lines on the RT-CES system. Cytolytic activities of mNK and NK92 were tested using 9 cell lines, which include 8 different human cancer cell lines and the NIH 3T3 cell line. The susceptibility of different target cells lines to mNK or NK92-mediated cytolysis is summarized in TABLE 4 and TABLE 5. NK92 shows a broad spectrum of cytolytic activity on cancer cell lines. The cytolysis mediated by NK92 occurs fast and reaches the maximum killing activity prior to 8 hours after addition of NK92 cells. The comparison of susceptibility of 7 cancer cell lines to NK92 cells is shown in FIG. 27A. Among 7 cancer target lines, over 90% cytolysis of 4 target lines was achieved, including H460, HepG2, MCF7 and MDA-MB231. In contrast, mNK cell-mediated cytolysis appears to be more selective than NK92 (FIG. 27B). Among 9 target cell lines, 4 target cell lines showed cytolysis of over 30% after 12 hours of incubation with mNK cells, including NIH 3T3, A549, Hela, and MDA-MB231, while no cytolysis (0%) or weak cytolysis (10%) was found in 5 target lines, including OVCR4, HT1080, HepG2, H460 and MCF7. In addition, the cytolysis mediated by mNK was much slower than NK92, reaching the maximum after 12 hours of addition of mNK cells.

TABLE 4 mNK cell-mediated cytolysis of 9 cell lines

| Cell Name | Cell Type | Species | Max Cytolysis (%) at 12 h |
|---|---|---|---|
| NIH 3T3 | Fibroblast | Murine | 58.80 |
| HT1080 | Fibrosarcoma | Human | 0.10 |
| H460 | Nonsmall cell lung cancer | Human | 9.46 |
| HepG2 | Hepatoma | Human | 0.00 |
| MCF7 | Breast cancer | Human | 11.00 |
| A549 | Nonsmall cell lung cancer | Human | 64.00 |
| HELA | Cervix cancer | Human | 30.30 |
| OVCAR4 | Ovarian cancer | Human | 0.00 |
| MDA-MB-231 | Breast cancer | Human | 31.5 |

TABLE 5

NK92 cell-mediated cytolysis of 7 cell lines

| Cell Name | Cell Type | Species | Max Cytolysis (%) at 8 h |
|---|---|---|---|
| HT1080 | Fibrosarcoma | Human | 42.17 |
| H460 | Nonsmall cell lung cancer | Human | 95.40 |
| HepG2 | Hepatoma | Human | 94.10 |
| MCF7 | Breast cancer | Human | 96.50 |
| A549 | Nonsmall cell lung cancer | Human | 52.20 |
| HELA | Cervix cancer | Human | 51.00 |
| MDA-MB-231 | Breast cancer | Human | 97.00 |

Example 8

Dynamic and Label-Free Monitoring of Natural Killer Cell-Mediated Cytolysis of Target Cells Using Cell-Substrate Impedance Monitoring In this example, the RT-CES cell-substrate impedance monitoring system, provides label free assessment of natural killer (NK) cell-mediated cytolytic activity. The RT-CES system was used to dynamically and quantitatively monitor NK-mediated cytolysis of 9 different target cell lines, including cancer cell lines commonly used in laboratories as cancer models. The cytolysis monitored by RT-CES system was compared with standard techniques such as MTT measurement and shows good correlation and better sensitivity. To test the specificity of the assay, pharmacological agents that inhibit NK cell degranulation and cytolysis were employed and was shown to selectively and dose-dependently inhibit NK-mediated cytolysis of target cells. In summary, the RT-CES system offers fully automated measurement of cytolysis in real time, which enables a large scale screening of chemical compounds or genes responsible for the regulation of NK-mediated cytolytic activity.

Cells. The NK 92, the NIH 3T3 cell line, and all the cancer cell lines used in these experiments were purchased from ATCC. The mouse NK cell line (mNK) was provided by Dr. Hui Shao of University of Louisville. All the cell lines were maintained at 37° C. incubator with 5% $CO_2$. The NK92 and mNK lines were maintained in Alpha MEM with 2 mM L-glutamine, 1.5 g/L Sodium bicarbonate, supplemented with 0.2 m inositol, 0.1 mM 2-mercaptoethanol, 0.02 mM folic acid, 12.5% horse serum, 12.5% FBS, and 100-200 U/ml recombinant IL-2. Other cancer cell lines were maintained in RPMI media containing 5% FBS and 1% penicillin and streptomycin (GIBCO). The NIH 3T3 cells were maintained in DMEM media containing 10% FBS and 1% penicillin and streptomycin.

RT-CES system. The system includes three components: the analyzer and E-plate station, the integrated software, and 16-well or 96-well E-plate. The E-plate station is placed inside the incubator and connected to the analyzer outside the incubator through a thin cable. The E-plate containing the cells is placed onto the e-plate station inside the incubator and the experiment data are collected automatically by the analyzer under the control of an integrated software. The principles of RT-CES technology has been described previously (Abassi et al., 2004; Solly et al., 2004; Xing et al., 2005).

Cytolytic analysis. Target cells were seeded into the wells of either 16-well or 96-well E-plate in 100 μL of media. Cell growth was dynamically monitored using the RT-CES system for a period of 24-34 hours, depending on the experiment until they reached log growth phase and formed a monolayer. Effector cells at different concentrations were then directly added into individual wells containing the target cells. For background control, effector cells were added to a well without target cells. After addition of the effector cells, the E-plate was returned to the e-plate station and the measurements were automatically collected by the analyzer every 15 minutes for up to 20 hours.

Cell morphology analysis by microscopy. The effect of NK cell-mediated cytolysis on target cells was examined using a Nikon upright microscope. When Cell Index reached 50% of the control upon addition of effector cells, cells were fixed in 80% methanol for 5 minutes and stained with Giemsa blue. The morphology of the cells was examined by microscopy and photographed using an accompanying CCD camera.

Data analysis. The integrated software is able to display entire history of the experiment from seeding the cells to termination of cytolysis. The time- and effector to target ratio (E/T)-dependent curves can be displayed in real time allowing for dynamic monitoring of NK cell activity. The electronic readout, cell-electrode impedance is displayed as a dimensionless parameter called Cell Index. The cell index here is determined by calculating, for each measurement frequency f, the relative-change (Relative change $(f)=(R_{cell}(f)-R_{background}(f))/R_{background}(f)$) in resistance (a component of impedance) of a well when target cells are present in the well ($R_{cell}$ (f)) with respect to background resistance ($R_{background}$) of the well when no cell is present and only cell culture medium is in the well, and then finding the maximum relative-change in resistance for all frequencies measured (Cell Index=max {Relative change (f)} for all measurement frequencies). The maximum relative-change in resistance is used as cell index. To quantify the lysis at specific time points, the cell index data was exported from RT-CES software to Microsoft Excel and percentage cytolysis at specific E/T ratio at a given time was determined by comparing the cell index for a well with specific E/T ratio to the cell index of a control well without adding NK cells and calculated using the following equation: Percentage of cytolysis=$(1-CI_{at\ a\ given\ E/T\ ratio}/CI_{without\ NK\ cells})\times 100$. Normalized cell index values were used in the calculation of percentage of cytolysis in FIGS. 29C, 31A, 31B, 31C and 31D.

Determination of cytolysis using MTT assay and crystal violet staining. Target cells growing on E-plates were incubated with different ratios of effector cells and incubated overnight. The cytolysis was dynamically monitored using the RT-CES system. At the end of the experiment, the wells were washed in PBS to remove unbound cells and the viable cells attached to the bottom of the E-plate were quantified using MTT reagents according to manufacturers protocols (Sigma) or by fixing the cells with 4% paraformaldehyde followed by staining with 0.1% crystal violet solution in $H_2O$ for 20 minutes. The cells were washed five times to remove the non-specific stain and the stained cells were solubilized in the presence of 0.5% TX-100 overnight. The solubilized stain was measured at wavelength of 590 nm using a plate reader.

Figure 29A:
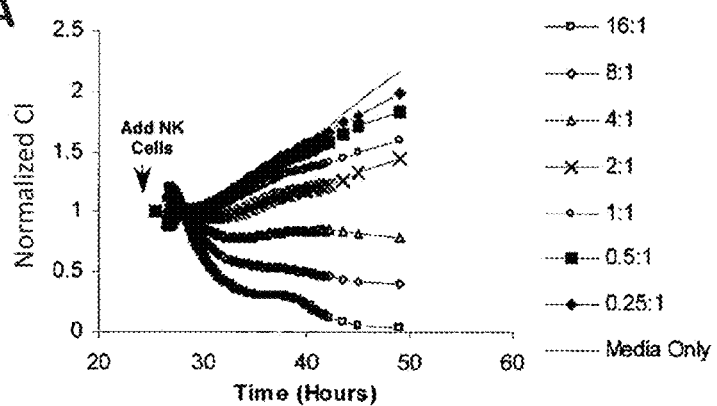
FIGS. 29A-C depict RT-CES monitoring of NK-92 mediated cytotoxicity.
Figure 29B:
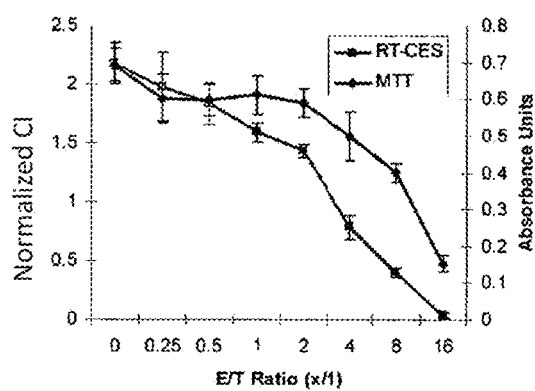
Figure 29C:
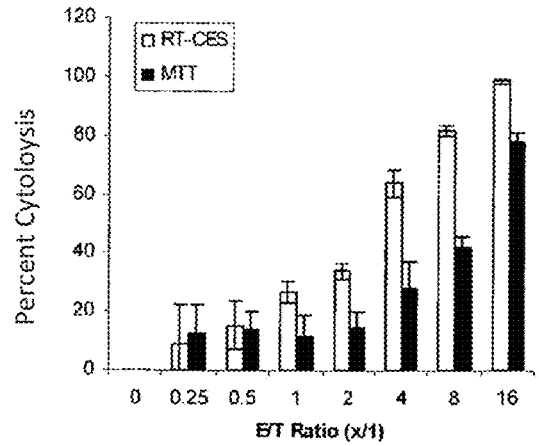

Dynamic monitoring of NK-mediated cytolysis using the RT-CES system. To assess Effector-mediated cytotoxic activity towards target cells we employed NK-92 cell line. NK-92 is a human IL-2 dependent cell line derived from a non-Hodgkin's lymphoma patient that can be easily maintained and propagated in culture and has a very robust cytotoxic activity towards different target cell lines (Gong et al., 1994). NK-92 cell line and some of its derivatives are currently in Phase I clinical trials for the treatment of various cancers (Tam et al., 2003). In order to assess NK-92 mediated cytotoxicity, A549 lung carcinoma cells were seeded in ACEA E-plates at a density of 10000 cells/well and cell growth and proliferation was dynamically monitored using the RT-CES system. Twenty four hours after seeding, NK- cells were added at the indicated effector to target (E/T) ratios (FIGS. 29A-C) and the extent of A549 cell viability was dynamically monitored. As shown in FIG. 29A, NK-92 cell addition to A549 cells leads to a density-dependent decrease in A549 cell index over time, indicating that NK-92 cells are eliciting a cytotoxic effect upon the A549 cells. NK-92 addition to wells which do not contain any A549 cells did not have any appreciable change relative to background (data not shown). Also, A549 cells which were treated with the media alone continue to grow and proliferate (FIG. 29A). In order to compare the cell viability measured by the RT-CES system with a standard assay, at the end of the experiment, the wells of the E-plate were washed to remove the NK cells and any dead cells and the extent of target cell viability was determined by MTT assay. FIG. 29B shows a comparison of the cell index reading to MTT at 50 hours when the experiment was terminated. Overall, the MTT readout correlates very well with RT-CES measurement of cell impedance. In addition to MTT, crystal violet staining of the target cells was also conducted in parallel which confirmed the MTT results (data not shown). The relative cytolytic activity of NK-92 cells towards A549 target cells as measured by both RT-CES system and MTT at different E/T ratios is shown in FIG. 29C. According to FIG. 29C the RT-CES system is more sensitive than MTT in detecting cytolysis, especially at lower E/T ratios.

Figure 30:
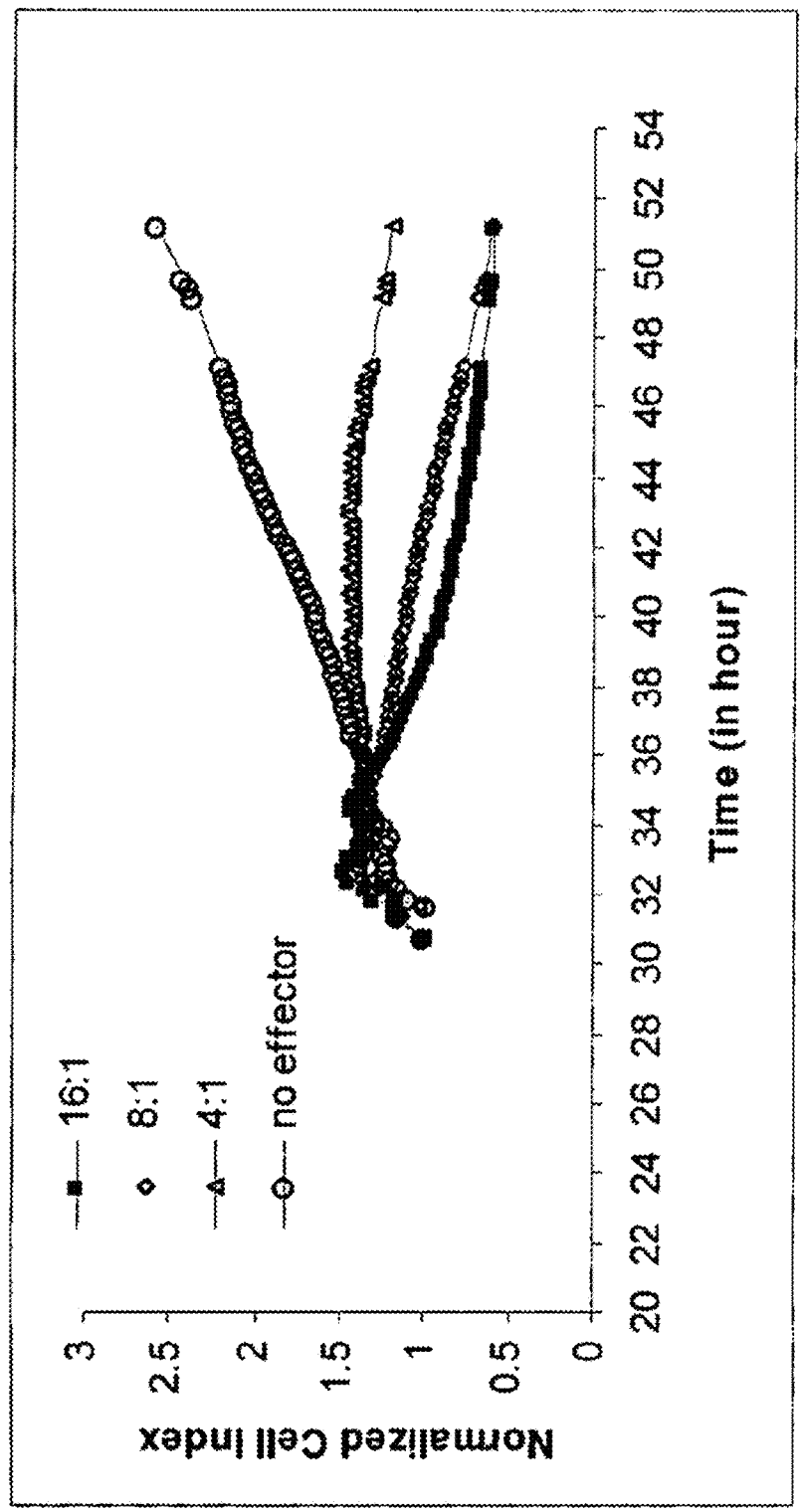
FIG. 30 depicts dynamic monitoring of mouse NK cell cytolysis of target cells using the RT-CES system. NIH3T3 cells were seeded in the wells of E-plate and mouse NK cells, YAC cells, or media alone were added at the indicated time point (arrow) at different E/T ratios. The viability of NIH3T3 cells were continually monitored using the RT-CES system.

In addition to NK-92 cells, the cytotoxic activity of a mouse NK cell line (mNK) was also assessed using the RT-CES system (FIG. 30). NIH3T3 mouse fibroblast cell lines were seeded in E-plates and allowed to grow overnight. Twenty four hours after seeding, NK cells were added to the wells at different E/T ratio and the viability of NIH3T3 cells were continually monitored (FIG. 30). As a control, YAC cells or media alone was added to NIH3T3 cell growing in the wells of the E-plate. The mNK cells induced a progressive decrease in cell index where as addition of YAC cells or media alone had very little effect on the Cell Index recording of NIH3T3 cells (FIG. 30). To ascertain that the progressive decrease in cell index correlates with cytolysis, the cells in the bottom of the E-plate were washed, fixed, stained with Giemsa dye and photographed using a CCD camera attached to a microscope (data not shown). Addition of YAC cells to NIH3T3 cells growing on the bottom of the E-plates, had no detectable effect on the target cells, whereas addition of mNK cells leads to large gaps and areas on the sensors in the bottom of the well that are devoid of target cells, indicating that cytolysis has taken place. In summary, The RT-CES system allows for a non-invasive, label-free and dynamic way of monitoring effector-mediated cytotoxicity activity towards adherent target cells.

Dynamic Monitoring of NK-mediated cytolysis of different target cells using the RT-CES system. Cytolytic activities of mNK and NK92 were tested using 9 cell lines, which include 8 different human cancer cell lines and the NIH 3T3 cell line. The susceptibility of different target cells lines to mNK or NK92-mediated cytolysis is summarized in TABLE 4, and TABLE 5. NK92 shows a broad spectrum of cytolytic activity on cancer cell lines. The cytolysis mediated by NK92 occurs fast and reaches the maximum killing activity prior to 8 hours after addition of NK92 cells. Among 7 cancer target lines, over 90% cytolysis of 4 target lines was achieved, including H460, HepG2, MCF7 and MDA-MB231. In contrast, mNK cell-mediated cytolysis (TABLE 4) appears to be more selective than NK92 (TABLE 5). Among 9 target cell lines, 4 target cell lines showed cytolysis of over 30% after 12 hours of incubation with mNK cells, including NIH 3T3, A549, HeLa, and MDA-MB231, while no cytolysis (0%) or weak cytolysis (10%) was found in 5 target lines, including OVCR4, HT1080, HepG2, H460 and MCF7. In addition, the cytolysis mediated by mNK was much slower than NK92, reaching the maximum after 12 hours of addition of mNK cells.

Figure 31A:
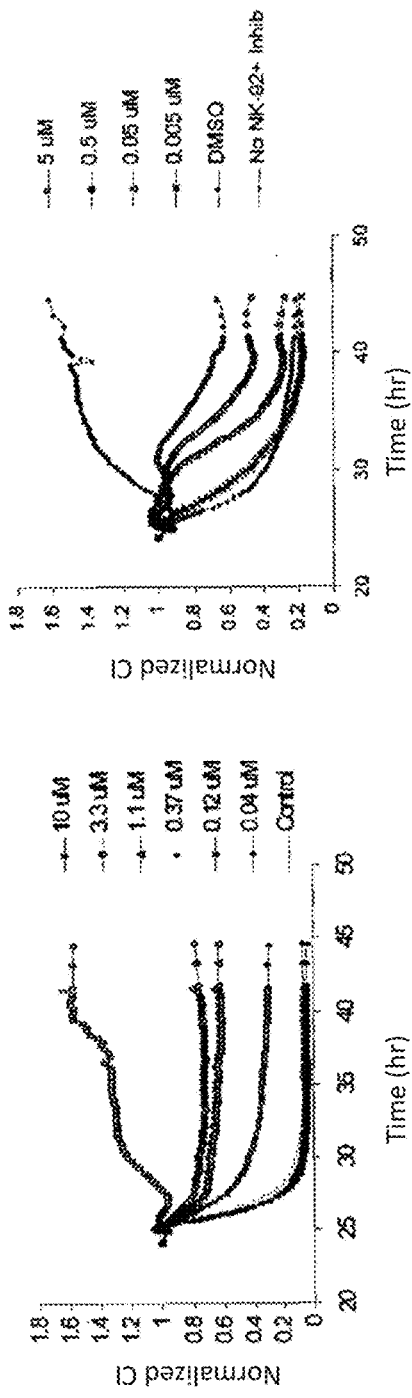
FIGS. 31A-D demonstrate the specificity of NK-92 mediated cytolysis of target cells.
Figure 31B:
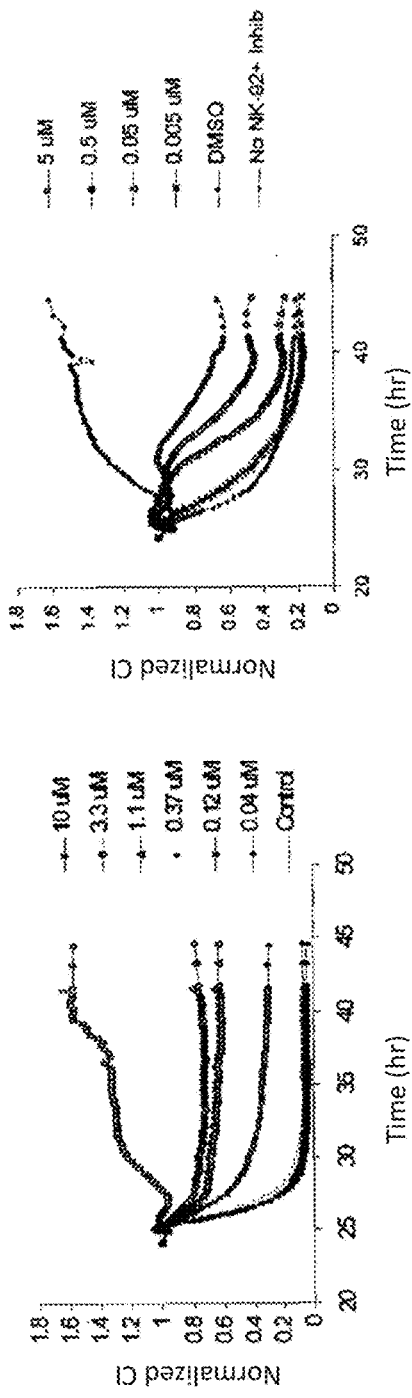
Figure 31D:
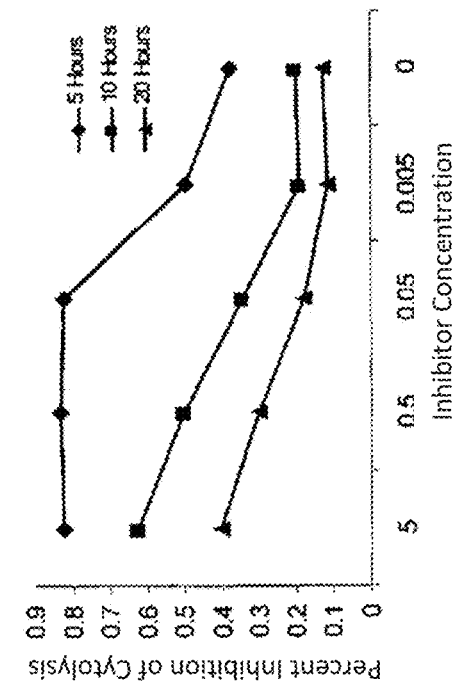
Figure 31C:
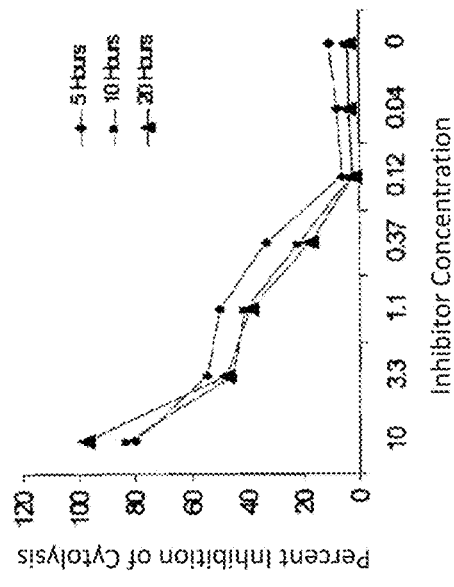

Inhibition of NK-mediated cytolysis of target cells by agents which block the signaling pathways leading to cytotoxicity. The interaction of NK receptors at the cell membrane by target cells leads to the activation of signal transduction machinery which results in cytolysis of target cells (Vivier et al., 2004). One of the key signaling cascades which regulate the fusion of perforin and granzyme containing secretory granules at the NK/target cell synaptic junction is the phosphatidyl-inositol-3-kinase (PI3K), Rac and mitogen activated protein kinase 1 (Erk) pathway (Djeu et al., 2002; Vivier et al., 2004). In order to determine the specificity of the signaling pathways in regulating NK-mediated cytotoxicity, we therefore sought to utilize specific inhibitors of the PI3K and Erk pathways. NK-92 cells were incubated with both the PI3K inhibitor Wortmannin and the Erk pathway inhibitor PD98059 or DMSO as a control and then added to A549 target cells. As shown in FIG. 31A-D, both Wortmannin and PD98059 dose-dependently inhibited NK-92-mediated cytolysis of A549 cells as monitored by the RT-CES system. As an additional control, A549 target cells were also incubated with both Wortmannin and PD 98059 alone which had minimal effect on the baseline. We calculated percent inhibition of cytolysis for both inhibitors at different time points after NK addition. While the Erk pathway inhibitor resulted in consistent inhibition of cytolysis at all the indicated time points (FIG. 31B), the PI3K inhibitor-mediated inhibition of cytolysis clearly depends on the time point at which the analysis is performed (FIG. 31D). In summary, the experiments shown here clearly establish that the RT-CES system can be used to monitor NK-mediated cytotoxic activity against a variety of different cell lines. Furthermore, interfering with the NK-mediated cytotoxicity response by using inhibitors of the signaling cascade regulating granule fusion significantly attenuates the cytotoxicity response as measured by the RT-CES system. The data also shows that the extent of inhibition can primarily depend on the length of NK incubation with target cells and provides a good rationale for dynamic monitoring of effector-mediated cytotoxicity.

Discussion NK cells play a central role in innate immune response as well as an intermediary role in bridging the gap between innate immunity and adaptive immunity (Lanier, 2005). NK cells have specialized organelles or granules which house cytolytic enzymes and proteins that are responsible for its cytolytic activity upon encountering pathogen infected cells or tumors (Smyth et al., 2002; Smyth et al., 2005). Recently a number of receptors have been identified on the surface of NK-cells which regulate NK-mediated cytotoxicity in a positive or negative manner depending on the identity of the target cell (Lanier, 2005).

In this report we have described a label-free and real-time assay for monitoring NK-mediated cytotoxicity towards different adherent target cells. The assay is based on monitoring the viability of target cells growing on electronic cell sensor arrays fabricated in the bottom well of microtiter plates (E-plates) The interaction of the cells with sensors generates an impedance response which is indicative of the general health of the cell. We have used both human and mouse NK-cells to demonstrate that NK-mediated cytotoxicity activity can be monitored using the RT-CES system, composed of a monitoring system as well as E-PLATES which contains the microelectrodes for detection of target cells (Abassi et al., 2004; Solly et al., 2004; Xing et al., 2005). NK-mediated cytotoxicity as monitored on the RT-CES system correlates with standard assays such as MTT and crystal violet staining of target cells to assess effector-mediated cytotoxicity (FIG. 29A-C). Both of these assays have been used to monitor effector-mediated cytolysis of target cells (Wahlberg et al., 2001; Peng et al., 2004). The release of granules containing the lytic proteins and proteases is regulated by receptor-mediated signal transduction cascade. Specifically, it has been shown that the PI3K and ERK pathways play a major role in granule exocytosis and cytotoxicity in addition to cytokine secretion (Djeu et al., 2002; Vivier et al., 2004). Using the RT-CES system and confirming earlier data we were able to demonstrate that interfering with the PI3K and Erk pathways by means of small molecular inhibitors blocks NK-mediated cytolysis of target cells (FIG. 31A-D). The extent of the inhibition of cytolysis with different pathway blockers depends on the duration of incubation of NK cells with target cells (FIG. 31B and FIG. 31D). Utilizing standard single point assays such as chromium release assay (CRA), it would've been easy to miss the time-dependent effect of the inhibitors upon cytolysis.

Example 9

BiTe-Mediated Cell Killing of Target Cells

Immunotherapy is emerging as one of the most promising approaches in cancer treatment, allowing specific killing of cancer cells mediated by cytotoxic T-cells, through the recognition of specific markers expressed on the surface of cancer cells. Antibody-Dependent Cellular Cytotoxicity (ADCC) was one of the first immunotherapeutic approaches to achieve clinical trials and involves the activity of different type of immune effector cells. In the Chimeric Antigen T-cell Receptor (CAR-T) approach, patient's T lymphocytes are engineered to express chimeric receptors that bind tumor cell antigens and activate T-cell's cytotoxic activity. Bispecific T-cell Engager (BiTE) antibodies instead are engineered bivalent proteins that promote the interaction between tumor cells and T lymphocytes trough simultaneous binding of a tumor cell marker and the T cell specific receptor CD3. Through this dual interaction, BiTE antibodies induce the formation of cytolytic synapses and thus direct specific lysis of target tumor cells through a cascade of cytotoxic events, including release of perforins and granzymes, which compromise the cell membrane integrity. Subsequently, activation of caspases induces fragmentation of DNA, morphological changes, and ultimately apoptosis of target cells.

Figure 32A:
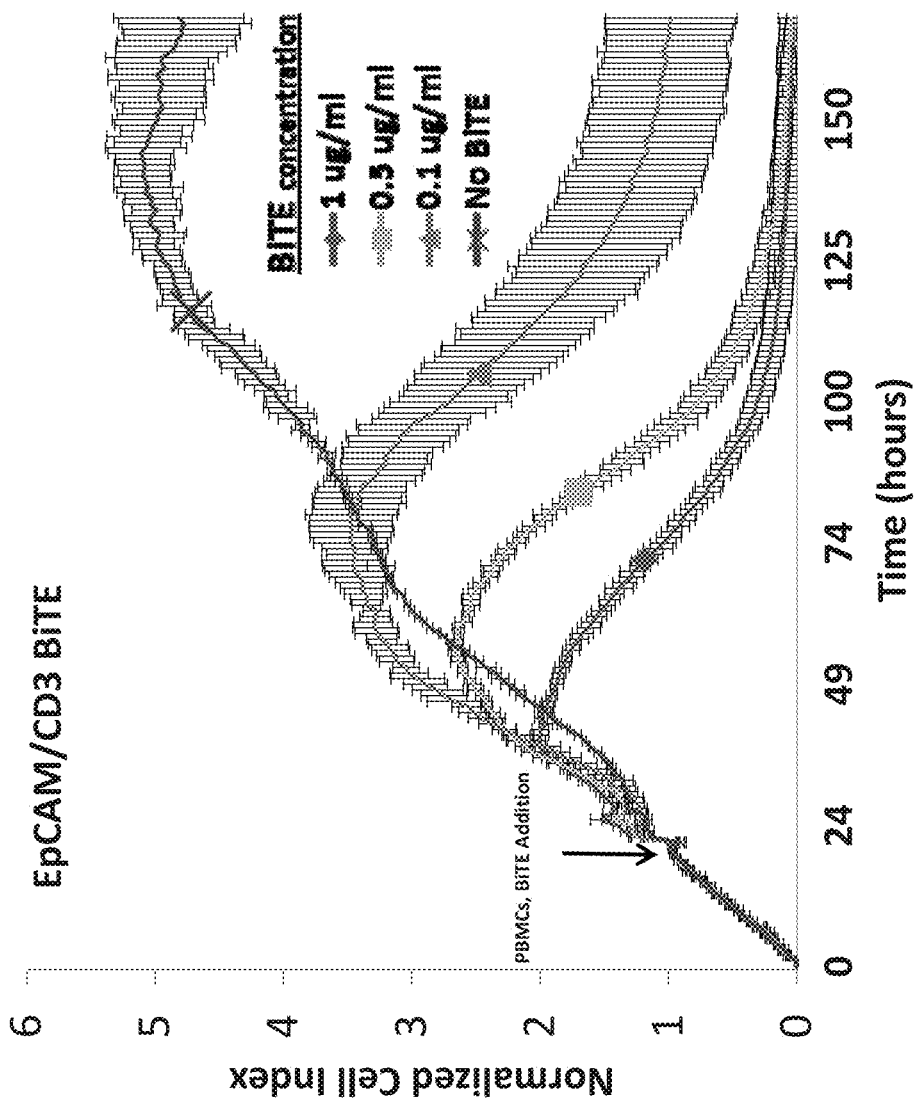
FIG. 32A depicts a graph showing that the addition of EpCAM/CD3 BiTE antibody promotes PBMC-dependent lysis of PC3 prostate cancer cells. PC3 cells were seeded at a density of 10,000 cells/well in E-plate 96 and treated after 24 hour with increasing amount of EpCAM/CD3 BiTE and freshly isolated PBMCs at an effector:target ratio of 20. While PBMCs without BiTE have no effect on the exponential phase of the PC3 growth curve (X), increasing amounts of BiTE killed the cancer cells and induced a reduction in the normalized CI parameter. CI was normalized at the last recording data point before PBMCs addition.

To determine if the use of BiTE antibodies will redirect immune cells to recognize and kill cancer cells, we utilized a specific EpCAM/CD3 BiTE on PC3 prostate cancer cells. Epithelial cell adhesion molecule (EpCAM) is a transmembrane glycoprotein mediating Ca'-independent cell-cell adhesion in epithelia and is involved in cell signaling, migration, proliferation, and differentiation. It is also overexpressed in many carcinomas, where contributes to proliferative and antiapoptotic signals. The target PC3 cells were seeded on E-Plate 96 at a density of 10,000 cell/well and let grow for 24 hours. PBMCs were freshly isolated and added in combination with the EpCAM BiTE antibody at an effector:target ratio of 20 in quadruplicate samples. CI was normalized at the last recording data point before PBMCs addition. The addition of PBMCs alone was not able to affect the growth of the cancer cells, which increase in number was reflected by the increase in normalized CI parameter over the successive five days. CI increase ended when cells reached confluency (FIG. 32A, trace X). In presence of the EpCAM BiTE instead the CI started to drop up to the 0 initial background value measured before PC3 addition. The kinetic of CI decline was proportional to BiTE amount, with the highest concentration inducing reduction in the CI after only twelve hours from PBMCs addition (FIG. 32A: diamond trace). The lowest tested concentration was still able to induce cell killing, but the initial decline in CI was visible only 28 hours after adding the effector cells. Furthermore, such concentration seemed to be unable to induce complete killing of the cells, with the CI curve reaching a stationary value of 1 around the end of the assay (FIG. 32A: triangle trace). Taken together, these data demonstrate the ability of the xCELLigence platform to detect kinetic differences in cell killing in relation to BiTE titration.

Figure 32B:
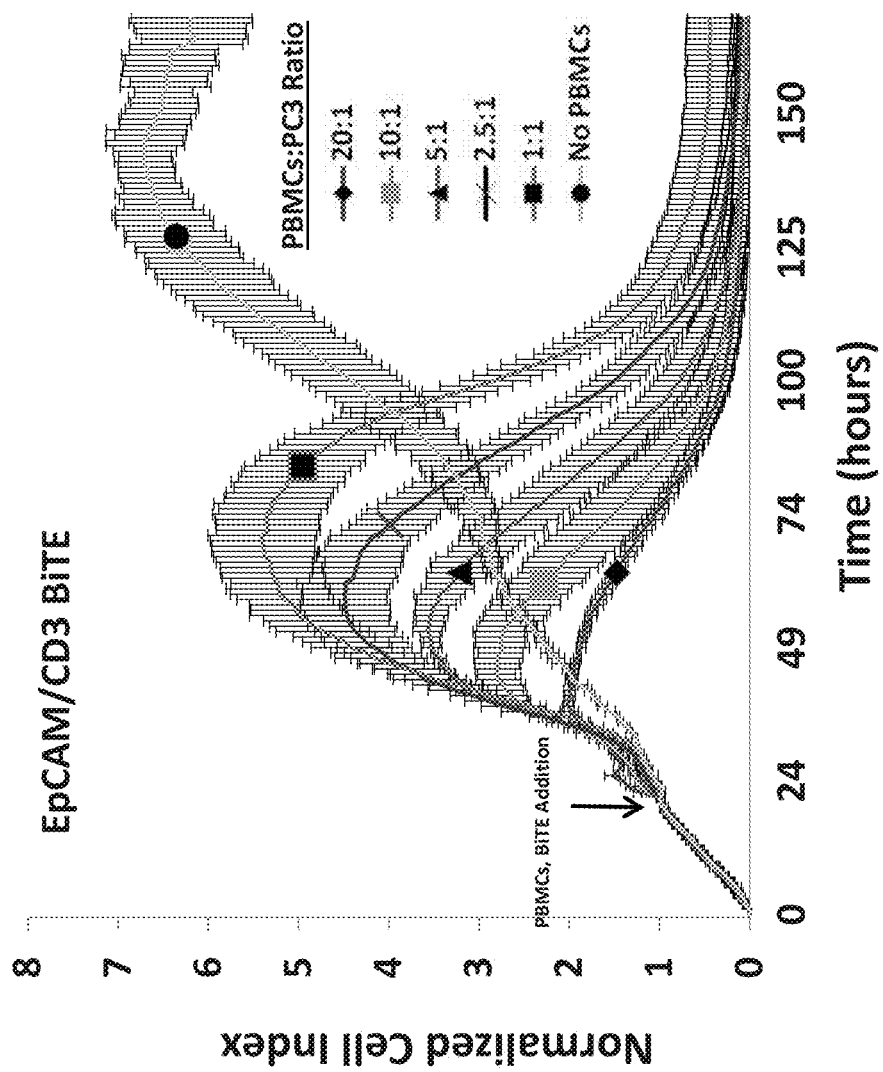
FIG. 32B shows that PBMCs titration demonstrates high sensitivity of impedance reading and specificity of cell killing. PC3 cells were treated with 1 µg/ml EpCAM/CD3 BiTE and increasing amount of effector:target ratios. The figure shows proportionality between ratio and killing kinetic and also the effectiveness of the 1:1 ratio.

We also evaluated the ability of the xCELLigence platform to detect differences in killing kinetic due to variations in effector:target ratio. This is of particular interest because despite the contribute of immune cells to CI is negligible, there is still the possibility that alterations in CI linearity due to PBMCs amount can affect the ability to compare samples with different ratios. Furthermore, cancer patients often have multiple cycle of chemotherapy and are immunocompromised. Thus, it is imperative to evaluate if even small amounts of immune cells can be effectively activated in presence of the BiTE. In the experiment described in FIG. 32B we maintained constant EpCAM/CD3 BiTE concentration with varying the effector:target ratio. Every effector cell concentration was effective in killing the cancer cells, and even an equimolar proportion between PBMCs and PC3 was still able to induce effective killing of cancer cells, even though with longer kinetic and incomplete (FIG. 32B, dark square). Such sensitivity is hard to achieve with end point approaches like Chromium-51 and flow cytometry. Samples with no PBMCs (FIG. 32B, dark circle) had a profile similar to the control without BiTE, demonstrating almost no effect of the immune cells alone on CI measurement.

Figure 33A:
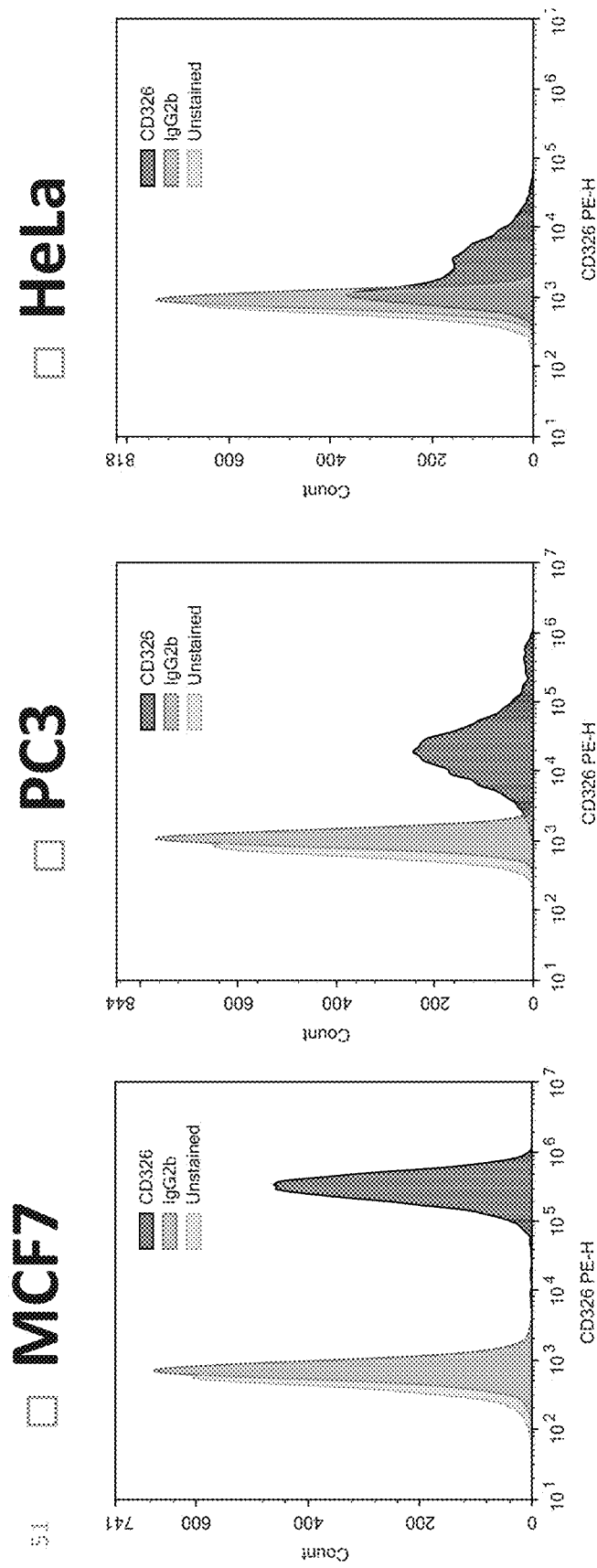
FIG. 33A-D show that kinetic of EpCAM BiTE-mediated cell killing in cancer cell lines with different amount of surface EpCAM protein.

The different strategies developed for cancer immunotherapy rely on specific targeting of cancer cells from the immune system through antigens that are expressed on the surface of cancer cells. However, because of the heterogeneous nature of virtually all solid tumors, differences in the level of expression of the targeting antigen may affect the efficiency of cell killing, with tremendous impact on the outcome of the treatment. We have utilized three different cancer cell lines to test if the kinetic of cell killing can be affected by the amount of surface EpCAM expression. We used the NovoCyte Flow Cytometer (ACEA Biosciences) to measure EpCAM surface levels in PC3 prostate, MCF 7 breast and HeLa cervix human cancer cell lines (FIG. 33A). MCF7 express the highest level of antigen, while PC3 have 10 folds less expression with the exception of a very small subpopulation that shows the same intensity of MCF7. Half the population of HeLa has no expression of EpCAM, while the rest of the cells do express EpCAM, but with intensity 100 folds less than MCF7 and 10 folds less than PC3. Therefore, the three cell lines represent a continuous spectrum of EpCAM antigen variation.

Figure 33B:
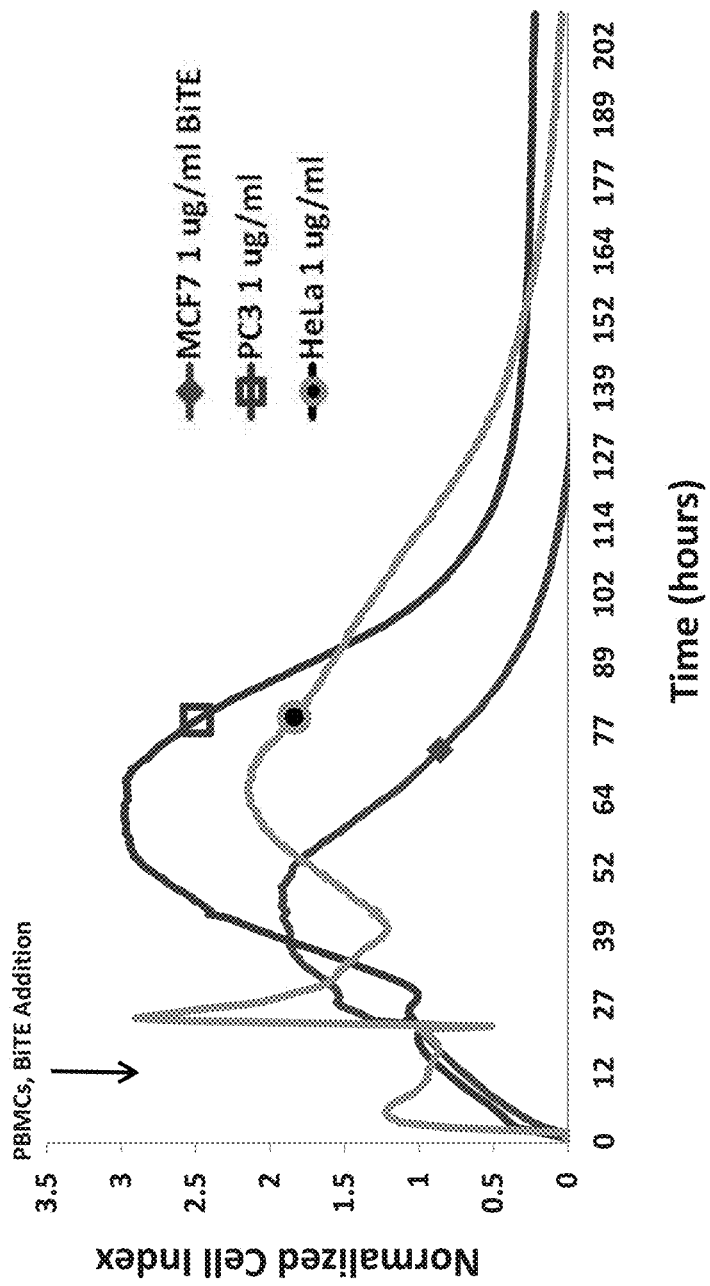

In one single experiment, we treated the three different cell lines with the same amount of EpCAM BiTE antibody and PBMCs:cancer cells ratio (FIG. 33B). While in MCF7 the addition of PBMCs induces an immediate increase of the Cell Index followed by a decline that reaches the 0 value in less than 90 hours, In PC3, the same antibody needs more than 115 hours to reach the plateau that is still higher than 0. The initial increase in CI is also delayed of 4 hours compared to MCF7. In HeLa, the same antibody still induces an initial increase in CI followed by progressive decline, but slower than the two other cancer cell lines.

Figure 33C:
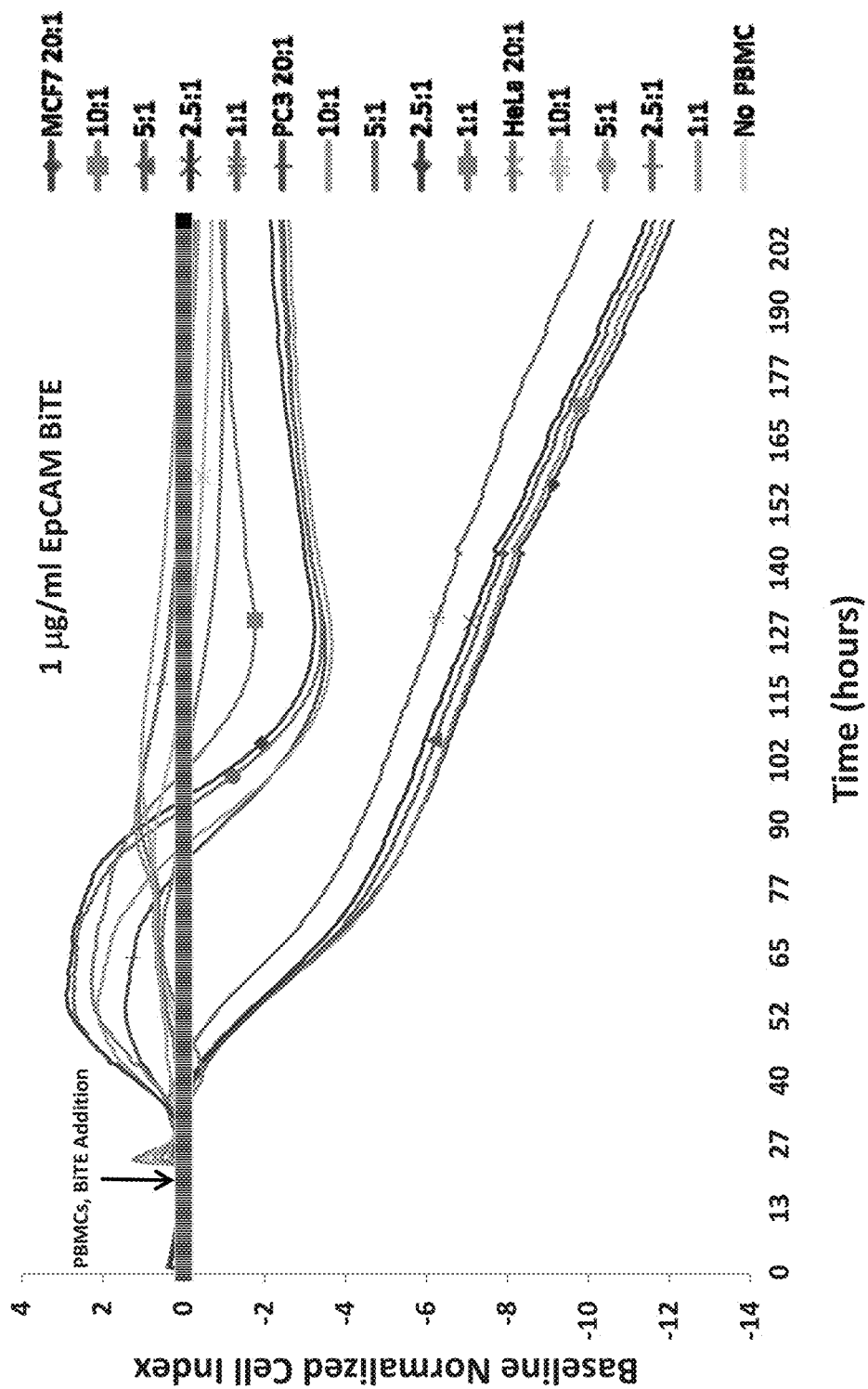

To better identify kinetic differences related to EpCAM expression and amount of added PBMCs we used the control wells with antibody treatment but without PBMCs to set up a baseline against which every different amount of effector cells ratio would be plotted as relative variation. This baseline normalization was done for every cell line using the respective control group and the curves were combined in one single plot for each BiTE concentration (FIG. 33C). The color-coded graph immediately underlines kinetic differences between experimental conditions. In all cell lines there is a reduction of the negative slope of the curve when the amount of effector cells is reduced (FIG. 33C: dark to light colors). Even the time where the declining curve intercepts the horizontal axis increases in proportion to the lower amount of PBMCs. This point marks with good approximation the time where cell killing is affecting the large majority of the cancer cells. Comparing the different cell lines it is clearly visible the difference in kinetic, with MCF7 starting the CI decline several days before PC3 and HeLa.

Figure 33D:
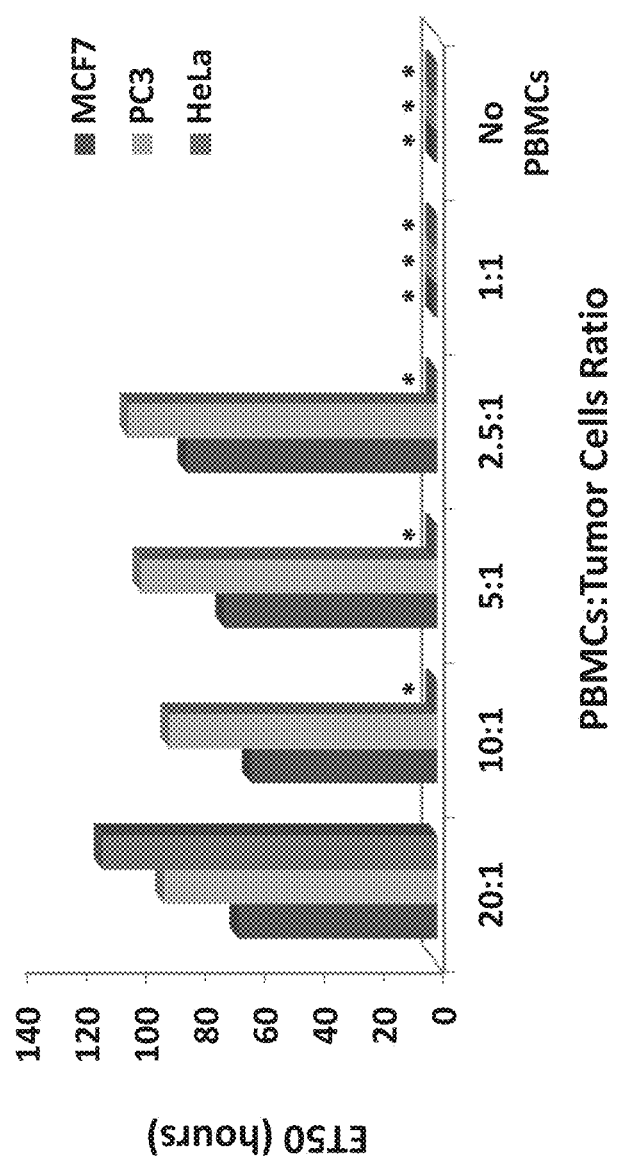

The same dependence from antibody concentration and effector:target ratio is reflected in the ET50 parameter (FIG. 33D), where MCF7 shows the shorter time across all cell ratios, while HeLa decreases up to 50% value only at the highest effector cells ratio.

In summary, these experiments demonstrate the high sensitivity of the impedance-based approach in measuring cytotoxic activity in sophisticated experimental designs. The ability to access the full dynamic of the response over the temporal scale allows better characterization of reagent efficacy and also a better understanding of the dynamic of cell killing in relation to cancer cell type and amount of effector cells. Such detailed analysis is impossible or labor intensive when conducted with end point assays like 51Cr release or flow cytometry. The xCELLigence platform instead, thanks to the simplicity of the set up and the absence of any labeling step allows fast and easy establishment of high throughput experiments with multiple doses and replicates. Furthermore, the absence of any labeling still allows secondary analysis to be performed on the same cells.

Example 10

B Cell Killing Assay Using Cell-Substrate Impedance Monitoring

Figure 34A:
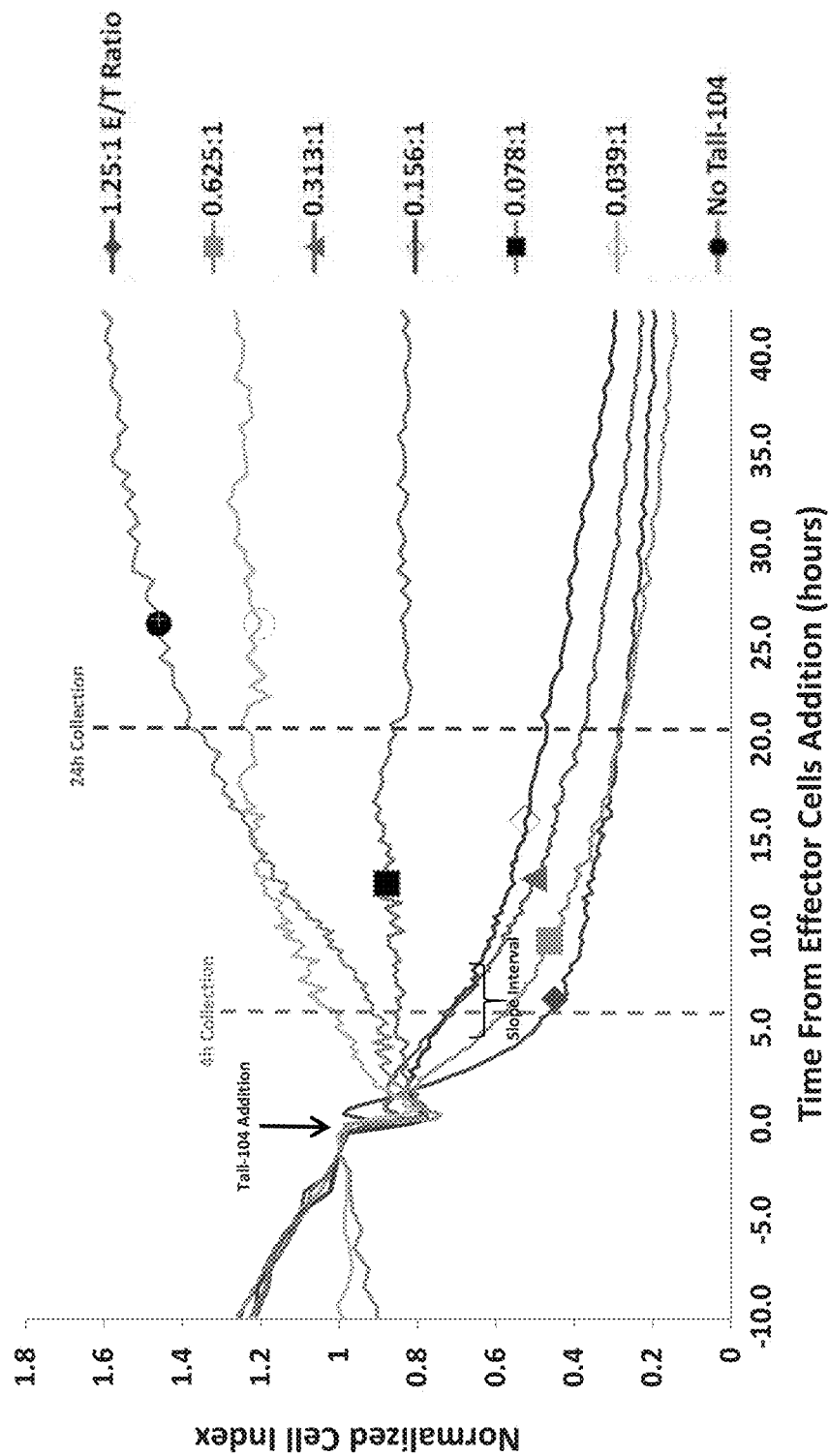
FIG. 34A shows a graph where Daudi B lymphoblast cells were seeded at a density of 80,000 cells/well on wells coated overnight at 4° C. with 1 µg/ml Goat Anti-Human IgM (25 ul). The day after, Tall-104 T lymphoblast cells were added at a density corresponding to effector:target ratios of 1.25:1; 0.625:1; 0.313:1; 0.156:1; 0.078:1 and 0.039:1 FIG. 34B—The slope plot of (A) between time points 4 and 24 after addition of TALL 104. No Tall-104 and the slowest concentrations have positive slope, while all the others have dose-dependent negative values.

Daudi B lymphoblast cells were labeled with 5 mM Cell Trace Violet (ThermoFisher scientific) at 37° C. for 20 min and seeded at a density of 80,000 cells/well on wells coated overnight at 4° C. with 1 µg/ml Goat Anti-Human IgM (25 ul). The day after, Tall-104 T lymphoblast cells were added at a density corresponding to effector:target ratios of 1.25:1; 0.625:1; 0.313:1; 0.156:1; 0.078:1 and 0.039:1 (FIG. 34A). Total volume was kept constant between wells. CI measurement was performed every 15 min for 54 hours.

Figure 34C:
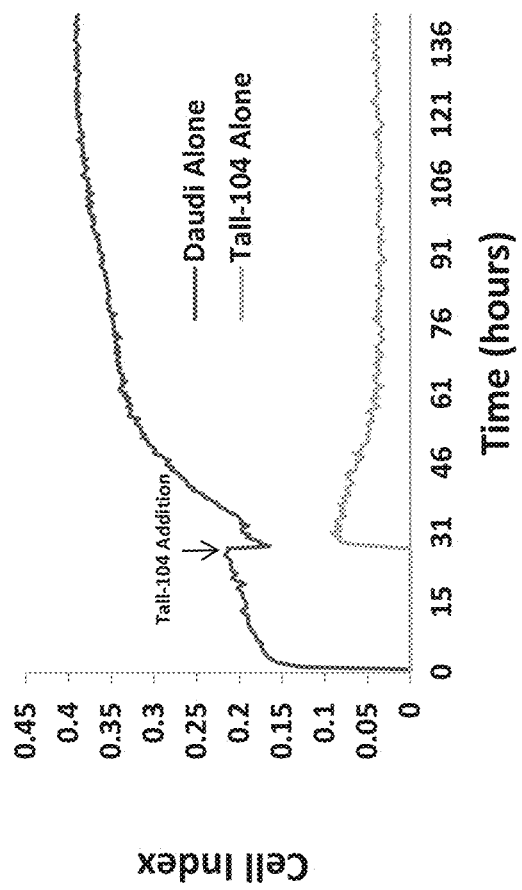
FIG. 34C—The Daudi alone and Tall-104 alone plot shows that Tall-104 have negligible contribution to the CI on IgM coated plates. Tall-104 plot is reported for the maximum amount of Tall-104 (1.25:1) (FIG. 34C).
Figure 34B:
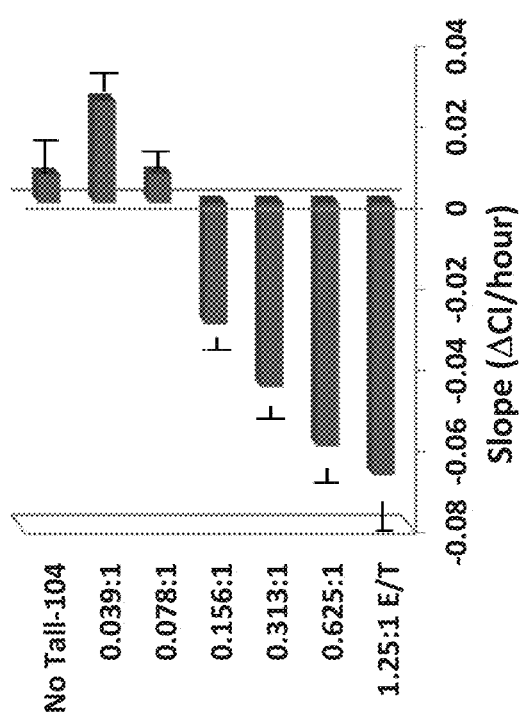
Figure 35:
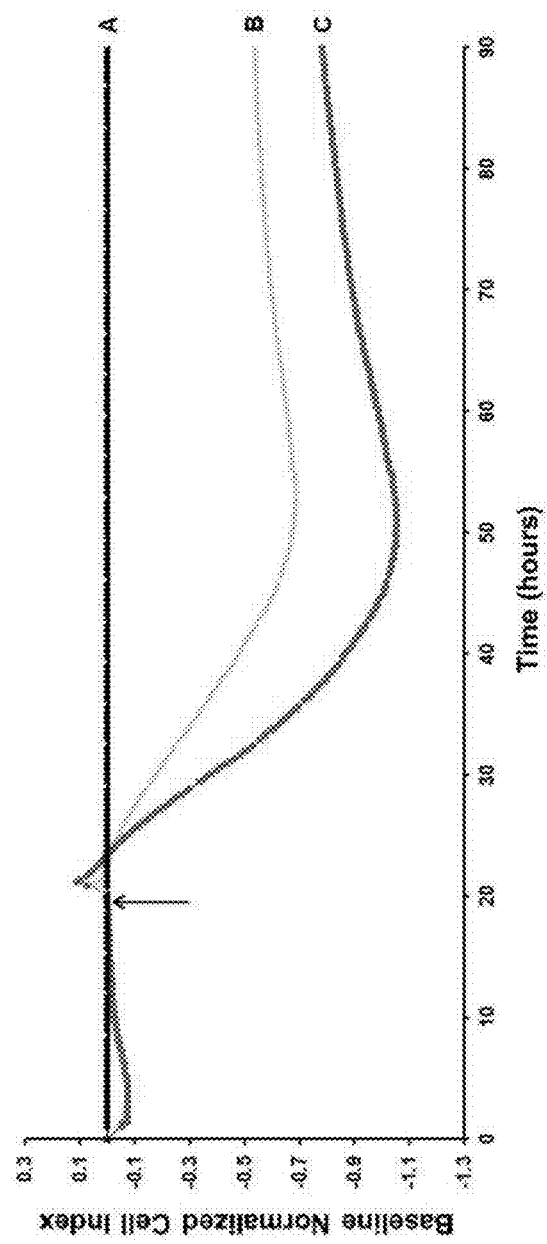
FIG. 35 depicts results from a study where the wells of an E-Plate 96 were pre-coated with anti-CD40 antibody (4 µg/mL in PBS; three hour incubation at room temperature.) After washing wells with PBS, Daudi B cells were added at a density of 80,000 cells/well. 19.9 hours after seeding the Daudi cells, NK-92 effector cells were added in different quantities. Impedance was subsequently monitored for an additional 70 hours. Arrow indicates point of effector cell addition. (A) Zero NK-92 cells. (B) 80,000 NK-92 cells. (C) 160,000 NK-92 cells.

The CI plot was normalized at last reading before adding the Tall-104 (FIG. 34A). The slope was measured on the normalized curve between the first 10 hours after Tall-104 addition. The CI plot shows nice dose-response killing of B cells proportional to the ratio of effector cells. All concentrations, with the exception of two, show time-dependent reduction of CI. 0.078:1 has an immediate cytostatic effect, with the CI constant. 0.039:1 slows down CI increase compared to no Tall-104 sample. The same progression is evident in the slope plot. No Tall-104 and the slowest concentrations have positive slope, while all the others have dose-dependent negative values (FIG. 34B). The Daudi alone and Tall-104 alone plot shows that Tall-104 have negligible contribution to the CI on IgM coated plates. Tall-104 plot is reported for the maximum amount of Tall-104 (1.25:1) (FIG. 34C).

In another example, Daudi cells were immobilized at a density of 80,000 cells/well in an E-Plate 96 by pre-coating wells with anti-CD40 antibody. 19.9 hours after seeding the Daudi cells, effector cells (NK-92) were added in different quantities. Impedance was subsequently monitored for an additional 70 hours. The raw impedance data was collected, averaged, normalized followed by subtraction of negative control trace, which is the trace of B cells without addition of effectors. The results indicate that B cells can indeed be tethered to the bottom of the wells via an antibody (in this case an antibody directed against CD40) and effector-mediated cytotoxicity can subsequently be monitored.

What is claimed is:

1. A method of assessing cytolysis of cancer cells, the method comprising:
   a) providing a cell-substrate impedance monitoring device operably connected to an impedance analyzer, wherein the device comprises a well for receiving cells and an electrode array at a base of the well;
   b) adding target cells characterized as cancer cells to the well;
   c) adding effector cells to the well to form a test well, wherein the effector cells are immune cells obtained or derived from a same patient as the target cells;
   d) monitoring cell-substrate impedance of the test well before and after adding the effector cells and optionally deriving an impedance-based parameter from the cell-substrate impedance; and
   e) determining effectiveness of effector cell killing of the target cells by a method selected from the group consisting of:
      comparing area under the curve (AUC) of impedance-based curves over time,
      performing linear regression analysis of the cell-substrate impedance or impedance-based parameter,
      analyzing a killing time 50 (KT50) value, which is determined by calculating time it takes to achieve 50% cytolysis,
      analyzing the impedance-based parameter, wherein the impedance-based parameter is a slope for a time period post effector cell addition, and
      analyzing a baseline normalized cell index curve for curve kinetics, wherein the baseline normalized cell index curve is plotted by removing a negative control well curve from an impedance-based curve, which is plotted from the cell substrate impedance parameter of the monitored well.

2. The method according to claim 1, wherein slopes of the impedance-based curves are plotted against each concentration of effector cells being added.

3. The method according to claim 2, wherein the linear regression analysis is performed by plotting a linear regression.

4. The method according to claim 3, wherein a slope of the plotted linear regression is determined.

5. The method according to claim 4, wherein the slope of the plotted linear regression is indicative of potency of the effector cells being added.

6. The method according to claim 5, wherein the potency of one of the effector cells is compared to the potency of another effector cell by comparing the slopes of linear regression.

7. The method according to claim 1, wherein the area under the curve (AUC) of the impedance-based curve is calculated upon addition of the effector cells.

8. The method according to claim 7, wherein an AUC value for each impedance-based curve is plotted against a corresponding concentration of effector cells being added to the device.

9. The method according to claim 1, wherein duration of monitoring the cell-substrate impedance runs from immediately after adding the effector cells.

10. The method according to claim 9, wherein a dose-response is calculated for the corresponding effector cells being added to device and is indicative of effector potency.

11. The method according to claim 10, wherein the dose-response of one type of effector cell is compared to another type of effector cell using a half-maximal effector concentration which results in 50% response (EC-50) value.

12. The method according to claim 1, wherein the KT50 parameter of target cells is subsequent to adding a given density of effector cells to the wells.

13. The method according to claim 1, wherein the time it takes (KT) to achieve cytolysis at 10%, 20%, 30%, 40%, 60%, 70%, 80%, 90% and 100% is calculated subsequent to adding a given density or a series of densities of effector cells to the wells containing the target cells.

14. The method according to claim 1, wherein slope of the impedance-based curve at a given time interval subsequent to adding the effector cells at different densities is determined.

15. The method according to claim 1, further comprising a step of adding an additional compound suspected of increasing or decreasing effectiveness of effector cell killing of the target cells to the test well and comparing results of step 1e) between the absence and presence of the compound to determine a difference in the effectiveness of effector cell killing of the target cells in response to adding the compound.

16. The method of claim 1, further comprising adding the target cells to a second well of the device designated a control well, adding a negative control compound to the control well, monitoring impedance of the control well and optionally deriving an impedance-based parameter from the impedance of the control well; and performing step 1e) to determine whether adding the compound increases effector cell killing of target cells.

17. The method according to claim 16, wherein the compound is selected from the group consisting of an antibody or antibody fragment, a modified antibody or antibody fragment, and a peptide.

18. The method according to claim 16, wherein the additional compound comprises a check point inhibitor, optionally an antibody or antibody fragment against a member selected from the group consisting of PD1, CTLA-4, CD137, OX40, CD27, CD40L, TIM3 on a surface of effector cells or their respective cognate ligand on a surface of target cells.

19. The method according to claim 16, wherein the compound is a bispecific engager comprising two polypeptides linked together, wherein each of the two polypeptides binds either the effector cells or the target cells thereby joining the effector cells to the target cells.

20. The method according to claim 19, wherein the bispecific engager binds a T-cell surface moiety, optionally cluster of differentiation 3 (CD3).

* * * * *